US011123556B2

(12) United States Patent
Coleman et al.

(10) Patent No.: US 11,123,556 B2
(45) Date of Patent: Sep. 21, 2021

(54) PATIENT THERAPY SYSTEMS AND METHODS

(71) Applicant: CyMedica Orthopedics, Inc., Scottsdale, AZ (US)

(72) Inventors: Struan Coleman, New York, NY (US); Calvin Domenico, Somerville, MA (US); Edison Gieswein, San Antonio, TX (US); Jessica Paparella, Seaford, NY (US); Joshua Butters, Chandler, AZ (US); Marlina Kessler, Phoenix, AZ (US); David Saar, Tempe, AZ (US); Lee Knox, Chandler, AZ (US)

(73) Assignee: CYMEDICA ORTHOPEDICS, INC., Scottsdale, AZ (US)

( * ) Notice: Subject to any disclaimer, the term of this patent is extended or adjusted under 35 U.S.C. 154(b) by 34 days.

(21) Appl. No.: 16/438,136

(22) Filed: Jun. 11, 2019

(65) Prior Publication Data

US 2019/0298998 A1    Oct. 3, 2019

Related U.S. Application Data

(63) Continuation of application No. 15/663,532, filed on Jul. 28, 2017, now Pat. No. 10,315,032, which is a
(Continued)

(51) Int. Cl.
*A61N 1/36* (2006.01)
*A61N 1/04* (2006.01)
(Continued)

(52) U.S. Cl.
CPC ....... *A61N 1/36014* (2013.01); *A61N 1/0452* (2013.01); *A61N 1/0484* (2013.01);
(Continued)

(58) Field of Classification Search
None
See application file for complete search history.

(56) References Cited

U.S. PATENT DOCUMENTS

| 4,697,808 A | 10/1987 | Larson et al. |
| 5,558,627 A * | 9/1996 | Singer .................. A41D 13/018 |
| | | 602/13 |

(Continued)

FOREIGN PATENT DOCUMENTS

| JP | 2011204073 A | 10/2011 |
| JP | 2014523553 A | 3/2012 |

(Continued)

OTHER PUBLICATIONS

International Search Report and Written Opinion for International Application No. PCT/US2016/014973, dated May 12, 2016, 11 pages.
(Continued)

*Primary Examiner* — Brian T Gedeon
(74) *Attorney, Agent, or Firm* — Greenberg Traurig, LLP

(57) ABSTRACT

Some embodiments include a system with a sensor with electrodes including an active electrode and a receiving electrode that is in physical contact with skin of a patient forming an electrical circuit with control electronics of a controller that can measure an electrical parameter using an active electrode and a receiving electrode within a closed loop electrical muscle stimulation system. A sense electrical pulse can be applied to the tissue using the sensor, an electrical parameter measured from the tissue, and a stimulation pulse applied to the tissue based at least in part on the measured electrical parameter. The stimulation is adjustably controlled by the controller to maintain a constant power output to the tissue based on the electrical parameter. A good is coupled to a computer readable medium configured to
(Continued)

store usage data, the usage data relating to the patient's use of the good.

18 Claims, 91 Drawing Sheets

Related U.S. Application Data continuation-in-part of application No. 15/007,014, filed on Jan. 26, 2016, now Pat. No. 10,010,714.

(60) Provisional application No. 62/170,001, filed on Jun. 2, 2015, provisional application No. 62/107,954, filed on Jan. 26, 2015.

(51) Int. Cl.
  *G16H 20/30* (2018.01)
  *G16H 50/20* (2018.01)
  *G16H 40/67* (2018.01)
  *G16H 40/63* (2018.01)
  *A61F 5/01* (2006.01)
  *G16H 20/40* (2018.01)

(52) U.S. Cl.
  CPC ......... *A61N 1/36003* (2013.01); *G16H 20/30* (2018.01); *G16H 20/40* (2018.01); *G16H 40/63* (2018.01); *G16H 40/67* (2018.01); *G16H 50/20* (2018.01); *A61F 5/01* (2013.01)

(56) References Cited

U.S. PATENT DOCUMENTS

| | | | |
|---|---|---|---|
| 8,870,798 | B2 | 10/2014 | Coleman |
| 9,072,898 | B2 | 7/2015 | Coleman et al. |
| 9,486,627 | B1 * | 11/2016 | White ............... A61N 1/36034 |
| 9,700,718 | B2 | 7/2017 | Coleman et al. |
| 9,775,662 | B2 * | 10/2017 | Ingvarsson ........ A61N 1/36003 |
| 2008/0082145 | A1 | 4/2008 | Skwarek et al. |
| 2013/0041426 | A1 | 2/2013 | Grigoriev et al. |
| 2013/0123568 | A1 | 5/2013 | Hamilton et al. |
| 2013/0204169 | A1 | 8/2013 | Poepperling et al. |
| 2014/0343628 | A1 | 2/2014 | Chen |
| 2014/0163444 | A1 | 6/2014 | Ingvarsson et al. |
| 2014/0249466 | A1 | 9/2014 | Hakim |
| 2014/0276298 | A1 | 9/2014 | Coleman et al. |
| 2014/0343629 | A1 | 11/2014 | Kaula et al. |
| 2015/0073232 | A1 | 3/2015 | Ahmad et al. |
| 2015/0306385 | A1 | 10/2015 | Coleman et al. |
| 2016/0213924 | A1 | 7/2016 | Coleman et al. |
| 2016/0310731 | A1 | 10/2016 | Dixon et al. |
| 2017/0157396 | A1 * | 6/2017 | Dixon ............... A61N 1/36146 |
| 2018/0015284 | A1 | 1/2018 | Coleman et al. |
| 2018/0042654 | A1 | 2/2018 | Ingvarsson et al. |

FOREIGN PATENT DOCUMENTS

| | | |
|---|---|---|
| JP | 2012060479 A | 9/2014 |
| WO | 2014/165834 A1 | 10/2014 |

OTHER PUBLICATIONS

International Search Report and Written Opinion for International Application No. PCT/US2018/044124, dated Jan. 17, 2019, 9 pages.
Extended European Search Report dated Aug. 4, 2020 for European Application No. 20159366.2 (7 pages).

* cited by examiner

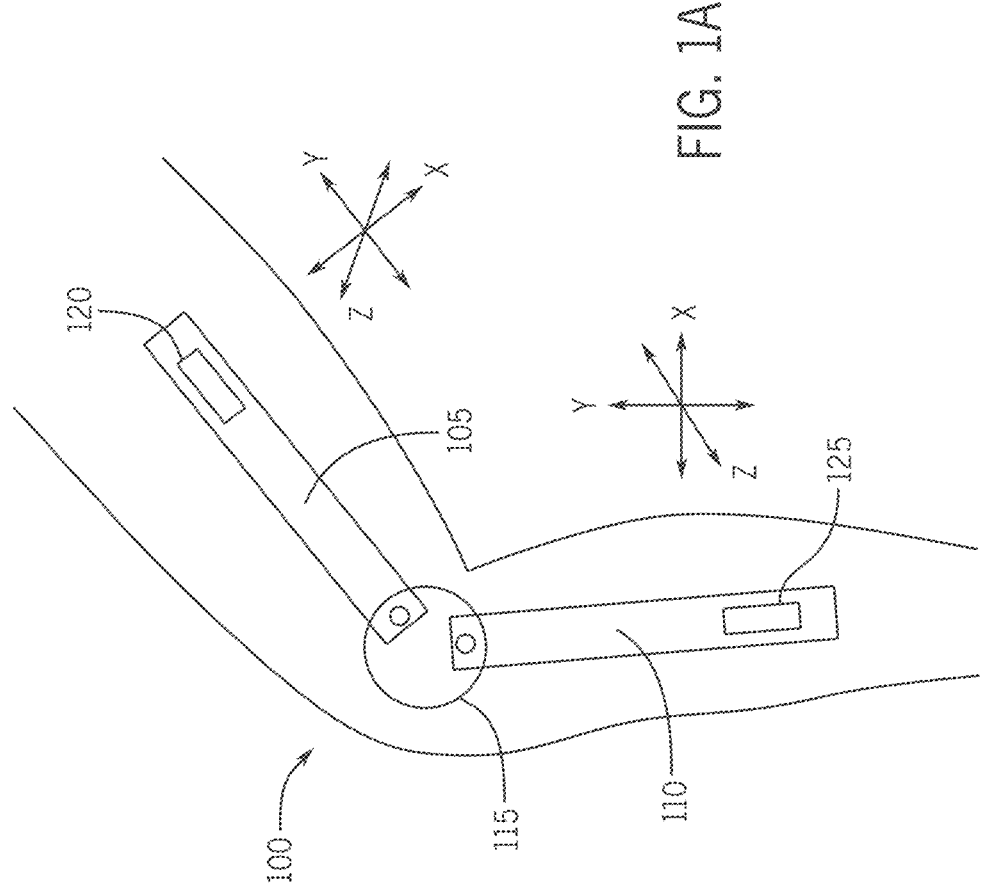

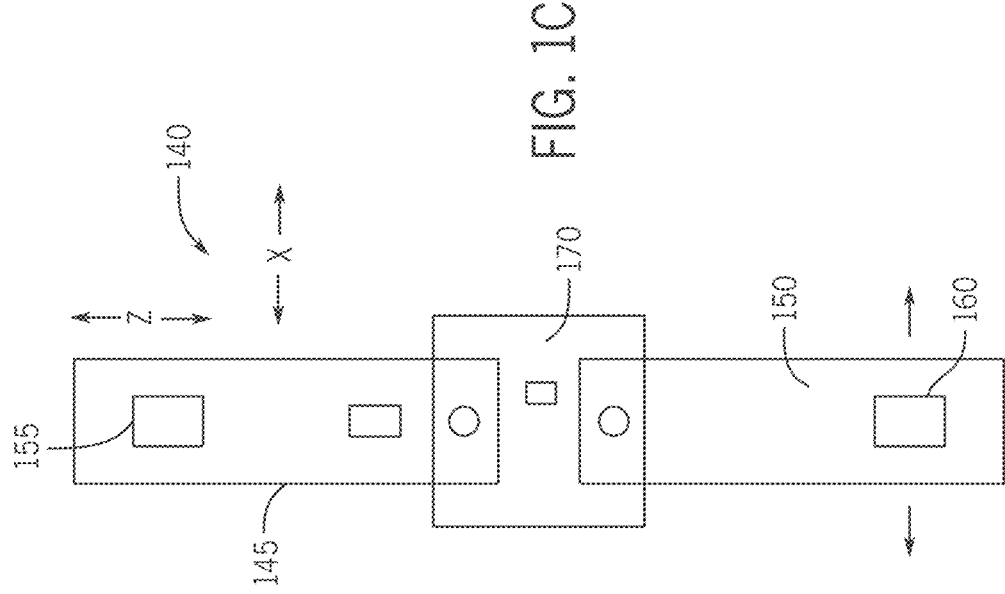

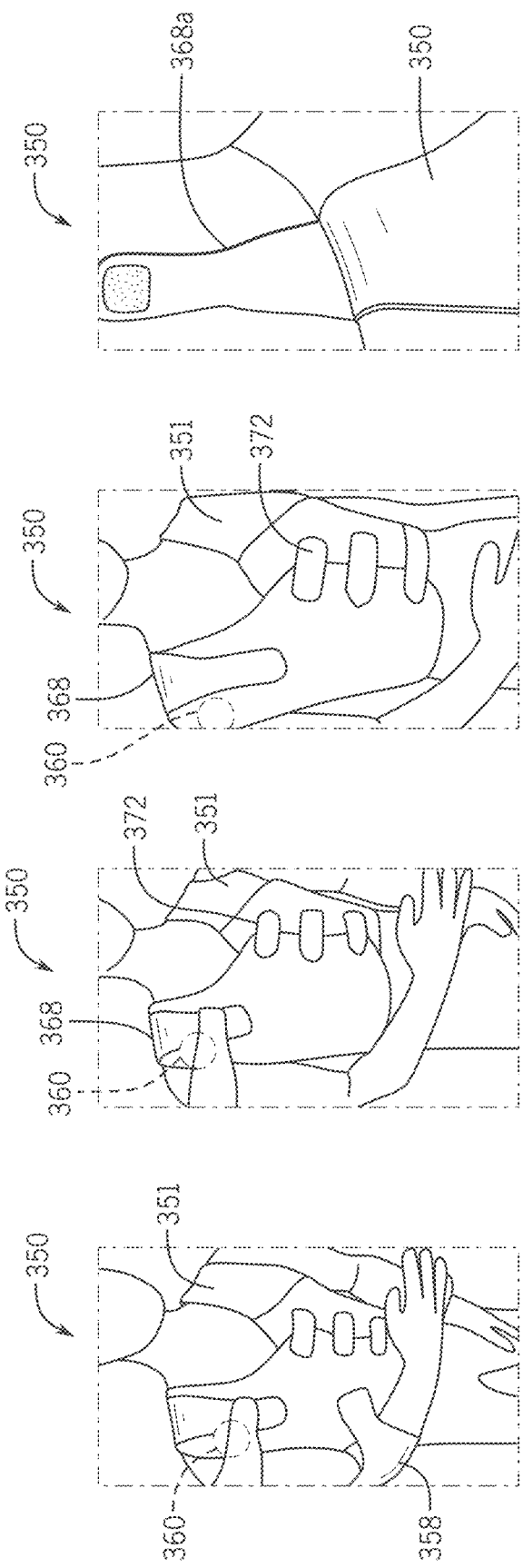

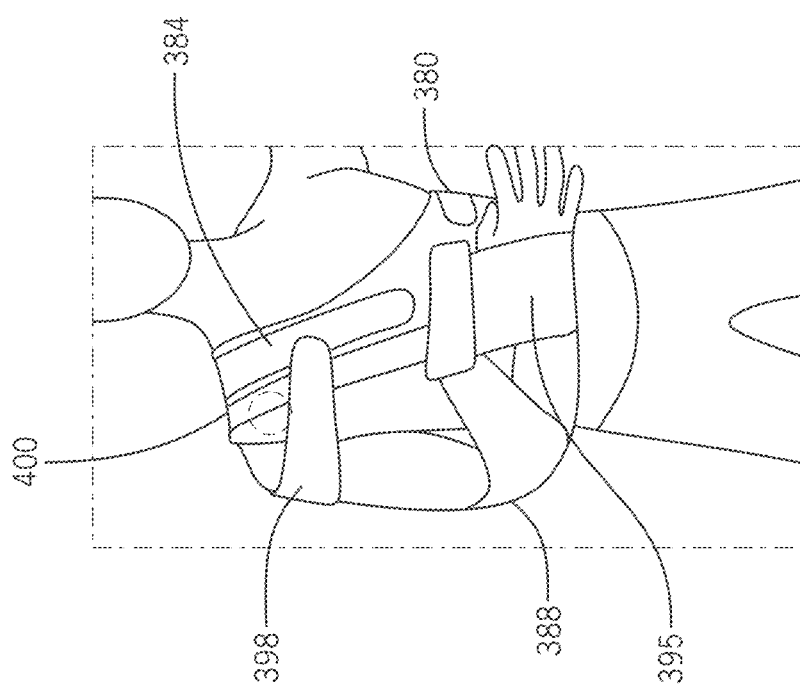

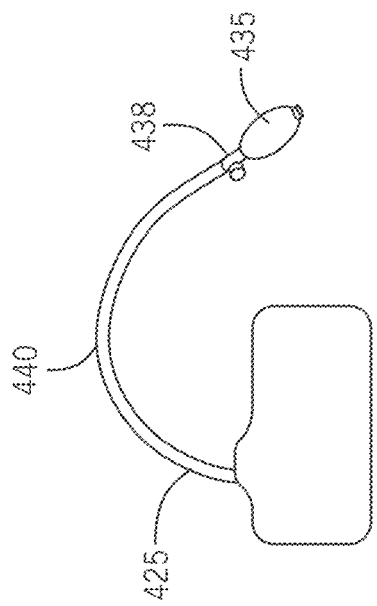
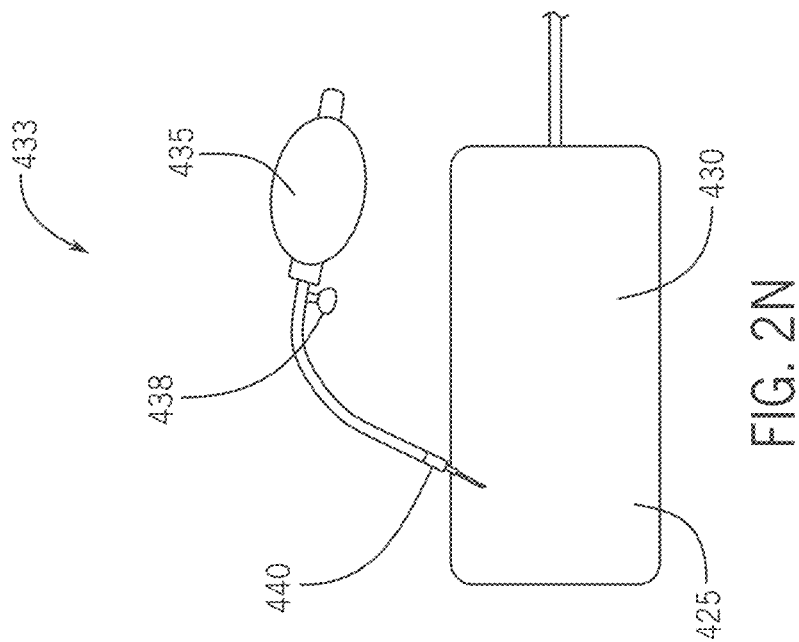

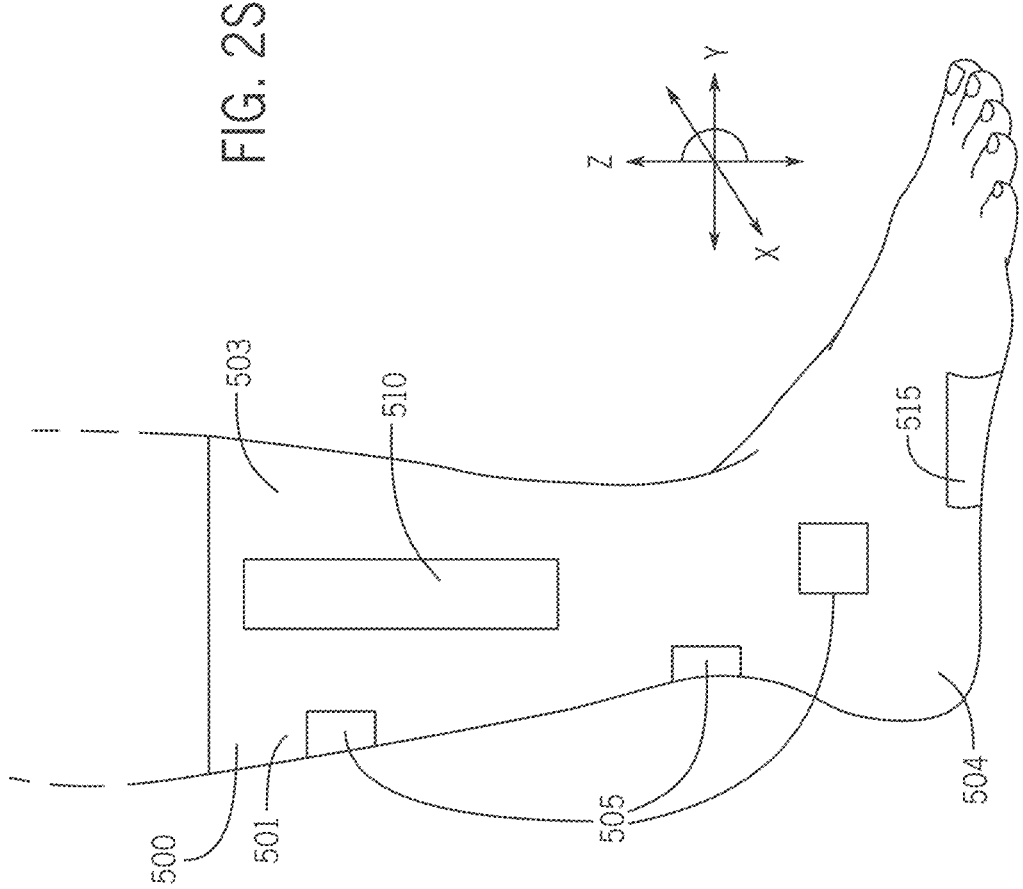

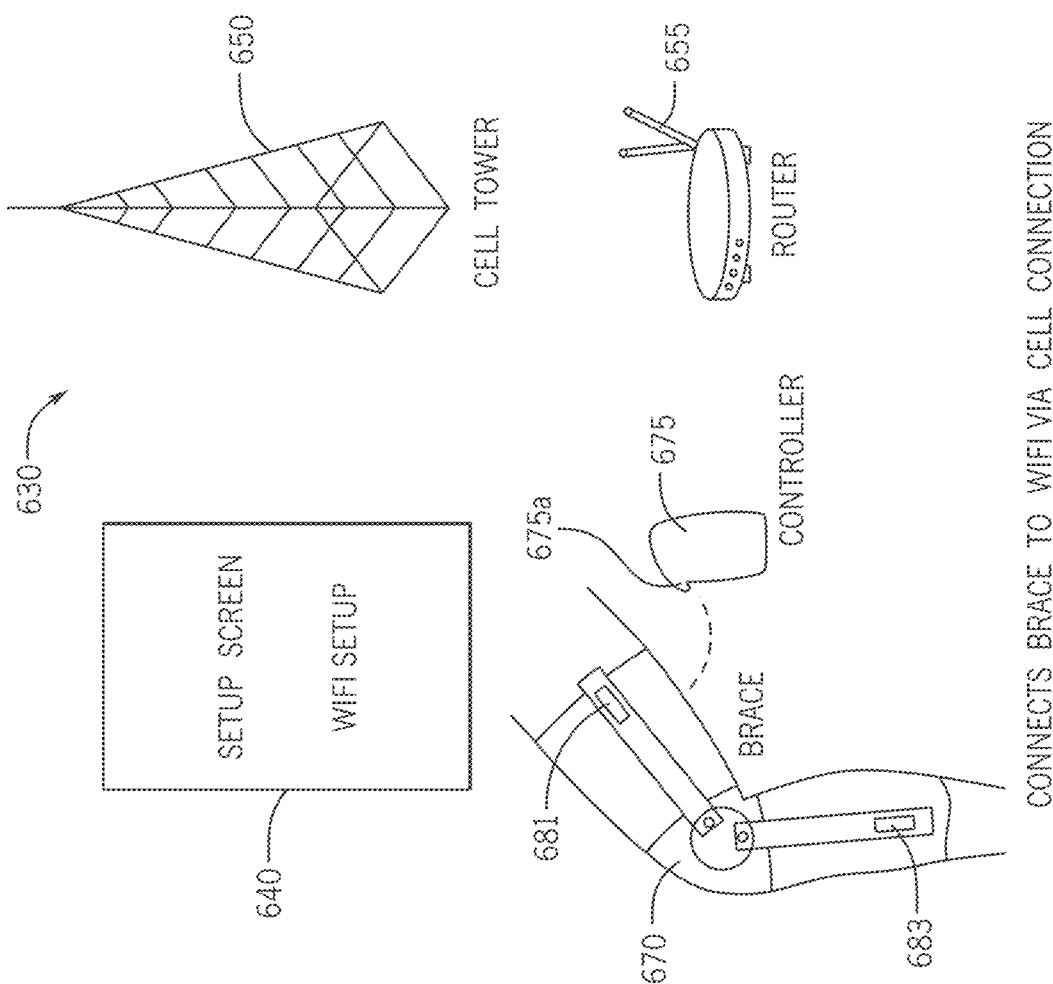

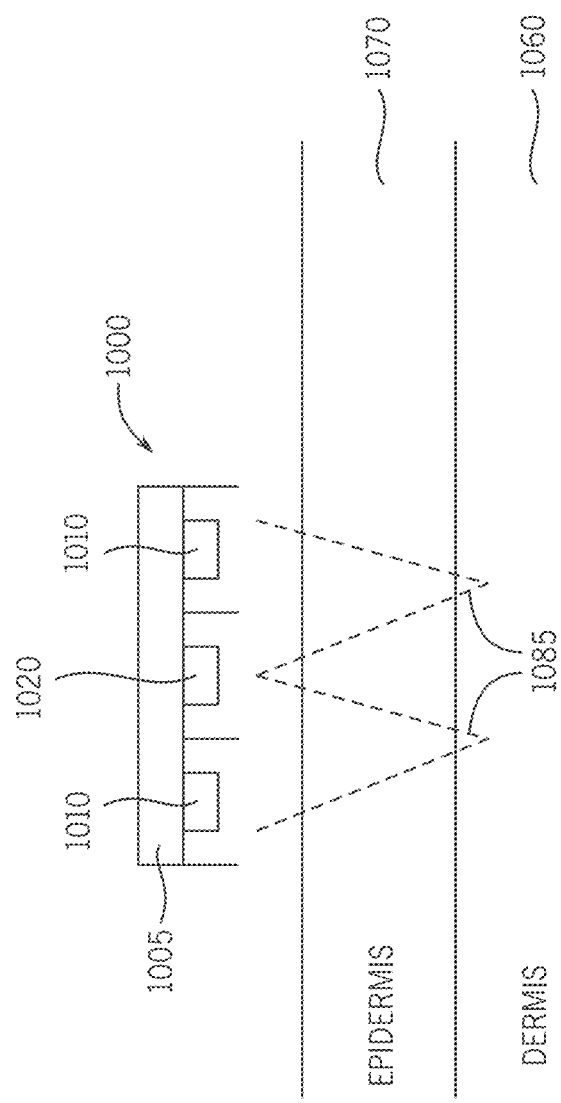

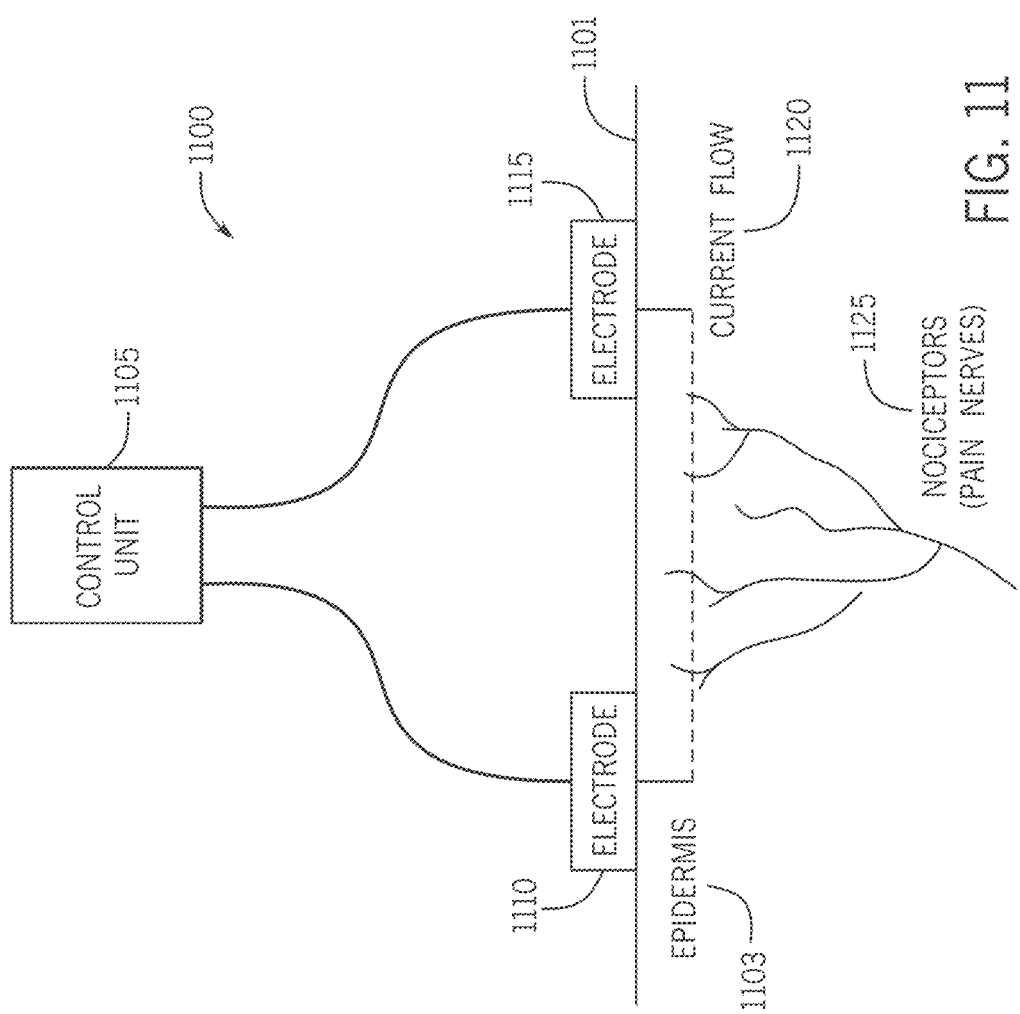

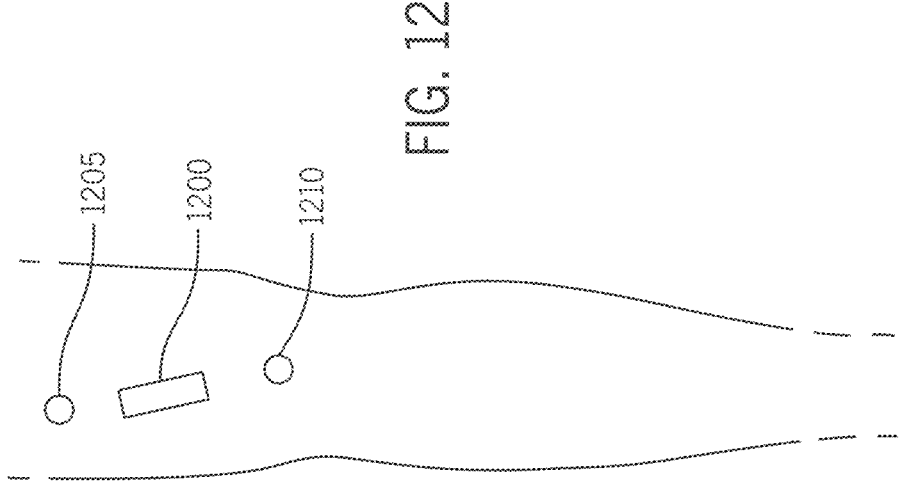

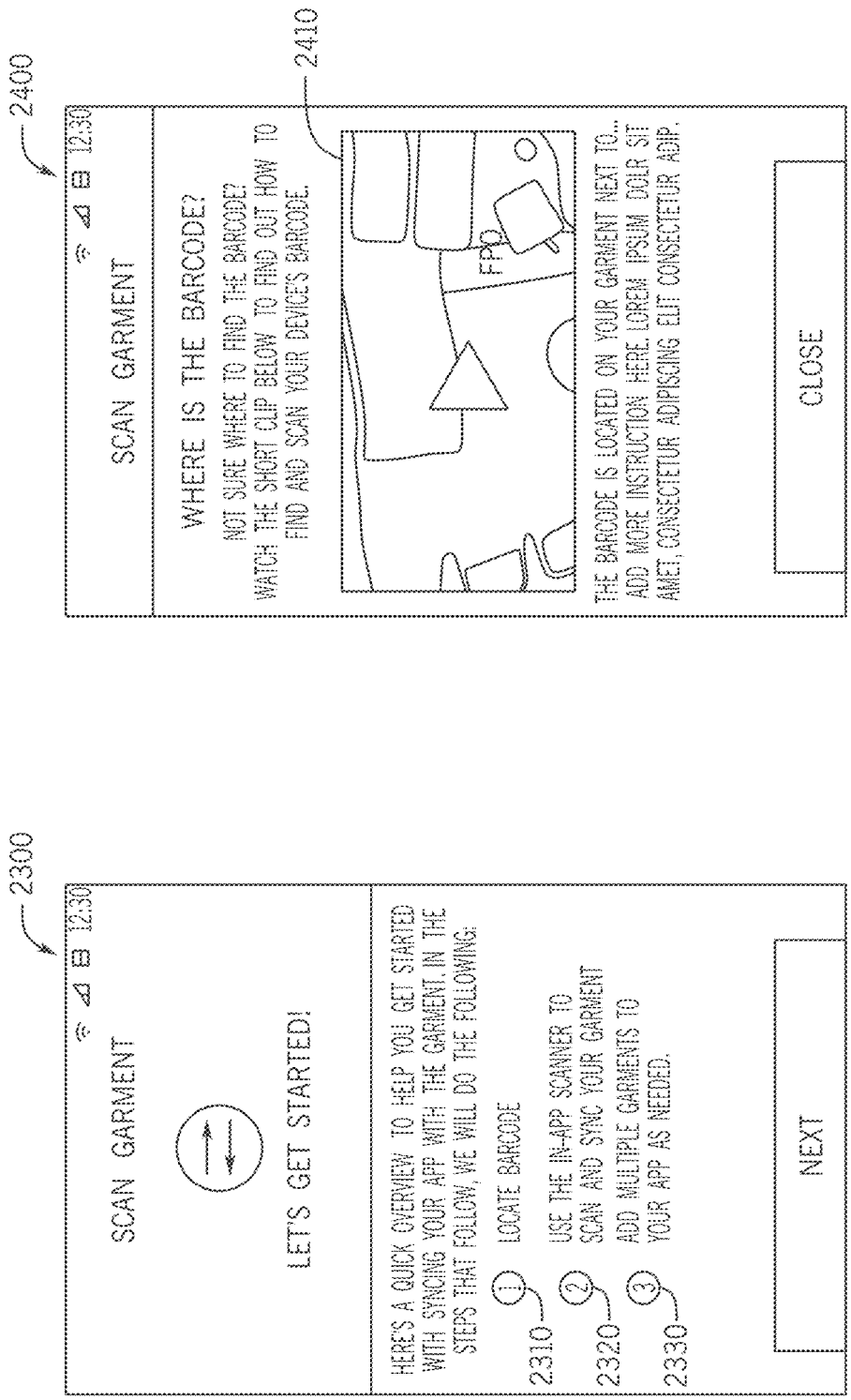

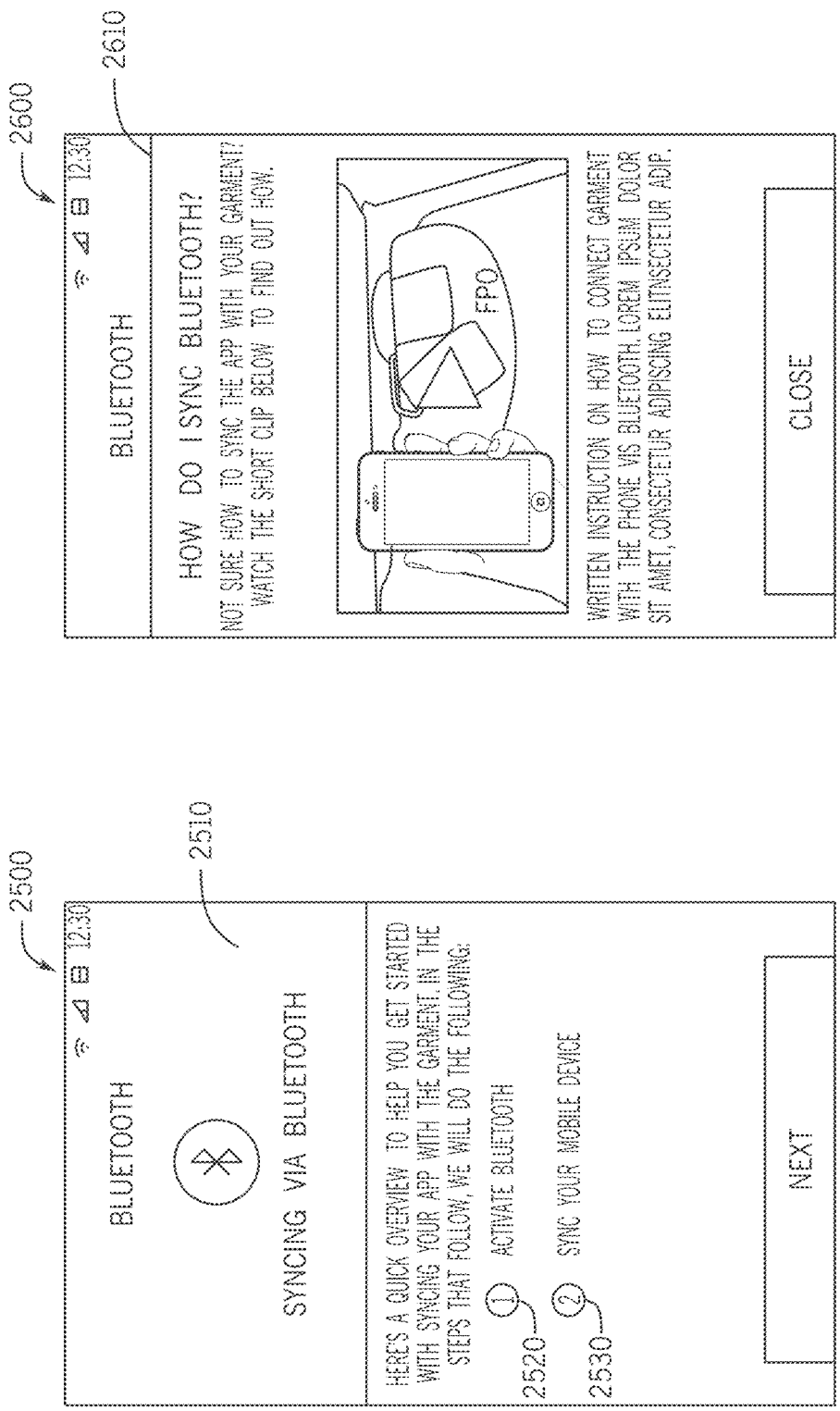

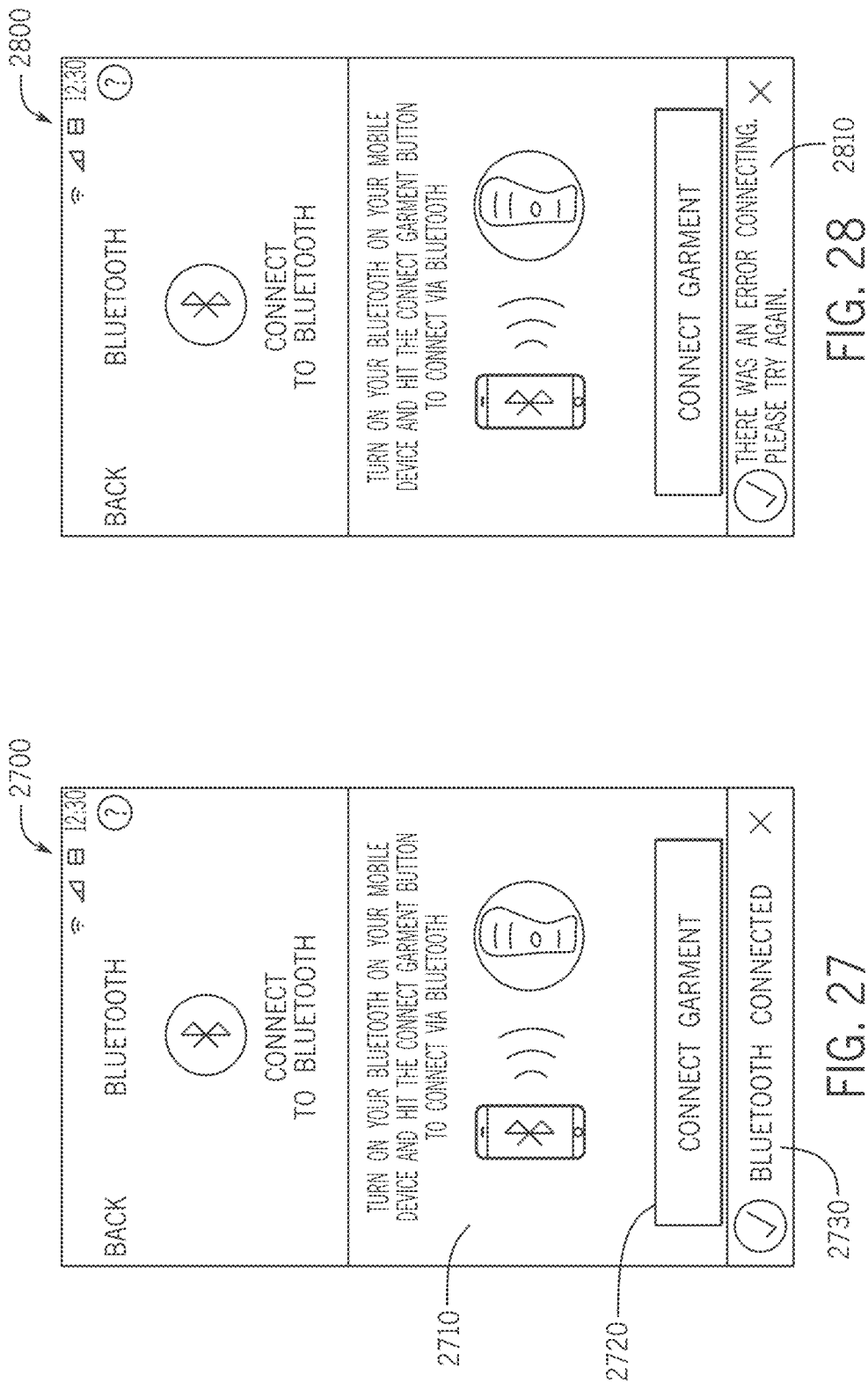

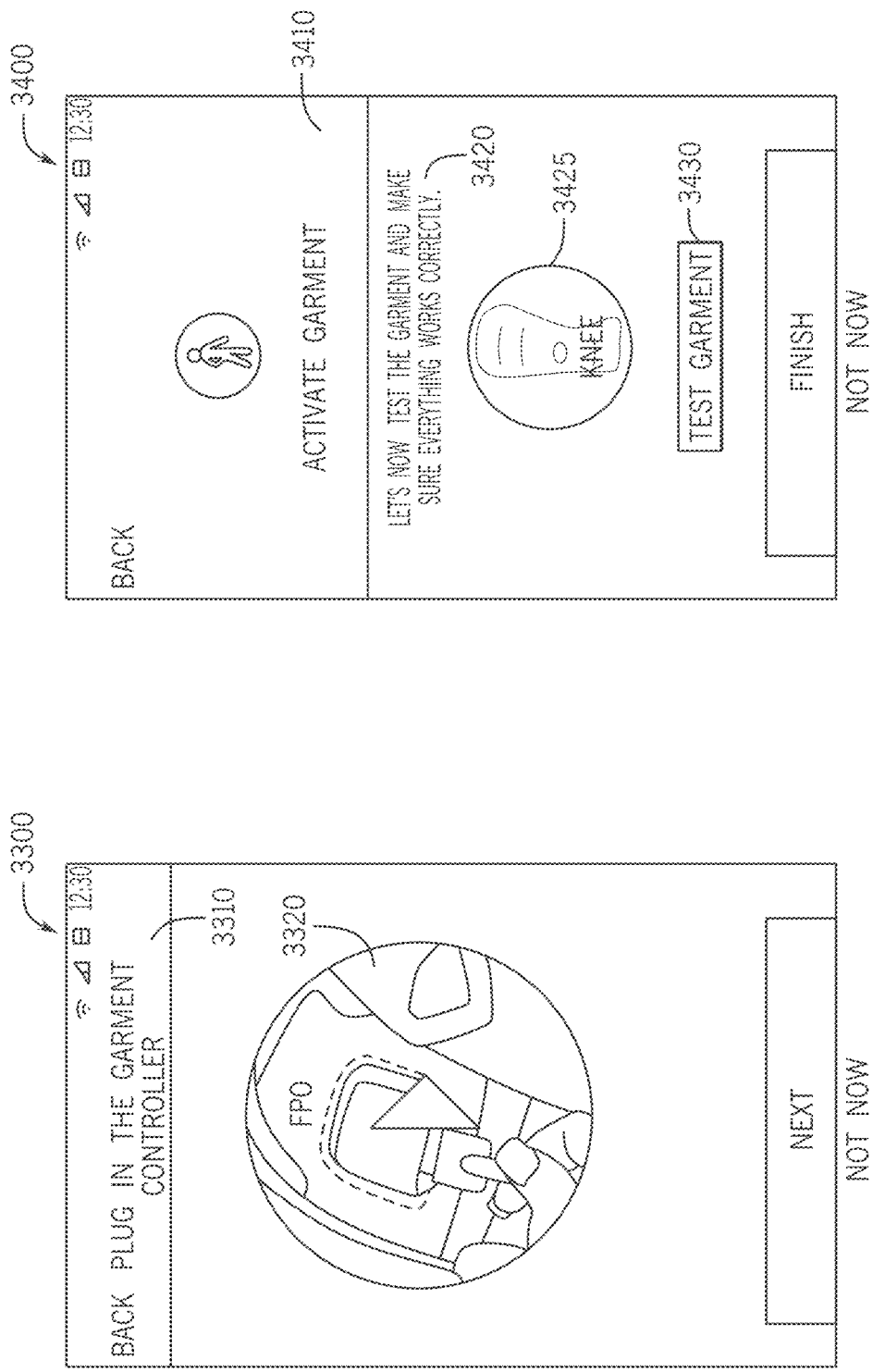

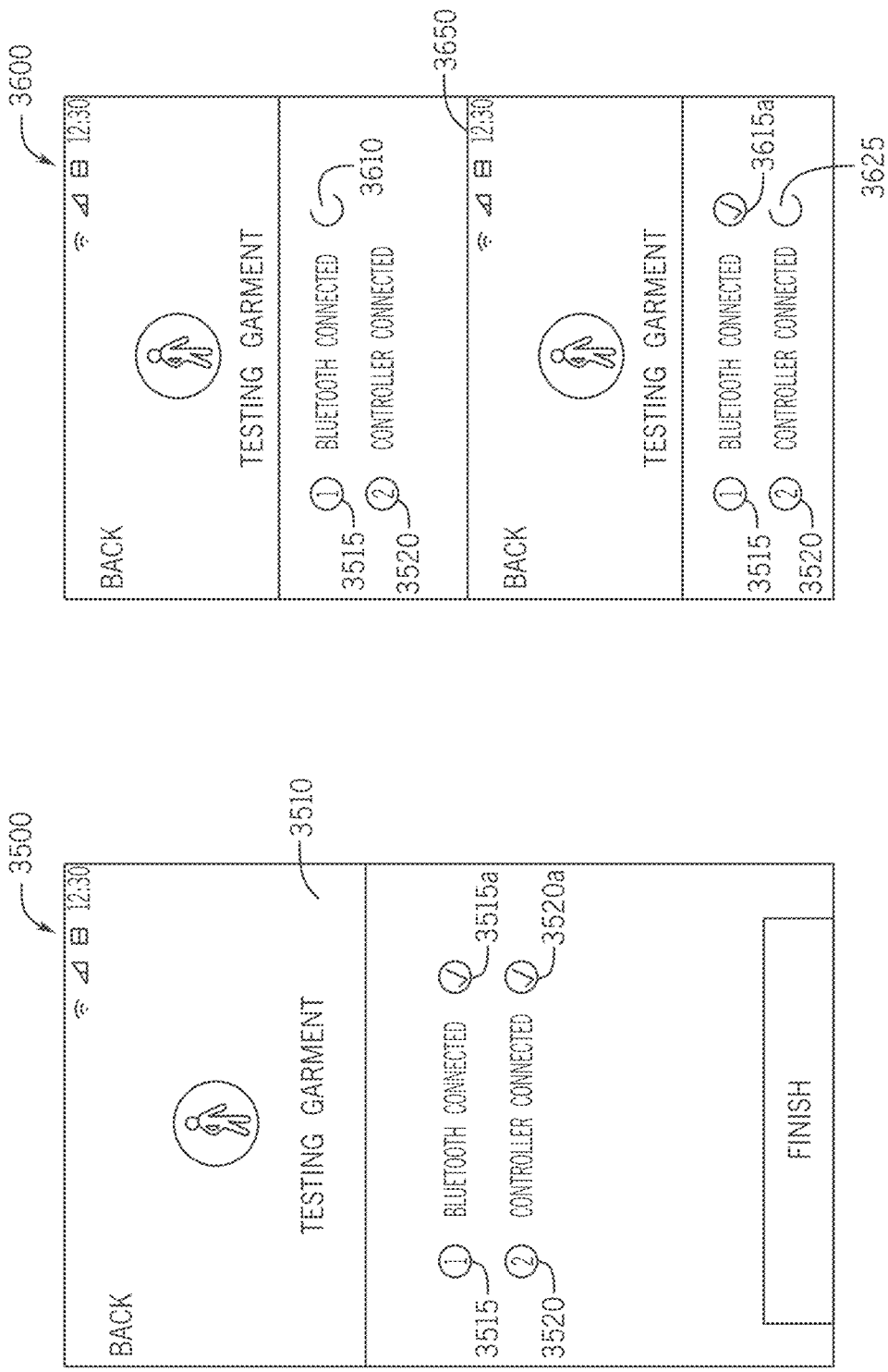

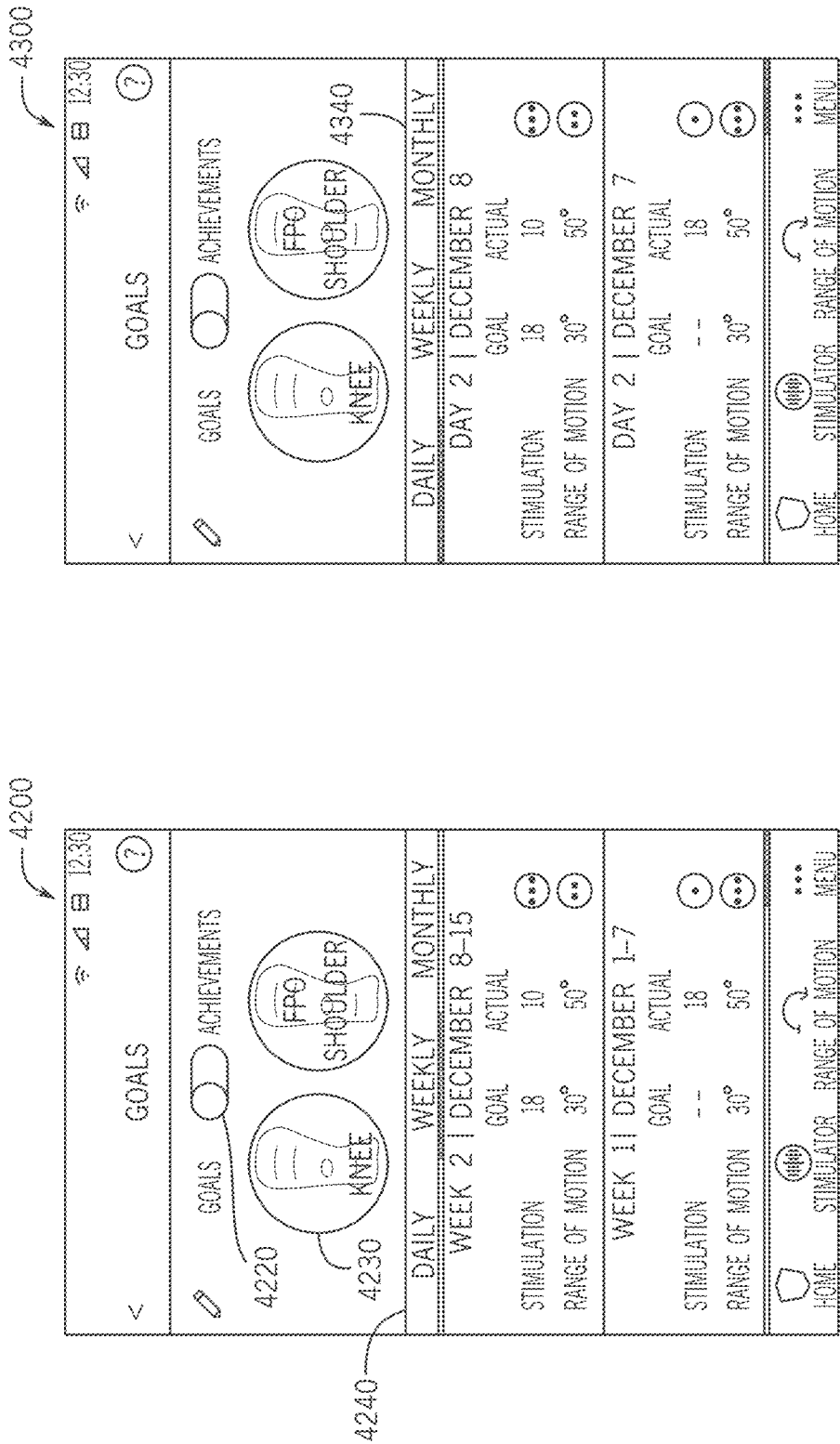

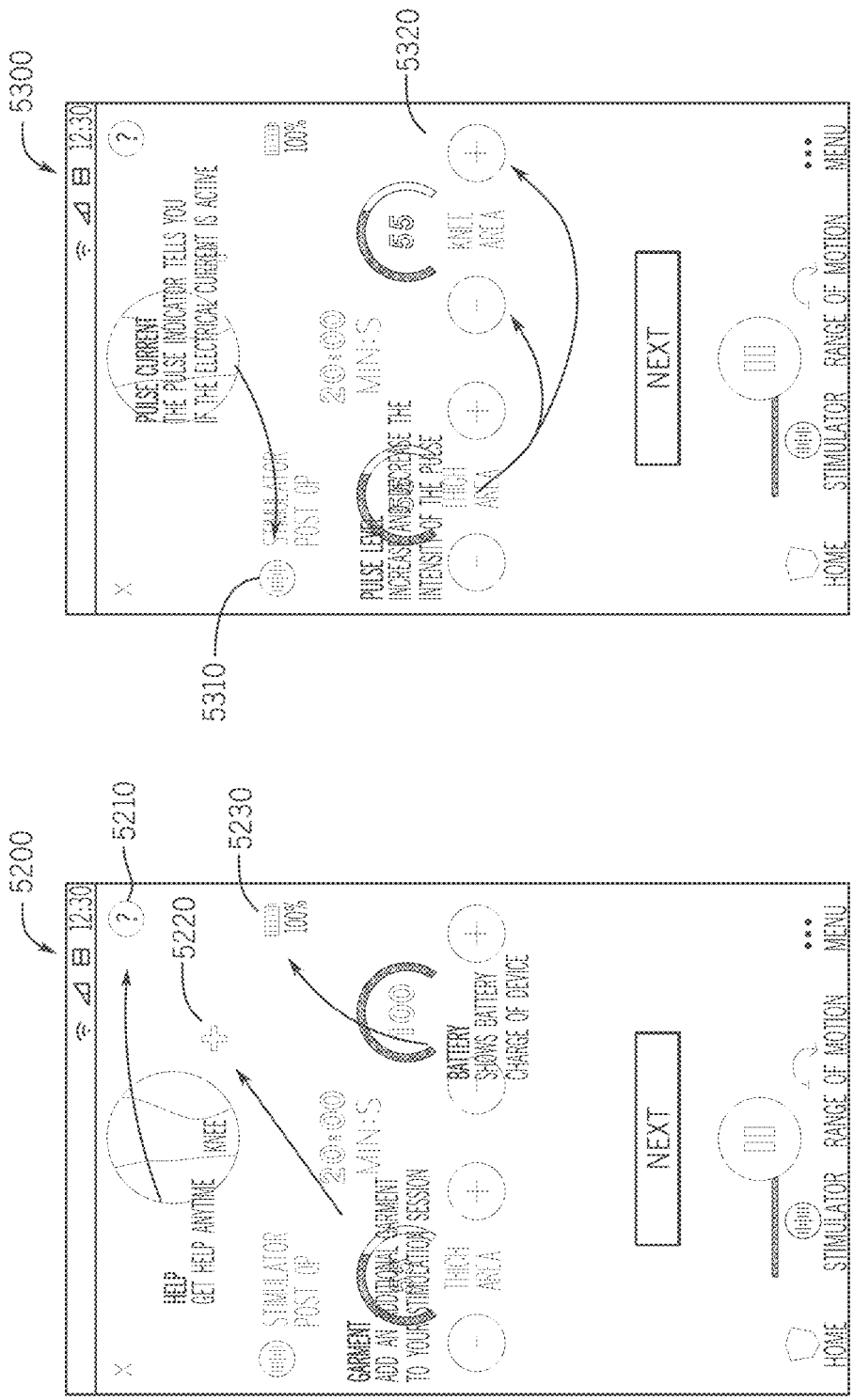

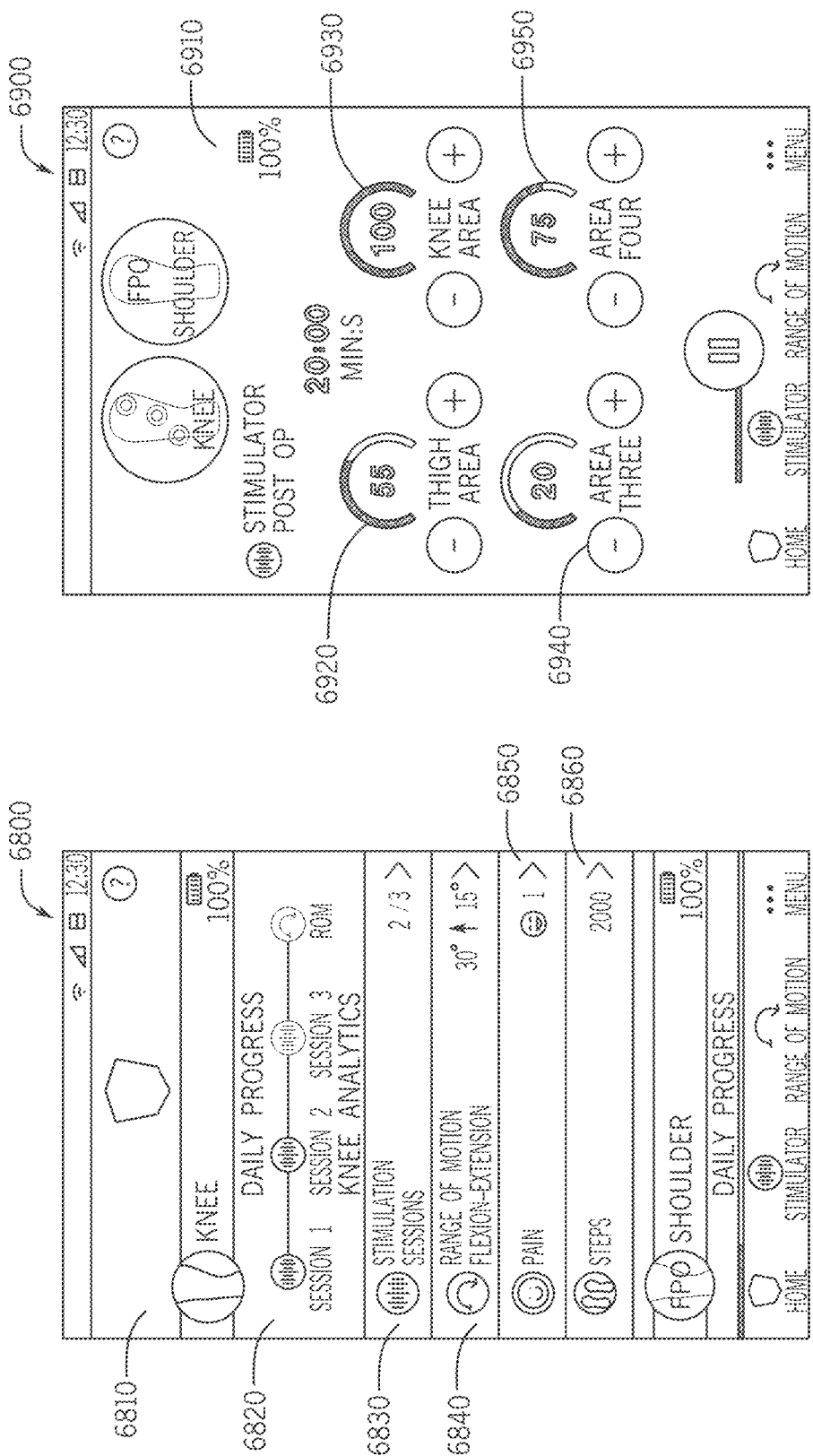

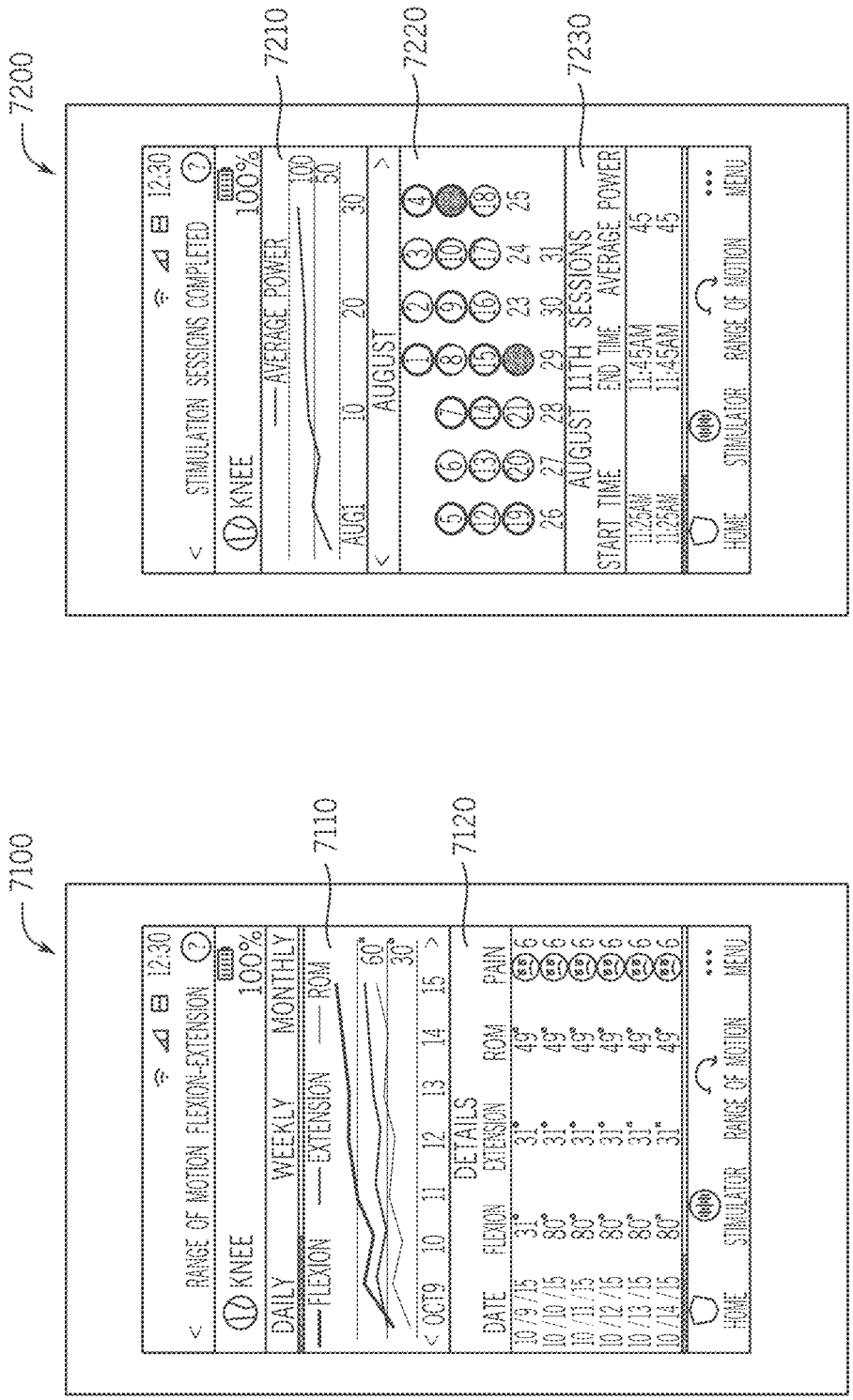

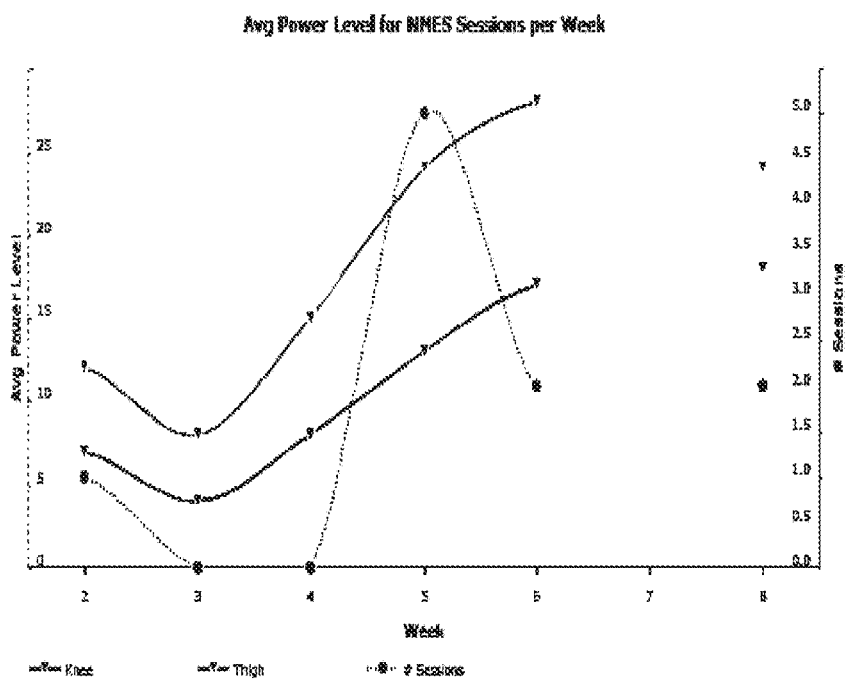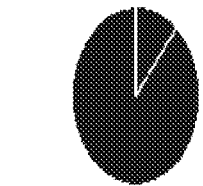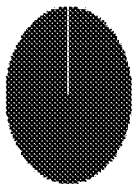
FIG. 85

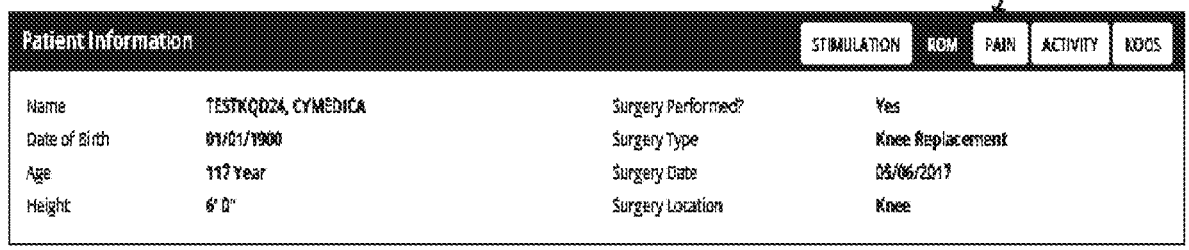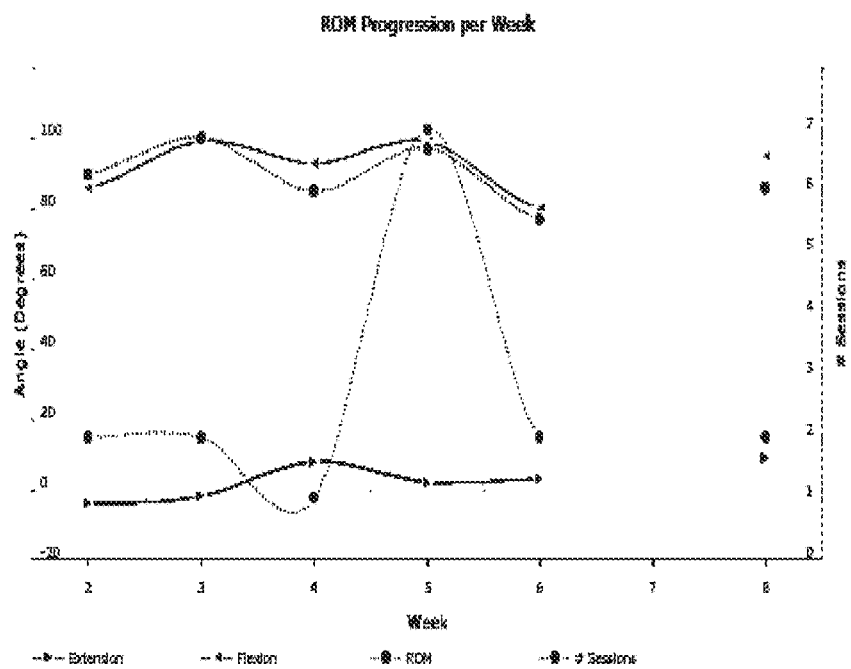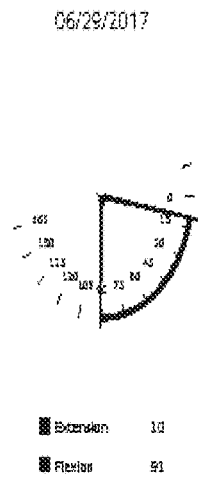
FIG. 86

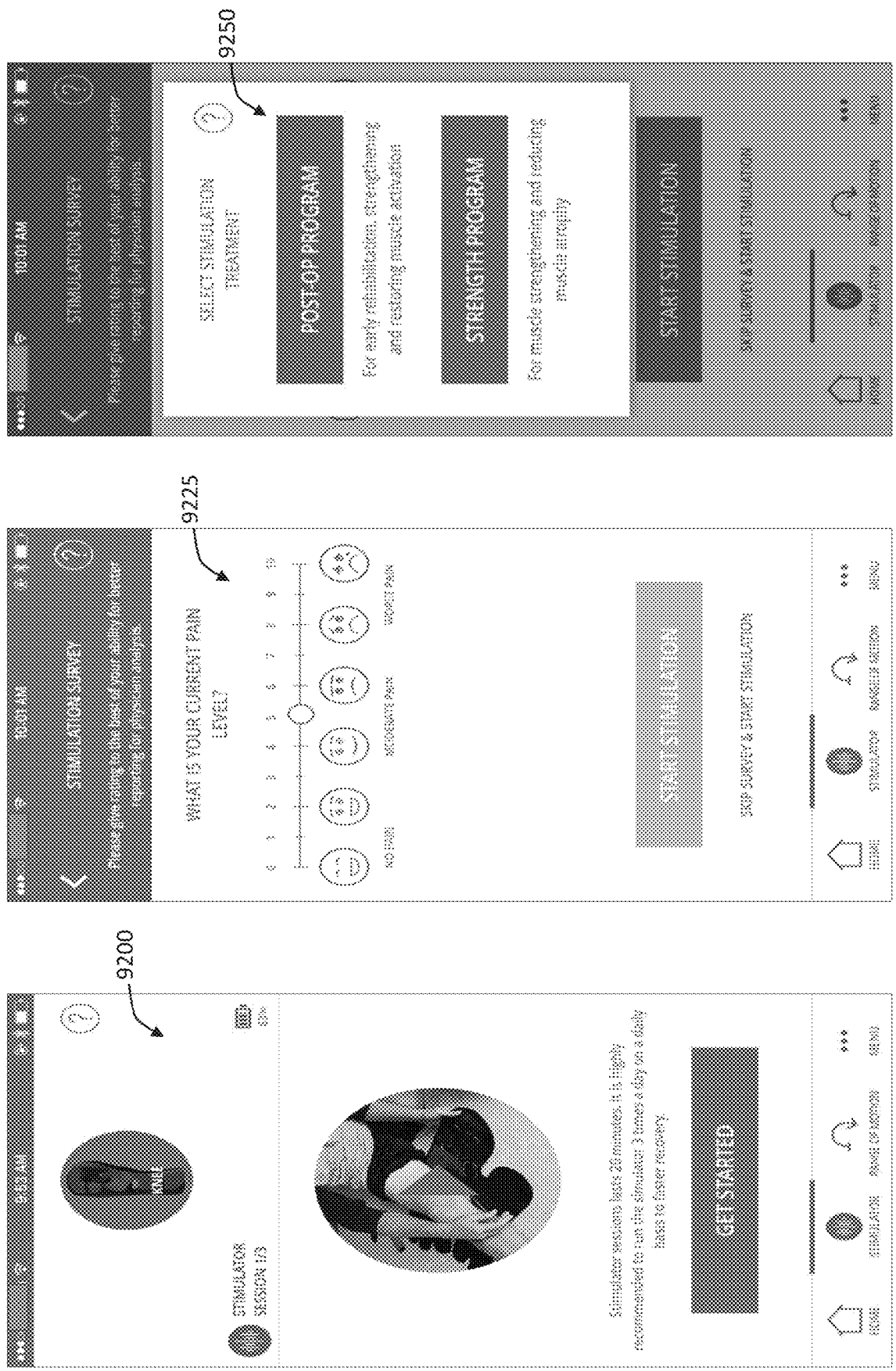

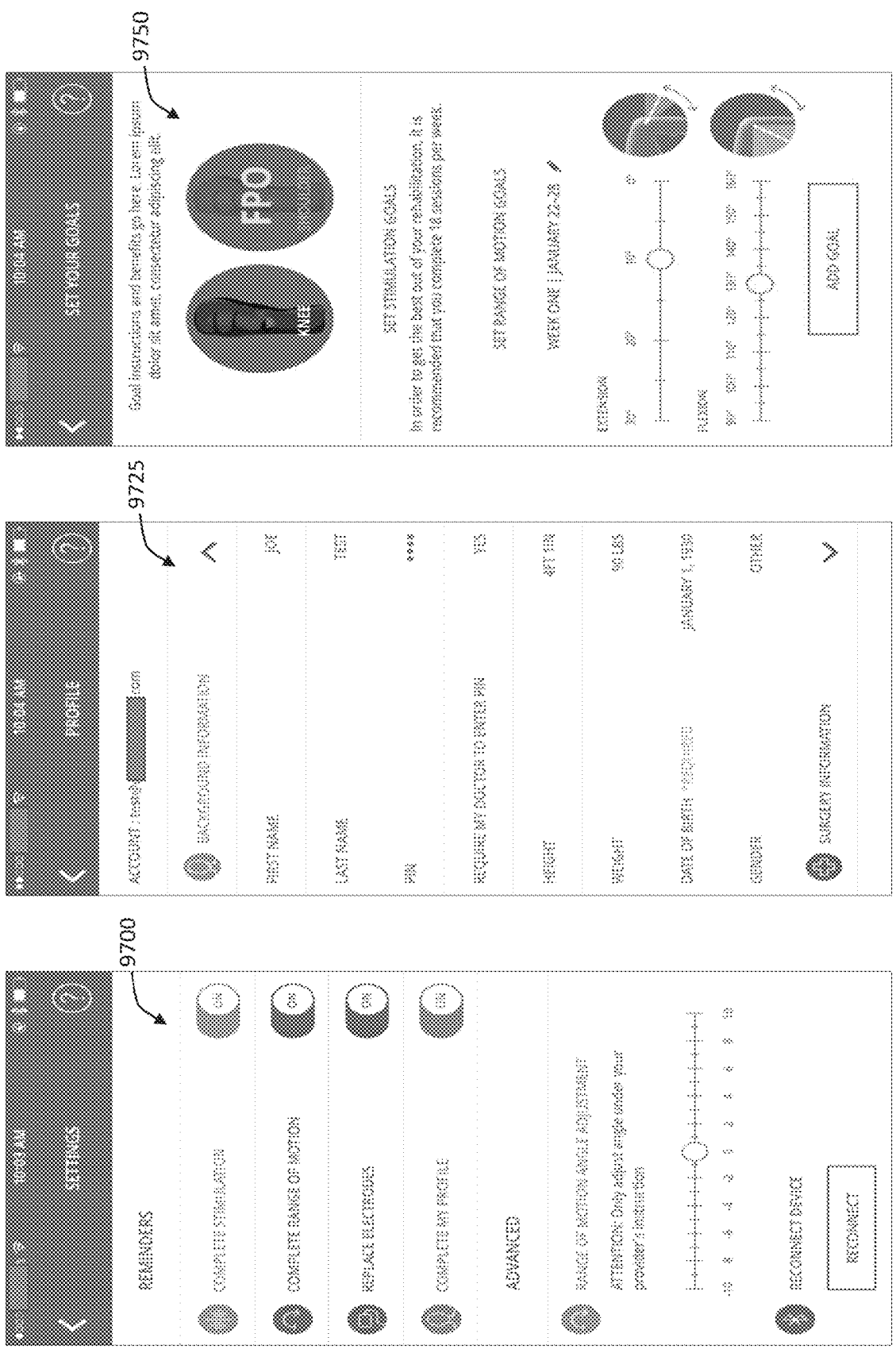

PATIENT THERAPY SYSTEMS AND METHODS

RELATED APPLICATIONS

This application is a continuation of U.S. patent application Ser. No. 15/663,532, filed Jul. 28, 2017, entitled "PATIENT THERAPY SYSTEMS AND METHODS", which is a Continuation-in-Part of U.S. patent application Ser. No. 15/007,014, filed Jan. 26, 2016, entitled "PATIENT THERAPY SYSTEMS AND METHODS", which claims the benefit of and priority to U.S. Provisional Application No. 62/107,954, filed Jan. 26, 2015, entitled "PATIENT THERAPY SYSTEMS AND METHODS", and U.S. Provisional Application No. 62/170,001, filed Jun. 2, 2015, entitled "PATIENT STIMULATION SYSTEM AND METHOD", the entire contents of which are incorporated herein by reference.

BACKGROUND

Orthopedic braces and wraps are useful as preventative aids to prevent injuries to joints caused by motions or orientations of the joint that are outside the biomechanical limits of the joint. Orthopedic braces and wraps are also useful to promote proper healing of a joint following an injury to, or surgery on, the joint, and can be used to stabilize joints with arthritis, thereby alleviating pain.

A critical part of the successful healing process after an injury and potential surgery is the rehabilitation process. As a primary part of the rehabilitation process, patients usually see a physical therapist to regain range of motion as well as strengthen their muscle(s) after suffering an injury, undergoing surgery, or when afflicted with arthritis, conditions which can result in muscle atrophy. Knee braces in particular are widely used to treat a variety of knee infirmities. Such braces may be configured to impart forces or leverage on the limbs surrounding the knee joint in order to relieve compressive forces within a portion of the knee joint, or to reduce the load on that portion of the knee. Moreover, in the event that knee ligaments are weak and infirm or surgically repaired, a knee brace may stabilize, protect, support, or rehabilitate the knee. Typical knee braces and the prescribing of knee braces have several significant limitations and drawbacks. First, after an injury occurs and a medical professional such as a physician recommends the patient wear a knee brace, the medical professional may not see the patient again for several weeks to months after the initial visit. The medical professional may not receive any feedback about range of motion of the joint or strength of the muscles surrounding the joint.

If the patient has been fitted with a brace, the physical therapist may manually adjust the brace, under the guidelines provided by the physician, in order to reduce or increase the allowed motion of the injured joint, or to adjust a brace that has become loose secondary to muscle atrophy, or both. These manual adjustments often lead to errors, as the adjustments are based on the personal judgments of the physical therapist (or medical professional), e.g., the muscles and surrounding tissues may not be of sufficient strength to support the joint.

In some cases, the patient may receive electrical muscle stimulation (EMS) at the start of the physical therapy process to regain the ability to voluntarily contract their muscles before exercising and stretching begins. EMS, also known as neuromuscular electrical stimulation ("NMES"), has been used in therapeutic practice virtually unchanged in the last 30 years. The current use model is to take a target muscle group and provide electrical stimulation to mimic the action potentials normally created from neurological signals into order to activate and elicit an action potential and resultant contraction of the muscle fibers causing the muscle to contract. The electrical stimulation therapy can be enhanced by determining the appropriate level of power and/or duration of the electrical pulse, the pulse width, the phase characteristics (monophasic, biphasic, triphasic, polyphasic, symmetric), frequency, waveform shapes (sinusoidal, square, triangular, trapezoidal, sawtooth, custom), duty cycle, work cycle on/off times, work cycle ramp type. EMS is also used by the therapist (as prescribed by the health care provider) to strengthen muscles which have atrophied. However, the delivery of EMS for muscle strengthening is sub-optimal, as it is usually performed when the patient is with the therapist. Further, a physician (e.g., surgeon) treating a patient often sees the patient several times after the treatment of the injury (e.g., surgery). The physician typically determines the next step in the patient's treatment based on how the patient looks and feels during a visit. The physician, however, usually does not have objective data associated with the patient's injury to help in the physician's assessment of the patient and the next step in the patient's treatment. Specifically, the physician may not be able to obtain accurate range of joint motion or muscle strength. As a result, the physician often determines the patient's next course of treatment based on his or her subjective analysis of the patient at the time of the patient's visit; this analysis may be sub-optimal. In addition to the data being sub-optimal, the time points at which these data are observed is inefficient and sub-optimal. The patient may heal faster or slower than a typical patient and the patient's treatment may be able to be better customized to his/her actual progress.

Thus, there remains a need for a brace system that can provide monitoring of the brace system in use, and provide feedback and adjustment (preferably in real time) of the brace system during a course of therapy.

SUMMARY

Some embodiments of the invention include a system comprising at least one sensor comprising a plurality of electrodes including at least one active electrode and at least one receiving electrode, the at least one sensor configured and arranged to be in physical contact with skin of a patient forming an electrical circuit with control electronics of at least one controller. The electrical circuit is configured and arranged to measure an electrical parameter using the at least one active electrode and at least one receiving electrode, and to form a closed loop electrical muscle stimulation system, where a stimulation current or voltage applied by the sensor onto the skin between the at least one active electrode and at least one receiving electrode is based on at least one program and at least one electrical parameter measured through the at least one active electrode and at least one receiving electrode. In some embodiments, the at least one controller is configured and arranged for (a) applying a sense electrical pulse to the tissue using the at least one sensor, (b) measuring the at least one electrical parameter from the tissue, (c) using at least one of the active electrodes, adjustably applying a stimulation pulse to the tissue based at least in part on the measured electrical parameter, the stimulation being adjustably controlled by the at least one controller to maintain a constant power output to the tissue based at least in part on the at least one electrical parameter, and (d) repeat steps (a)-(c). Some embodiments include a good coupled to at least one computer readable medium configured to store usage data, the usage data relating to the patient's use of the good.

Some embodiments include a computing program, applet or application configured to upload usage data for analysis. In some embodiments, at least one controller is configured and arranged to electromagnetically couple with a mobile computing device using at least a portion of the computing program, applet or application. In some embodiments, at least a portion of the computing program, applet or application is configured and arranged to include at least one user interface on a user's computing device, and the at least one user interface configured to display at least some usage data and to enable control of a parameter of the good.

In some embodiments, at least one controller is configured to update the at least one user interface with at least one of a status of a portion of the good, a position of a portion of the good, and data from the at least one sensor. In some embodiments, at least one user interface comprises a display including an option to scan and synchronize the good with the at least one controller. Some embodiments include at least one user interface comprising a display including an option to scan and synchronize more than one good. In some further embodiments, the at least one user interface comprises a display including an option to activate a wired or wireless link to connect the good with the at least one controller. In other embodiments, the display is configured and arranged to enable the user to set or reconfigure the at least one stimulation pulse.

Some embodiments include a display configurable by the at least a portion of the computing program, applet or application to display one or more parameters related to at least one of stimulation provided by at least a portion of the good, and a range of motion measured by at least a portion of the good. In some embodiments, the display is configurable by the at least a portion of the computing program, applet or application to provide a visual representation of an action of a user wearing at least a portion of the good that is related to at least one of stimulation provided by at least a portion of the good, and a range of motion measured by at least a portion of the good.

Some embodiments include a system where the computing device comprises at least one of a desktop computer, a laptop computer, a digital tablet, a digital assistant, a cellular or smart phone, a smart watch, a wearable activity monitor, a pair of glasses, a camera, a pager, and an internet appliance. In some embodiments, the good comprises a brace assembly. In some embodiments, the brace assembly comprises at least one of a brace, a stay, a sleeve, a band, a sling, a garment, a wrap, and a strap.

In some embodiments, the at least one sensor comprises an accelerometer, a motion sensor, a proximity sensor, an optical sensor, a motion sensor, a gyrometer, a magnetometer, a proximity sensor, a hydration sensor, a force or pressure sensor, a position sensor, a global positioning sensor (GPS), an optical sensor, a magnetic sensor, a magnetometer, an inductive sensor, a capacitive sensor, an eddy current sensor, a resistive sensors, a magneto-resistive sensor, an inductive sensor, an infrared sensor, an inclinometer sensor, a piezoelectric materials or piezoelectric-based sensor, a blood-oxygen sensor, a heart-rate sensor, a laser or ultrasound based sensor, and/or an electromyography type sensor.

Some embodiments include a remote server including a computing program, applet or application configured to initiate or maintain an exchange of the usage data between the good and the server and/or a coupled mobile computing device and the server. In some embodiments, the server is configured as a host to a web portal or coupled to a host server providing the web portal, the web portal configured to access or display the usage data or at least one parameter related to use of at least a portion of the good.

In some embodiments of the invention, the web portal is configurable to create one or more alerts based on at least one user customization criteria related to the usage data, where the criteria can include a level of use of at least a portion of the good by a user, a limit of use of at least a portion of the good by the user, a time of use of at least a portion of the good by the user, a type of use of at least a portion of the good by the user, and/or a behavior of at least a portion of the good while in use by the user.

In some embodiments, the alert comprises at least one of an email, a text or SMS message, a displayed icon, rendered text, a rendered graphic, a categorized or customized alert. In some further embodiments, the at least one user customization criteria includes at least one of a monitoring window, usage rate and/or activity level, one or more specified compliance or rehabilitation goals, compliance rate, range of motion (ROM), and pain values.

DESCRIPTION OF THE DRAWINGS

FIG. 1A is a representation of a knee brace including two sets of geometry with each coupled to one hard segment for the joint according to one embodiment of the invention.

FIG. 1C illustrates range of motion data capture from a brace and brace sensors for motion capture in accordance with accordance with some embodiments of the invention.

FIG. 2F illustrates a full shoulder vest showing an integrated sling in accordance with some embodiments of the invention.

FIG. 2G illustrates a full shoulder vest showing an electrode compression strap in accordance with some embodiments of the invention.

FIG. 2H illustrates a full shoulder vest showing midline vest closure in accordance with some embodiments of the invention.

FIG. 2I illustrates a full shoulder vest showing an electrode access and trapezious compression strap in accordance with some embodiments of the invention.

FIG. 2L illustrates a front view of a half vest in accordance with some embodiments of the invention.

FIGS. 2N and 2P illustrate an air bladder in accordance with some embodiments of the invention.

FIG. 2S illustrates an ankle brace including a plurality of accelerometer sensors in accordance with some embodiments of the invention.

FIG. 3A shows a representation of wireless collection of data including cellular data from a knee brace in accordance with some embodiments of the invention.

FIG. 10 illustrates a sensor assembly for surface edema detection through optical sensing in accordance with some embodiments of the invention.

FIG. 11 illustrates a system for non-narcotic pain relief using electrical stimulation therapy to override pain impulses in accordance with some embodiments of the invention.

FIG. 12 illustrates biological feedback data collection in accordance with some embodiments of the invention.

FIG. 23 illustrates a display of a therapy system control GUI in accordance with some embodiments of the invention.

FIG. 24 illustrates a display of a therapy system control GUI in accordance with some embodiments of the invention.

FIG. 25 illustrates a display of a therapy system control GUI in accordance with some embodiments of the invention.

FIG. 26 illustrates a display of a therapy system control GUI in accordance with some embodiments of the invention.

FIG. 27 illustrates a display of a therapy system control GUI in accordance with some embodiments of the invention.

FIG. 28 illustrates a display of a therapy system control GUI in accordance with some embodiments of the invention.

FIG. 33 illustrates a display of a therapy system control GUI in accordance with some embodiments of the invention.

FIG. 34 illustrates a display of a therapy system control GUI in accordance with some embodiments of the invention.

FIG. 35 illustrates a display of a therapy system control GUI in accordance with some embodiments of the invention.

FIG. 36 illustrates a display of a therapy system control GUI in accordance with some embodiments of the invention.

FIG. 42 illustrates a display of a therapy system control GUI in accordance with some embodiments of the invention.

FIG. 43 illustrates a display of a therapy system control GUI in accordance with some embodiments of the invention.

FIG. 52 illustrates a display of a therapy system control GUI in accordance with some embodiments of the invention.

FIG. 53 illustrates a display of a therapy system control GUI in accordance with some embodiments of the invention.

FIG. 57 illustrates a display of a therapy system control GUI in accordance with some embodiments of the invention.

FIG. 58 illustrates a display of a therapy system control GUI in accordance with some embodiments of the invention.

FIGS. 65A, 65B, and 66-74 illustrate various displays of a therapy system control GUI in accordance with some embodiments of the invention.

FIG. 77 illustrates data categories exchanged between and stored within components of the therapy system of FIG. 75 in accordance with some embodiments of the invention.

FIG. 79 illustrates a customizable panel and alerts window of the provider portal dashboard in accordance with some embodiments of the invention.

FIG. 80 illustrates a provider portal patient list window in accordance with some embodiments of the invention.

FIGS. 83A-83B, and 84A-84B illustrate patient overview printable charts in accordance with some embodiments of the invention.

FIG. 85 illustrates a patient stimulation detail window in accordance with some embodiments of the invention.

FIG. 86 illustrates a patient range-of-motion (ROM) detail window in accordance with some embodiments of the invention.

FIG. 92A illustrates a stimulator session start mobile application screen in accordance with some embodiments of the invention.

FIG. 92B illustrates a pain survey mobile application screen in accordance with some embodiments of the invention.

FIG. 92C illustrates a stimulation treatment mobile application screen in accordance with some embodiments of the invention.

FIGS. 95C and 96A illustrate a range of motion (ROM) measuring mobile application screen in accordance with some embodiments of the invention.

FIG. 96B illustrates a range of motion (ROM) results mobile application screen in accordance with some embodiments of the invention.

FIG. 97A illustrates a settings mobile application screen in accordance with some embodiments of the invention.

FIG. 97B illustrates a profile mobile application screen in accordance with some embodiments of the invention.

FIG. 97C illustrates a set your goals mobile application screen in accordance with some embodiments of the invention.

FIG. 98 illustrates a stimulation help mobile application screen in accordance with some embodiments of the invention.

DETAILED DESCRIPTION

Figure 1B:
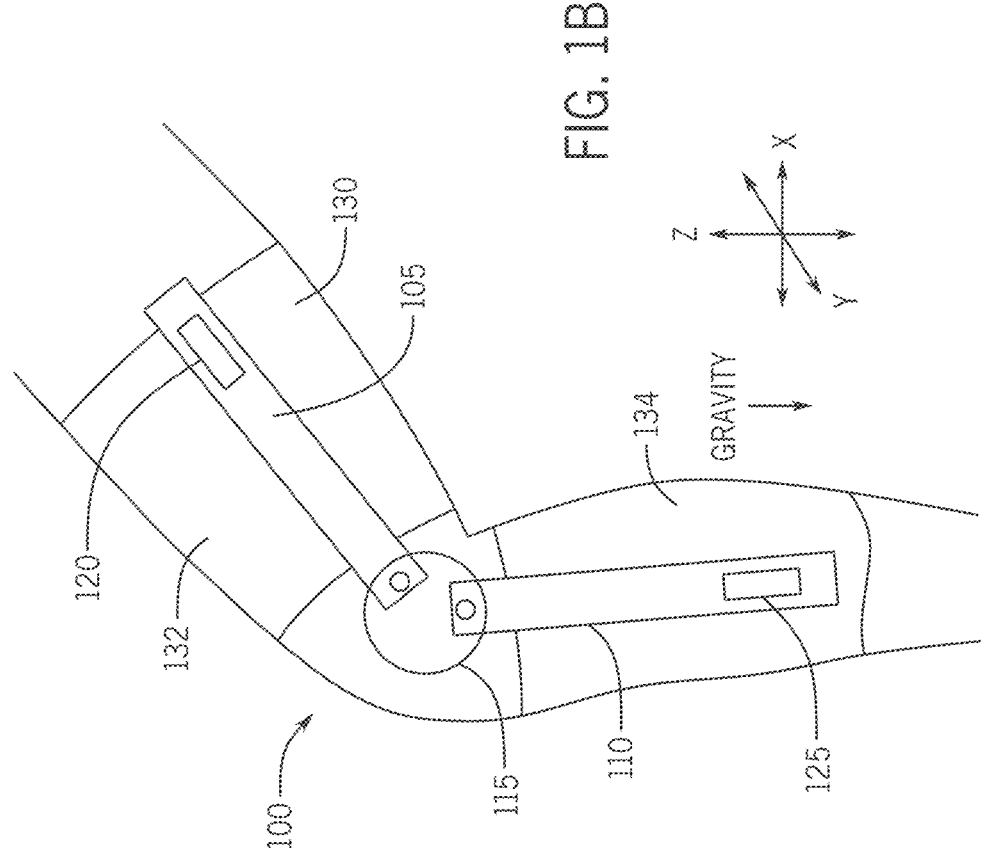
FIG. 1B shows a knee brace including stays and wrap components in accordance with some embodiments of the invention.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives and fall within the scope of embodiments of the invention.

FIG. 1A is a representation of a knee brace 100 with one or more stays coupled to a user (where a user's leg is shown in the representation). In some embodiments, the knee brace 100 can comprise a stay 105 movable coupled to a stay 110 through a pivot region 115. When positioned as such, the knee brace 100 includes two sets of geometry where the stay 105 can be free to move with respect to the stay 110 pivoting and/or moving about the pivot region 115. In some embodiments of the invention, the knee brace 100 and any of the brace systems or assemblies disclosed herein can comprise systems and methods for determining positional data of any component or portion of the brace system. For example, in some embodiments, one or more sensors can be integrated or coupled to at least a portion of the brace system and used to measure or monitor user parameters, track the functional characteristics of the brace system, and/or monitor the environment of the user. In some embodiments, one or more sensors can be integrated with or coupled to at least a portion of the brace system and used to measure absolute or relative position and/or movement of any portion of the brace system while attached to the user. In some embodiments, a wrap can be used without a brace and can fully support the sensors and other components disclosed herein as being coupled to a brace. In some embodiments, one or more sensors can be added to any rigid portion of the brace system. For example, in some embodiments, knee brace 100 can include at least one sensor coupled to at least one of the stays 105, 110. For example, in some embodiments, the knee brace 100 can include a sensor 120 coupled to the stay 105. In some further embodiments, the knee brace 100 can include a sensor 125 coupled to the stay 110. By way of their coupling to the stays 105, 110, sensors 120, 125 can include three-axis movement. Further, depending on the user's movement, the sensors 120, 125 can each move independently of each other in three dimensions. In some embodiments, the stay 105 can be coupled to an upper portion 132 of a wrap 130 for positioning against, proximate or adjacent to the thigh of a user, and the stay 110 can be coupled to a lower portion 134 of a wrap 130 for positioning against, proximate or adjacent to the lower leg of a user. For example, FIG. 1B shows the knee brace 100 including stays 105, 110 and wrap 130 in accordance with some embodiments of the invention. In some embodiments, the wrap 130 can comprise a high-compression and non-slip material that is breathable. In some embodiments, the sensors 120, 125 can measure the position and/or movement and acceleration of any one of the sets of geometry of the brace 100 in any x, y, and/or z-axis. In some embodiments, the sensors 120, 125 can be coupled to an external surface of any portion of the brace 100, including for example to locations within the wrap 130 or stays 105, 110 system shown in FIG. 1B. In some embodiments, sensors can be integrated with the brace 100 by integrating into an internal portion of the brace 100 or by coupling to an external surface of the brace 100.

In some embodiments of the invention, the sensors can include an accelerometer. For example, in some embodiments, sensors can include one or more small solid-state or micro-electromechanical systems (MEMS) accelerometers, gyroscopes, and/or magnetometers can be coupled to one or more portions of the brace system and used to measure/sense position and orientation, acceleration, velocity, vibration or shock along a single or multiple axes. In some embodiments of the invention, the sensors can comprise at least one Hall effect sensor. In some further embodiments, the brace system can include one or more magnets coupled to portions of the brace system that can be used in combination with a magnetic sensor. For example, some embodiments of the invention can comprise at least one Hall effect sensor can be used with one or more magnets to determine motion of at least a portion of the brace system. For example, in some embodiments, the sensor can determine rotation relative to a fixed point on a hinge of the brace system.

Some embodiments of the invention include brace systems or assemblies that can capture range of motion (hereinafter "ROM"). In some embodiments, range of motion data can be used prior to surgery to determine when the patient has recovered enough from an initial injury trauma to undergo surgery, potentially indicating that swelling and soft tissue mobility are at acceptable levels for surgery. In some further embodiments, range of motion data can be used after surgery to determine when the patient has recovered (and therefore can be used to determine the rate of recovery from surgery). For example, FIG. 1C illustrates an example of range of motion data capture from a brace system 140. In some embodiments, positional data can be added to any brace system 140 that has one or more rigid structures to which one or more motion sensors can be coupled. For example, in some embodiments, the brace system 140 can include a stay 145 including a coupled sensor 155, and the stay 150 can include a coupled sensor 160. In some embodiments, the brace sensors 155, 160 can comprise one or more accelerometers, gyroscopes, and/or positional encoders coupled to at least one rigid portion of the brace system. In some embodiments, as either one or both of the stays 145, 150 moves, rotates or pivots about the coupling 170, the sensors 155, 160 can be used to give active feedback to the patient about current range of motion. In some embodiments, range of motion data can be used to continually provide feedback to a user to encourage them to stretch muscles or move a joint during a recovery phase. For example, in some embodiments, tactile feedback can be provided whenever a user has exceeded a specified maximum range of motion. Further, in some embodiments, the brace system 140 can be used to warn a user when they are hitting a range of motion that is not considered to be safe based on the user's stage of recovery. In some other embodiments, the brace system 140 can incorporate dynamic resistance, spring rate, and/or force or damping if high accelerations or ranges of motion are detected to protect the joint. In some embodiments, this can be achieved using magneto-rheological fluids, inertia valve designs, piezoelectric springs/materials, etc. Some embodiments of the invention include kinematic data collection sensors for measuring the position and movement of a brace system 140. Further, in some embodiments, the brace system 140 can include range of motion sensors for any brace system that includes one or more hinge features. In some embodiments, the sensors can include indexing points so that absolute position can be determined. Some embodiments of the invention can include proximity or contact based sensors to determine where set points on a hinge are in proximity of the sensor. In some embodiments, the sensor can be an optical (shadow, self-imaging, or interferometric) sensor, a magnetic sensor, an inductive sensor, a capacitive sensor, an eddy current sensor, a resistive sensor, a magneto-resistive sensor, an inductive sensor, an infrared sensor, an accelerometer sensor, an inclinometer sensor, a piezoelectric sensor, etc.

In some embodiments of the invention, any of the brace systems or assemblies disclosed herein can include one or more controllers. In some embodiments, the controllers can be integrated and/or coupled with stays, joints, pivots or wraps of the brace system. For example, in some embodiments of the invention, control electronics can include a pivotal joint configured to enable a brace of the brace system to flex (e.g., during the patient's flexion and extension). The pivotal joint can include a solenoid and an accelerometer to lock the brace (e.g., after sensing a stress). In one embodiment, the pivotal joint includes a digital positional encoder to determine an absolute position of the joint. The positional encoder can enable adjustment of the physical resistance applied to the joint when the patient moves the joint. The brace control electronics can include a communication module (e.g., transmitter or transceiver or wire) for communicating with the computing device.

Some embodiments include dynamic bracing systems with integrated electrical stimulation that can be configured for assisting in achieving joint flexion and/or extension. In some embodiments, one or more linear springs, torsion springs, and/or cam-based systems can be used to provide dynamic bracing options. In some embodiments, the brace system can comprise a hip brace with integrated electrical stimulation for providing LAMES therapy to targeted tissue in the pelvic region.

Figure 1E:
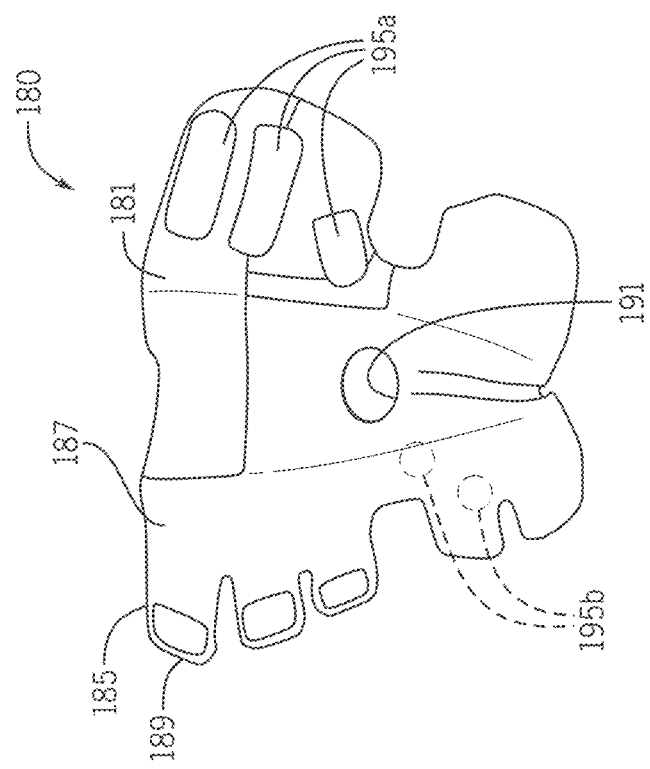
FIG. 1E illustrates a knee wrap in accordance with some embodiments of the invention.
Figure 1D:
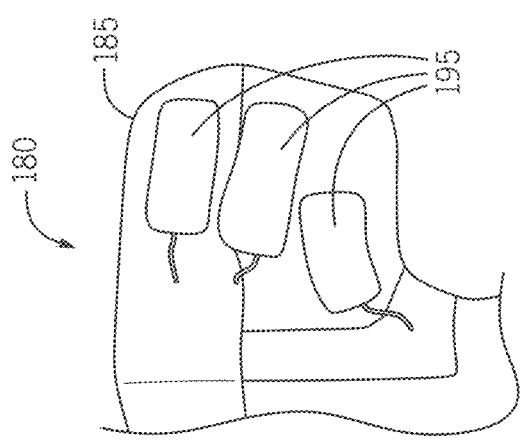
FIG. 1D illustrates part of a knee wrap in accordance with some embodiments of the invention.

In some embodiments, one or more sensors can be integrated into a wearable wrap or garment. For example, FIG. 1D illustrates part of a knee wrap 180, and FIG. 1E illustrates a knee wrap 180 in accordance with some embodiments of the invention. As illustrated, in some embodiments, the knee wrap 180 can comprise a main body wrap 185 that includes a non-slip compression material 187. In some embodiments, this material can assist in preventing movement of the knee wrap 180 when positioned on the wearer through friction and compression force. In some embodiments, the main body wrap 185 can include various extensions 189 to enable wrapping and attachment of the wrap 180 to the knee of the user, and can include various apertures to accommodate various portions of the wearer's body. For example, in some embodiments, the knee wrap 180 can include a popliteal cutout 191 to accommodate the structure and movement in the vicinity of the back of the wearer's knee. Further, in some embodiments, various electronics can be coupled to or integrated with the main body wrap 185. For example, in some embodiments, the main body wrap 185 can include one or more stimulation electrode or electrode pairs 195 such as quadriceps electrodes 195a and/or calf electrodes 195b. Moreover, in some embodiments, the electrode or electrode pairs 195 can be positioned on the inner surface 181 of the wrap 180 to enable contact with the skin of a wearer. As used herein, each stimulating electrode pair can comprise a first electrode structure having a first polarity, and a second electrode structure having a second polarity. The first and second polarities can be different so that the first and second electrode structures function to form an electrode pair capable of electrical stimulation. In some embodiments, the structure of the first electrode can be substantially the same or similar to the second electrode. In other embodiments, the structures of the first and second electrodes can be different. In some embodiments, the electrodes are not limited to conventional electrode structures. For example, in some embodiments, one or more electrodes can comprise conductive material capable of transmitting signals efficiently or, in some embodiments, with significant loss or degradation while still providing sufficient signal strength for the particular application. As used herein, the terms "stimulating electrode" and "stimulating electrode pair" can be used interchangeably.

Figure 1F:
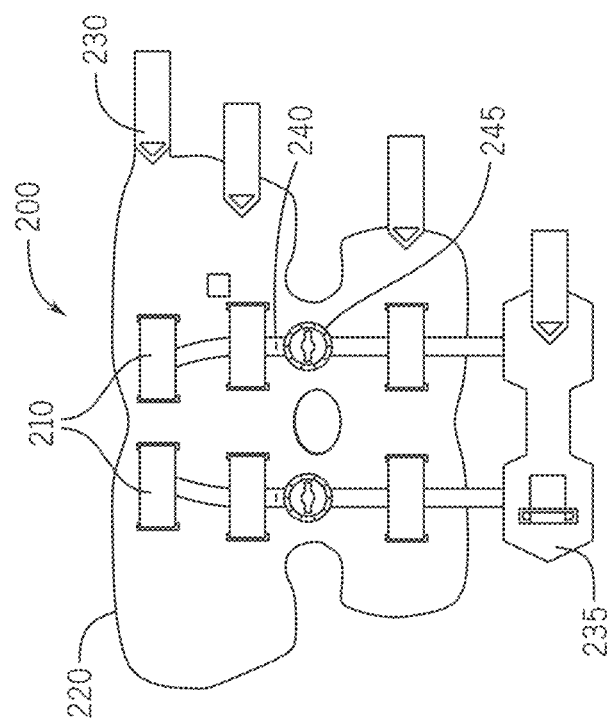
FIG. 1F illustrates a brace system comprising a combined modular orthopedic brace and conductive wrap in accordance with some embodiments of the invention.
Figure 1G:
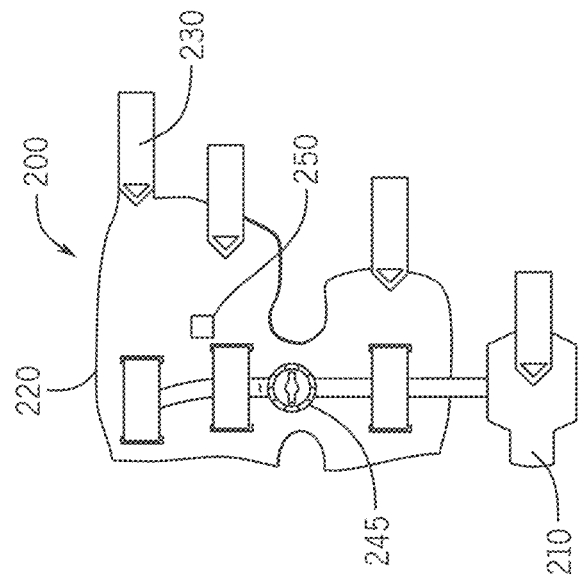
FIG. 1G illustrates a combined modular orthopedic brace and conductive wrap in side view in accordance with some embodiments of the invention.

In some embodiments, one or more brace assemblies can be integrated and/or coupled to a knee wrap to form a combined modular orthopedic brace and conductive wrap. For example, FIG. 1F illustrates a brace system 200 comprising a combined modular orthopedic brace 210 and conductive wrap assembly 220 in accordance with some embodiments of the invention, and FIG. 1G illustrates a combined modular orthopedic brace 210 and conductive wrap assembly 220 in side view in accordance with some embodiments of the invention. In some embodiments of the invention, for positioning, compression, and comfort, the wrap assembly 220 can include brace straps 230, malleolus pads 235, and a slide lock 240. Further, in some embodiments, a stimulation module 250 can be coupled to the assembly 220 to enable application of stimulation therapy. Further, in some embodiments, the assembly can include a dial hinge 245 with ROM stops to enable customized fitting and therapy.

Some embodiments include brace systems or assemblies configured for targeted regions of the wearers body. For example, FIG. 2A illustrates a shoulder sling 300 in accordance with some embodiments of the invention. In some embodiments, the shoulder sling 300 can include a wrap or partial garment 301 that wraps or encloses at least a portion of a wearer's body including at least a shoulder region. In some embodiments, the shoulder sling 300 can include electrodes on the inside that can be used to stimulate the rotator cuff muscles (e.g. supraspinatus, infraspinatus, etc., parascapular muscles, other muscle groups, and/or the shoulder joint). For example, in some embodiments, the shoulder sling 300 can include electrodes 305 coupled or integrated with the sling 300. Further, in some embodiments, the sling 300 can include at least one accelerometer that can measure, monitor, or track movement of the wearer, including movement of the wearer's shoulder with respect to their torso. For example, in some embodiments, the sling 300 can include an accelerometer 310 positioned at one end of the sling 300 near the head or neck end of the wearer. In some further embodiments, the sling 300 can include an accelerometer 310 positioned at one end of the sling 300 near, adjacent or proximate the shoulder or arm of a wearer.

Figure 2B:
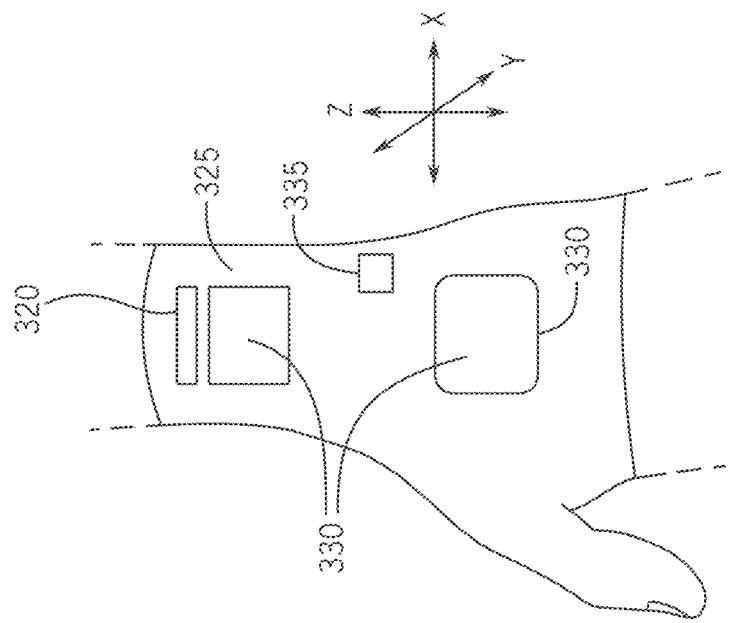
FIG. 2B illustrates a wrist brace including a plurality of sensors in accordance with some embodiments of the invention.
Figure 2A:
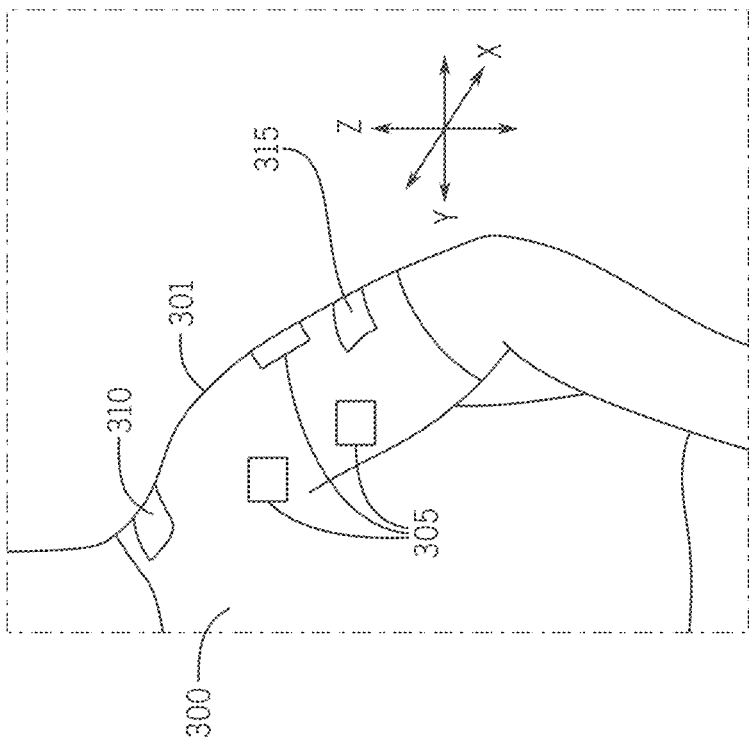
FIG. 2A illustrates a shoulder sling in accordance with some embodiments of the invention.

FIG. 2B illustrates a wrist brace 320 comprising a wrap 325 configured to at least partially wrap or enclose the wrist and/or hand of a wearer. In some embodiments, the wrist brace 320 can include a plurality of sensors 330. In some embodiments, the sensors can include one or more accelerometers. In some further embodiments, other types of sensors can be included such as motion sensors, proximity sensors, optical sensors, magnetic sensors, inductive sensors, capacitive sensors, eddy current sensors, resistive sensors, magneto-resistive sensors, inductive sensors, infrared sensors, inclinometer sensors, piezoelectric materials and piezoelectric-based sensors, etc. In some embodiments, the wrist brace 320 can also include electrodes 335 positioned on the inside of the wrap 325 that can be configured to stimulate distal arm muscle groups and/or the wrist joint(s).

Figure 2D:
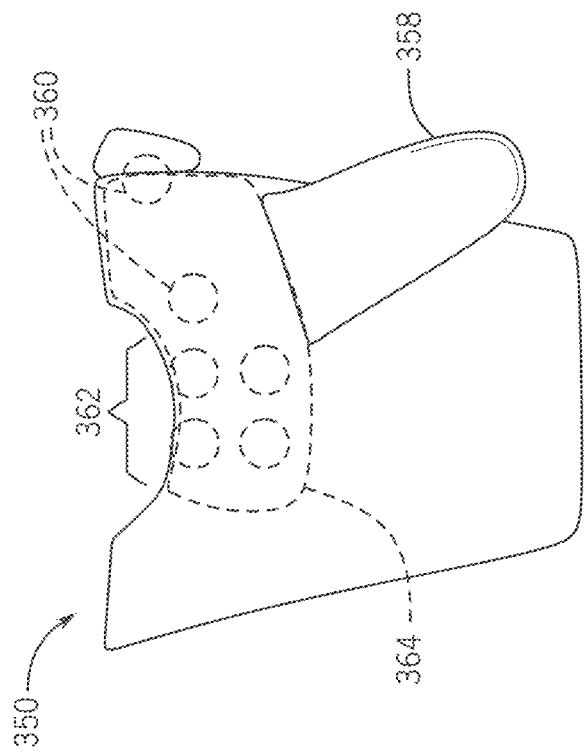
FIG. 2D illustrates a rear view of a full shoulder vest in accordance with some embodiments of the invention.
Figure 2C:
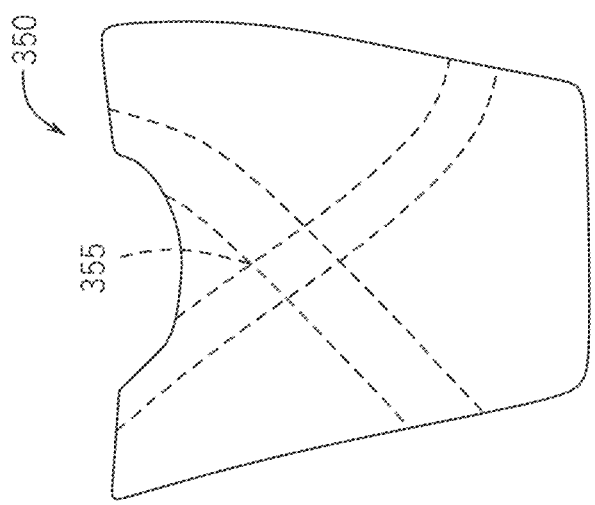
FIG. 2C illustrates a rear view of a full shoulder vest in accordance with some embodiments of the invention.
Figure 2E:
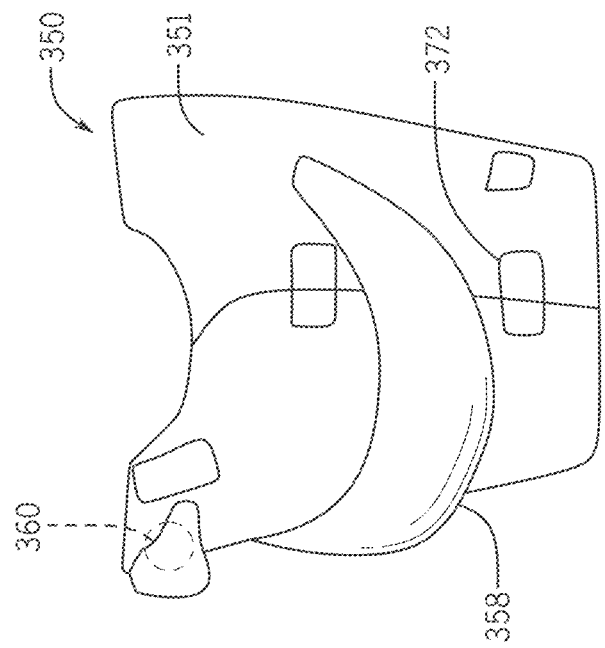
FIG. 2E illustrates a front view of a full shoulder vest in accordance with some embodiments of the invention.

Some embodiments include wraps, braces, or vests that include integrated support and/or tension members. In some embodiments, the tension or support members can function to provide support and/or to impart tension to the wrap, brace, or vest. For example, FIG. 2C illustrates a rear view of a full shoulder vest 350 in accordance with some embodiments of the invention. In some embodiments, the vest 350 can include one or more internal tension members 355. In some embodiments, one or more of the tension members 355 can function to provide a mechanical force to the body of a wearer (e.g., such as the shoulders of a wearer) in order to correct posture. In some embodiments, the vest 350 can include functional electrodes for posture. For example, FIG. 2D illustrates a rear view of the full shoulder vest 350 in accordance with some embodiments of the invention, and FIG. 2E illustrates a front view of the full shoulder vest 350 in accordance with some embodiments of the invention. In some embodiments, the vest 350 can comprise a main vest body 351 that can be closed using one or more closure extensions 372. In some embodiments, the vest 350 can include paraspinal/scapula stabilizer electrodes 362 for posture. Further, some embodiments can include an air bladder pocket 364 including at least one air bladder configured for sleeping support and electrode compression.

FIGS. 2N and 2P illustrate an air bladder 425 that can be used in various embodiments of the invention described herein. In some embodiments, the air bladder 425 can comprise at least one reversibly inflatable bladder 430 coupled to an inflation assembly 433. In some embodiments, the inflation assembly 433 can comprise a detachable inflation tube 440, and a deflation valve 438 coupled to a pump 435 (e.g., a manual pump). In some other embodiments, the vest 350 can also include integrated heat or cold therapy by inserting or attaching a heat or ice pack into a pocket or underneath the shoulder area of the vest, against the patient's skin. Further, some embodiments provide an integrated sling support 358 for the wearer.

Various views of the full shoulder vest 350 shown illustrated on a wearer can be seen in FIGS. 2F-2I. For example, FIG. 2F illustrates a full shoulder vest 350 showing an integrated sling 358 in accordance with some embodiments of the invention. FIG. 2G illustrates a full shoulder vest 350 showing an electrode compression strap 368 and approximate location of a compressed electrode 360, and FIG. 2H illustrates a full shoulder vest 350 showing midline vest closure including closure extensions 372 in accordance with some embodiments of the invention. FIG. 2I illustrates a full shoulder vest 350 showing an electrode access and trapezious compression strap 368a in accordance with some embodiments of the invention. In some embodiments, the strap 368 comprises the strap 368a.

Figure 2K:
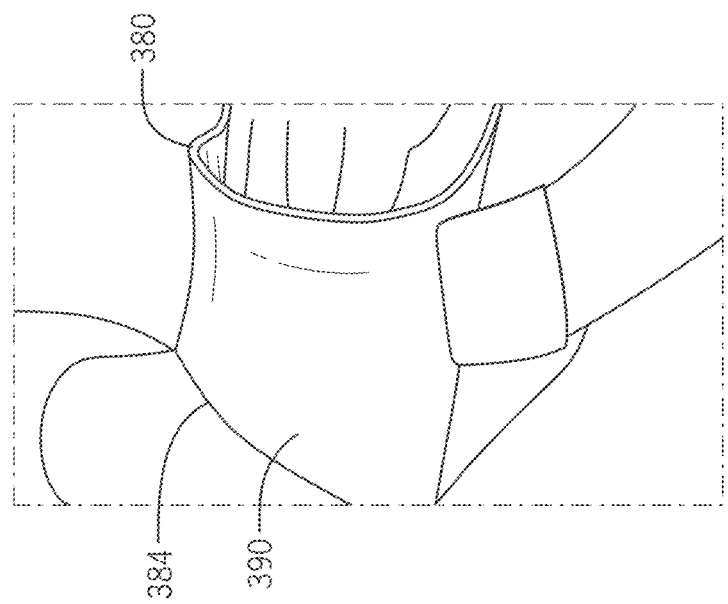
FIG. 2K illustrates a close-up rear view of a half vest in accordance with some embodiments of the invention.
Figure 2J:
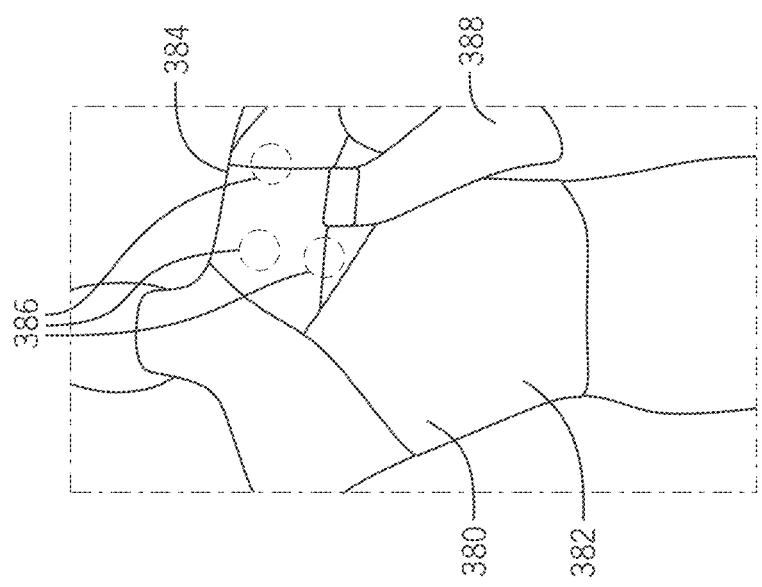
FIG. 2J illustrates a rear view of a half vest in accordance with some embodiments of the invention.
Figure 2M:
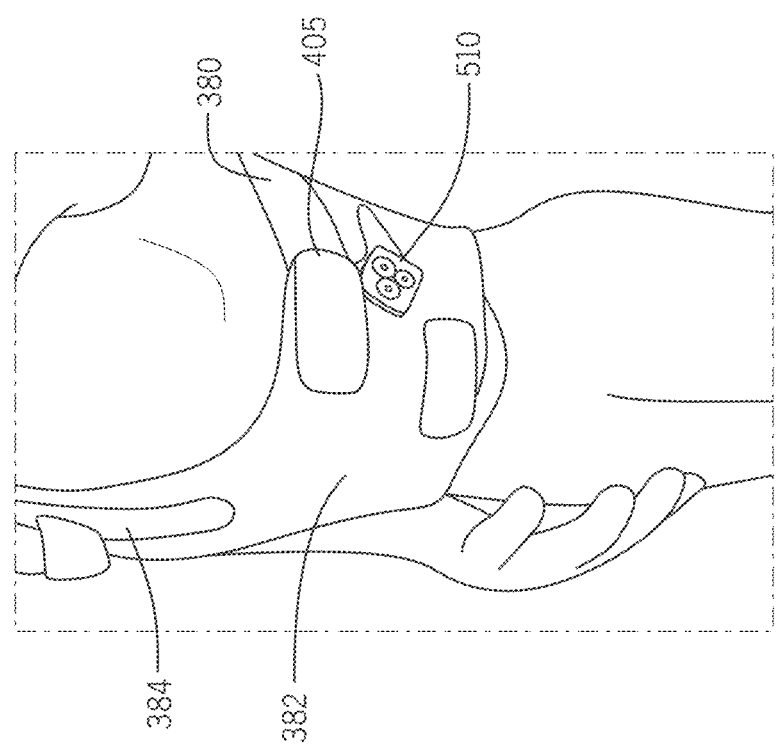
FIG. 2M illustrates a side front perspective view of a half vest in accordance with some embodiments of the invention.

Some embodiments include vests that cover other regions of a wearer's upper body. For example, some embodiments include a vest that covers a partial region (e.g., a left-side, right-side, or central region) of a wearer's torso. For example, FIG. 2J illustrates a rear view of a half vest 380 in accordance with some embodiments of the invention. Further, FIG. 2K illustrates a close-up rear view of the half vest 380, and FIG. 2L illustrates a front view of the half vest 380 in accordance with some embodiments of the invention. Similar to the full vest 350 described earlier, some embodiments can include one or more electrical stimulation electrodes 386. In some embodiments, the half-vest 380 can include one or more air bladder pockets 390. Some embodiments include at least one compression strap. For example, as shown in FIG. 2L, in some embodiments, the half-vest 380 can include a trapezius compression strap 384 coupled to a torso wrap 382. The half-vest 380 can also include an integrated sling 388 coupled to the torso wrap 382. Some embodiments include at least one electrode access opening 400. Further, some embodiments can include at least one strap or pocket configured to hold or support a portion of the wearer's body. For example, some embodiments include an adjustable quarterback pocket 395 coupled to or integrated with the half-vest 380. Further, FIG. 2M illustrates a side front perspective view of a half vest 380 in accordance with some embodiments of the invention. In some embodiments, the vest 380 can comprise at least one strap or fastener 405 that can be used by a wearer to secure the vest, tighten the vest, loosen the vest, or remove the vest.

Further, in some embodiments, the vest can include at least one stimulation module 410. In some embodiments, one or more stimulation modules 410 can be integrated into the vest 380. In some further embodiments, one or more stimulation modules 410 can be reversibly secured to the vest using a variety of attachment mechanisms including, but not limited to fasteners, clips, Velcro, buttons, snap-fit or snap on assemblies, etc.

Figure 2Q:
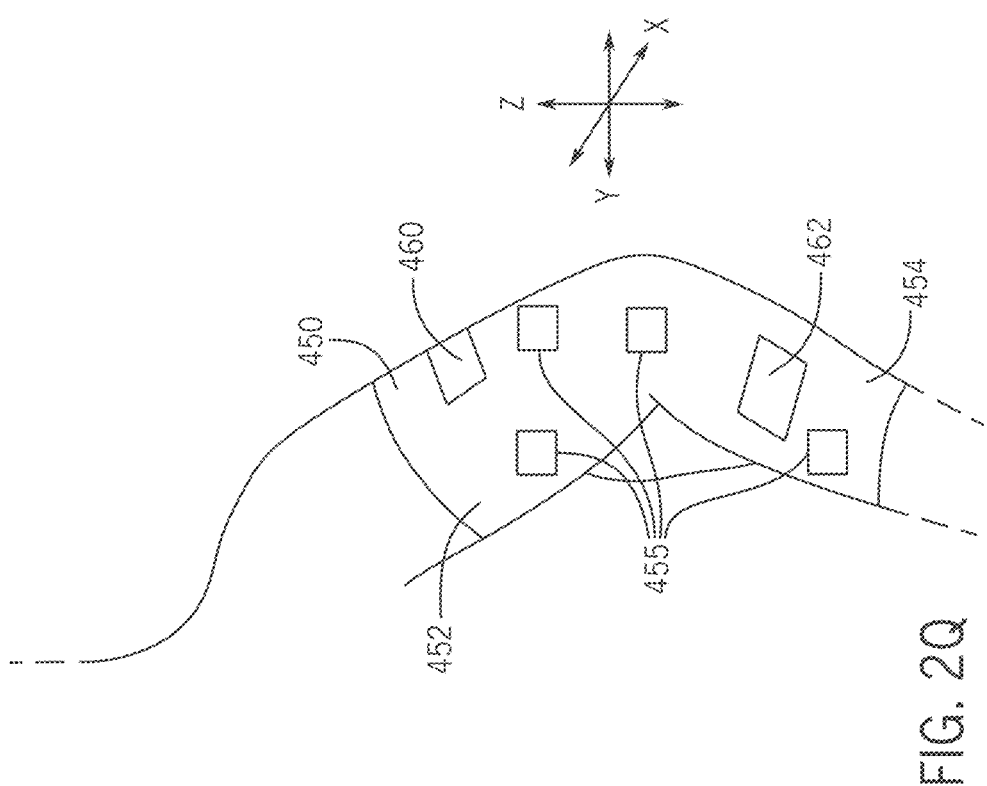
FIG. 2Q illustrates an arm brace including a plurality of accelerometer sensors in accordance with some embodiments of the invention.

FIG. 2Q illustrates an elbow brace 450 including a plurality of accelerometer sensors in accordance with some embodiments of the invention. In some embodiments, the elbow brace can include electrodes 455 on the inside of the brace 450 that can be used to stimulate proximal arm muscle groups, distal arm muscle groups, and/or the elbow joint(s). In some embodiments, the electrodes 455 can be positioned in the upper arm portion 452 of the brace 450 and/or the lower arm portion 454 of the brace 450. In some embodiments, the brace 450 can include an accelerometer 460 integrated or coupled to the upper arm portion 452, and an accelerometer 462 integrated or coupled to the lower arm portion 454.

Figure 2R:
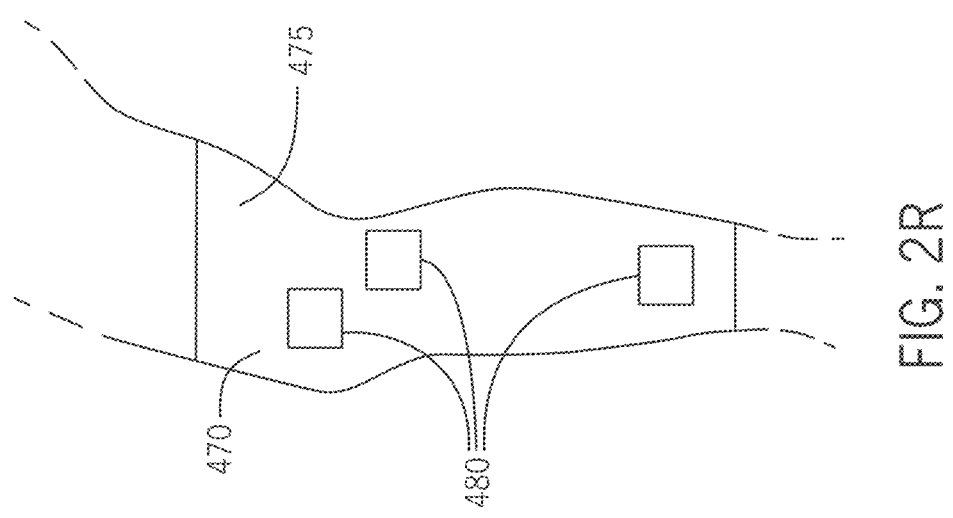
FIG. 2R illustrates a calf brace 470 including a plurality of accelerometer sensors in accordance with some embodiments of the invention.

FIG. 2R illustrates a calf brace 470 including a plurality of accelerometer sensors in accordance with some embodiments of the invention. In some embodiments, the calf brace 470 can comprise a wrap 475 that can also include sensors and/or electrodes 480 on the inside of the brace 470 that can be used to stimulate distal leg muscle groups, and/or the knee joint(s), and/or ankle joint(s). In some embodiments, the electrodes 480 can be energized with electrical stimulation to stimulate the calf muscle groups to induce an electrical or mechanical pumping effect that pumps bodily fluids such as blood to reduce edema and prevent deep vein thrombosis (DVT).

FIG. 2S illustrates an ankle brace 500 comprising a wrap 501 including a plurality of accelerometer sensors in accordance with some embodiments of the invention. In some embodiments, the ankle brace 500 can include electrodes 505 on the inside of the wrap 501 that can be used to stimulate distal leg muscle groups, and/or the ankle joint(s), and/or foot joint(s). The brace 500 can include an accelerometer 510 in a leg portion 503 of the wrap 501. In other embodiments, the brace 500 can include an accelerometer 515 in a foot portion 504 of the wrap 501.

Figure 2T:
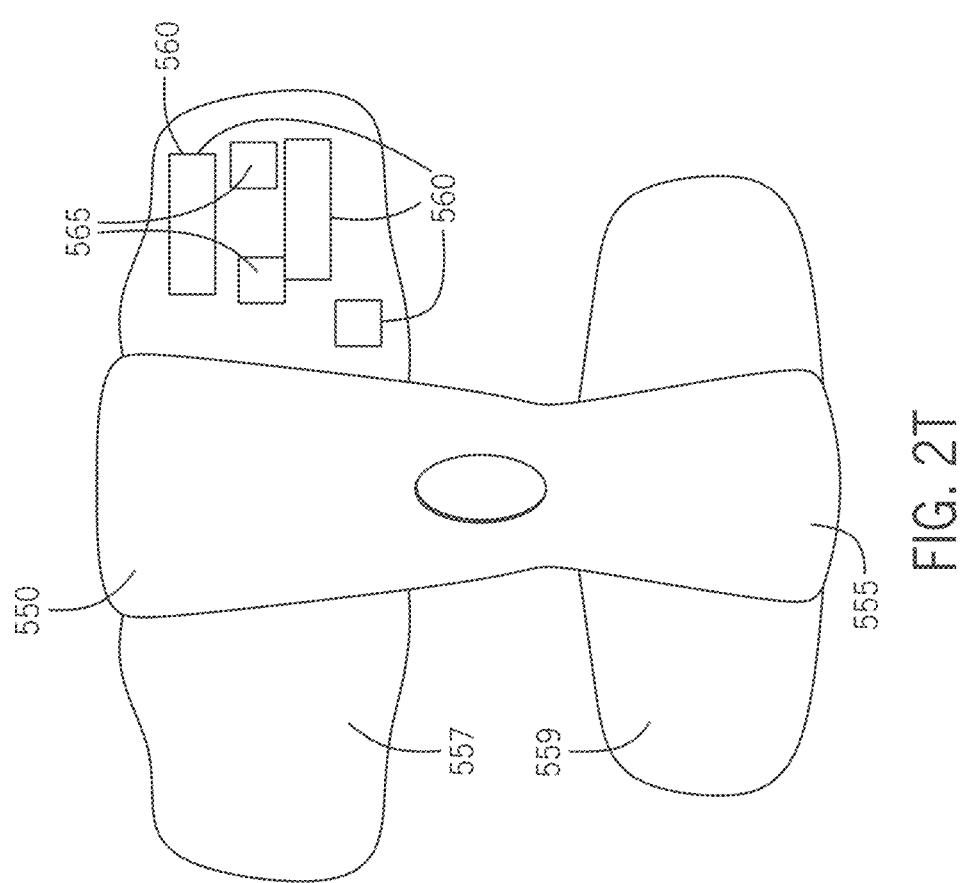
FIG. 2T illustrates an inner region of a brace showing two contact points used to determine if the brace is being worn by a human in accordance with some embodiments of the invention.

In some further embodiments, one or more sensors can be coupled to various inner regions of the brace system. For example, FIG. 2T illustrates an inner region of a brace showing two sensors positioned within the inner region of the brace system. In some embodiments, portions of the sensors can comprise contact points that are located and configured at the outer surface of the inner region of the brace system. In some embodiments, the sensors can comprise human contact sensors that can be used to determine if the brace is being worn by a human. In some embodiments, measurements from the sensors can be used to provide patient compliance data where usage of the brace system is monitored and logged. In some other embodiments, the sensors can be used to monitor if the brace system is correctly positioned on the user. For example, in some embodiments, the brace 550 can comprise a main body portion 555 and upper and lower strap portions 557, 559. In some embodiments, the hip brace 550 can include electrodes on the inside of one of the strap portions 557, 559 that can be used to stimulate muscle groups. For example, in some embodiments, strap portion 557 can include a plurality of electrodes 560 positioned on various regions of the strap portion 557. Further, in some embodiments, either or both of the strap portions 557, 559 can include at least one contact sensor. For example, in some embodiments, the strap portion 557 can include at least one integrated or coupled contact sensor 565.

Figure 2X:
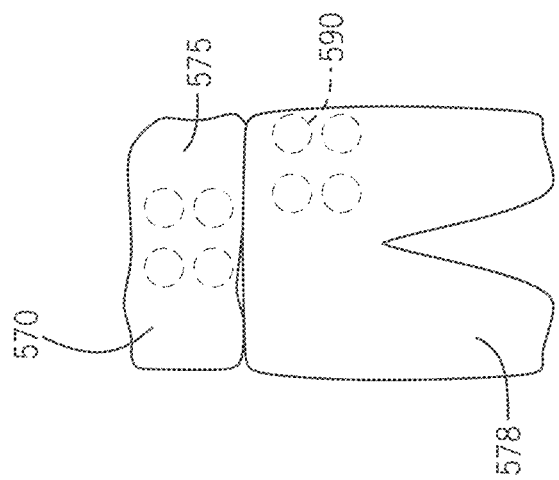
FIG. 2X illustrates a rear view of a hip brace assembly with integrated sensors in accordance with some embodiments of the invention.
Figure 2W:
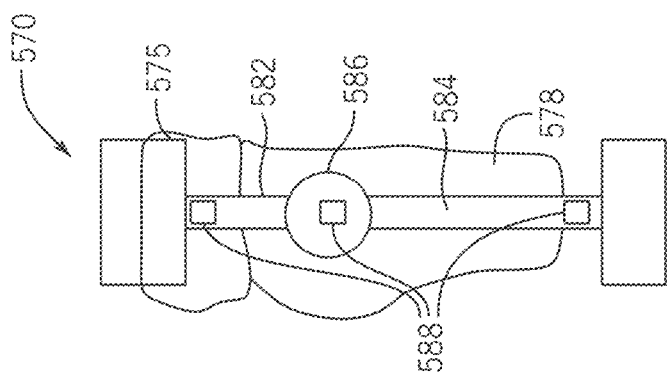
FIG. 2W illustrates a side view of a hip brace assembly with integrated sensors in accordance with some embodiments of the invention.
Figure 2V:
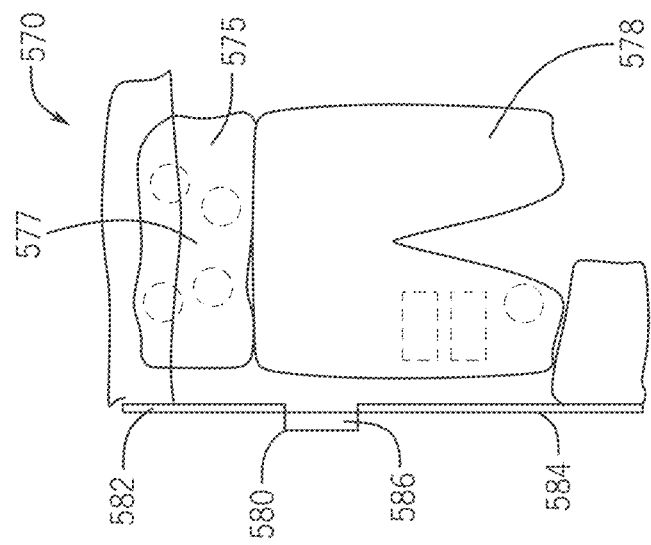
FIG. 2V illustrates a front view of a hip brace assembly with integrated sensors in accordance with some embodiments of the invention.

Some embodiments of the invention can include wraps, braces and/or vest suitable for the hip region of a wearer. As with the aforementioned wraps, braces, and vest, some embodiments of a hip device can include various integrated or coupled sensors, electrodes, supports and/or tension members. For example, FIG. 2V illustrates a front view of a hip brace assembly 570 with integrated sensors in accordance with some embodiments of the invention. FIG. 2W illustrates a side view of the hip brace assembly 570. Further, FIG. 2X illustrates a rear view of the hip brace assembly 570 with integrated sensors in accordance with some embodiments of the invention. In some embodiments, the hip brace assembly 570 can comprise an abdominal/back belt 575, a compressive short conductive garment 578, and a brace bar assembly 580. In some embodiments, the brace bar assembly 580 can comprise an upper bar 582 and lower bar 584 coupled via a brace hinge 586. In some embodiments, the hip brace assembly 570 may also include electrodes on the inside that can be used to stimulate proximal leg muscle groups, abductors, adductors, gluteal muscle groups and/or the hip joint. For example, in some embodiments, the hip brace assembly 570 can include abdominal electrodes 577 integrated or coupled into the abdominal/back belt 575 used to stimulate abdominal muscle groups, lower back muscle groups, and/or the back joint(s), and/or pelvic joint(s), and/or hip joint. In other embodiments, the compressive short conductive garment 578 can include gluteal muscle groups stimulating electrodes 590.

In some further embodiments of the invention, the measurement of position, movement, and/or acceleration of a portion of a brace assembly can be used to determine track the position and movement of the user. For example, in some embodiments, the assembly can be used to monitor a user to determine how much time the user spends in an upright position and/or in a supine position. In some embodiments, acceleration data from the brace system can be computed on a per limb basis which can be tallied as a running average. Further, in some embodiments, this average acceleration value can be used to directly correlate to the amount the patient is moving the limb, and can be used as key to identify a decrease in range of motion. For example, the lower the number, the lower the general level of movement of the user in total. In some embodiments, if the maximum flexion numbers received from the sensors are high and the average acceleration value is very low, the user is sitting in place flexing a limb. However, if the average acceleration value number is very high, and the maximum flexion numbers are low, the user is moving around, but they are keeping the braced limb in a locked position with no movement at the joint. In some other embodiments, using any of the integrated or coupled sensors or accelerometers disclosed herein, free fall incidents can be determined by the one or more sensors of a brace assembly and reported to computer system (e.g., such as a coupled computer or server or backend system or mobile device as disclosed herein). In some embodiments, the brace system can record the free falls to denote any time the brace (and the user) have fallen. Further, in some embodiments, the brace system can determine the height of the fall based on the duration and the rate of acceleration. In some embodiments, the brace system can determine if the user began to fall and subsequently caught themselves. Moreover, in some embodiments, the backend system can create and/or calendar a follow up requirement for a medical professional to determine if the fall did any damage. Referring to FIG. 2W, in some embodiments, the assembly 570 can include sensors/accelerometers 588 integrated and/or coupled with one or more portions of the brace bar assembly 580 including for example with the upper bar 582 and/or the lower bar 584 and/or the brace hinge 586.

In some further embodiments of the invention, patient compliance data obtained from the accumulated measurements from the sensors can be stored on a database (e.g., in a back-end computer system) and can be used by, for example, physicians or medical professionals to retrieve, review, and/or analyze the data from the brace system. In some embodiments, the physicians may utilize the data from the brace in the physician's analysis or recommendations to the patient. Further, physicians may utilize the data from the brace system of one patient in recommendations to other patients with similar conditions or injuries. For example, if the physician tells a patient recovering from an ACL reconstructive surgery to execute program 1 for the first week, and to execute program 2 for the second week, and if the physician sees significant improvements in the patient's strength in the patient's knee due to these programs, the physician will likely tell another patient recovering from a similar surgery to execute the same programs during the same time periods. In some embodiments, the physician can have the programs for the second patient updated remotely via a wired or wireless connection to the Internet or a private network. The physician can then obtain data from both patients to see how they are responding to the brace system and the programs being executed by the brace system.

Figure 2Z:
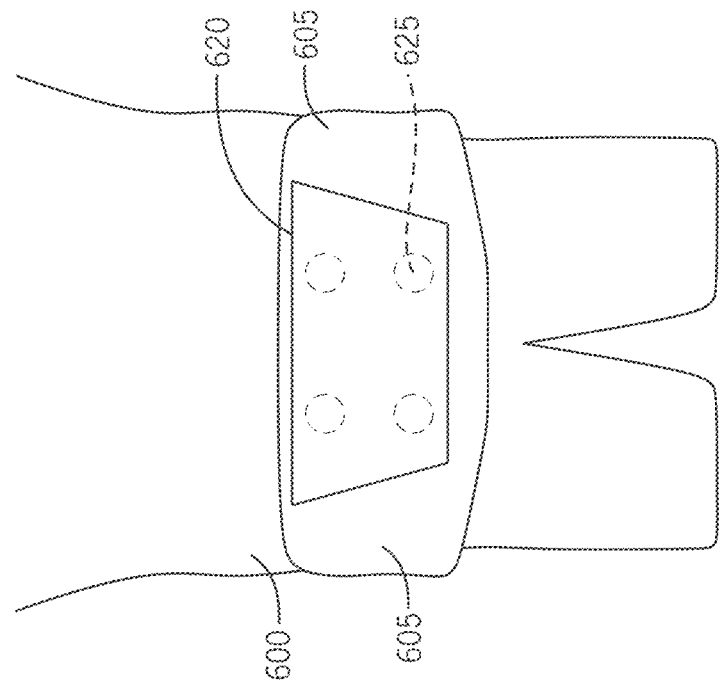
FIG. 2Z illustrates a rear view of an abdominal/back device with integrated sensors in accordance with some embodiments of the invention.
Figure 2Y:
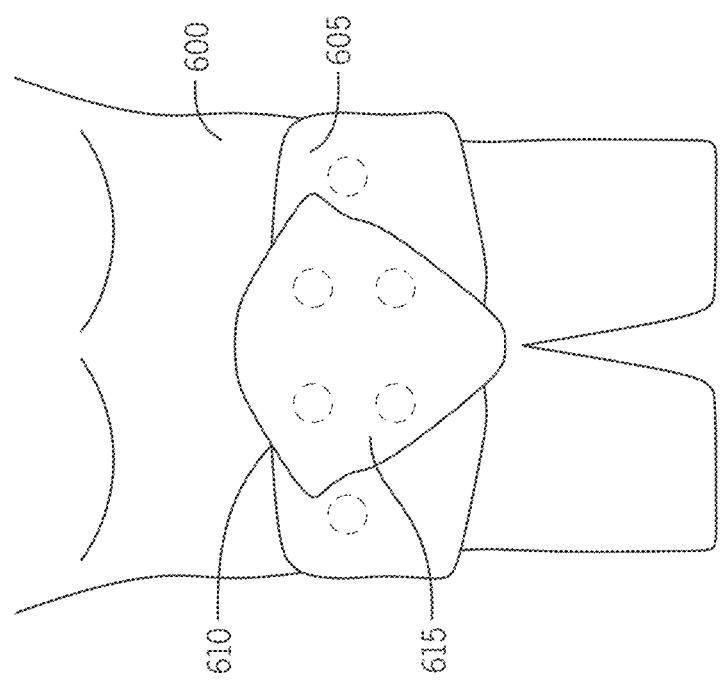
FIG. 2Y illustrates a front view of an abdominal/back device with integrated sensors in accordance with some embodiments of the invention.

Some embodiments of the invention can include wraps, braces and/or vest suitable for an abdominal/back region of a wearer. As with the aforementioned wraps, braces, and vest, some embodiments of the abdominal/back device can include various integrated or coupled sensors, electrodes, supports and/or tension members. For example, FIG. 2Y illustrates a front view of a abdominal/back device 600 with integrated sensors in accordance with some embodiments of the invention, and FIG. 2Z illustrates a rear view of abdominal/back device 600 with integrated sensors in accordance with some embodiments of the invention. Some embodiments can include a main body 605 with a coupled or integrated brace panel 610. In some embodiments, abdominal electrodes 615 can be coupled or integrated with the abdominal/back device 600. Further, some embodiments include an abdominal/back belt brace 620 coupled to the main body 605. In some embodiments, the abdominal/back belt brace 620 can include one or more coupled or integrated back electrodes 625. Further, similar to other embodiments described earlier, some embodiments of the abdominal/back device 620 can include one or more optional air bladders for electrode compression and/or back support.

In some embodiments of the invention, the various electronic components can be integrated into one or more modules of a brace system, and the modules can be combined and recombined into various configurations. For example, in some embodiments, some brace systems or assemblies can comprise a set of modules each of which has a distinct function, and the combination of which creates a general LAMES platform with different user interfaces and/or different sensors for data collection. In some embodiments, this platform can comprise at least one stimulation system, one or more sensor systems, and at least one display system. Further, in some embodiments, the brace system can be controlled by and/or transfer data through a controller in a wired or wireless fashion. For example, in some embodiments of the invention, any of the brace systems or assemblies described herein can be configured to transmit and/or receive information wirelessly. For example, FIG. 3A shows a representation of wireless brace system 630 configurable for wireless collection of data from a knee brace assembly 670 including data communicated through a cellular 650 and/or a WiFi network 655 to a coupled or integrated controller 675 comprising a wireless antenna 675a. In some embodiments, one or more portions of the knee brace assembly 670 can include one or more sensors (e.g., an accelerometer or other sensor as discussed earlier) such as sensor 681 coupled to stay 682 and/or sensor 683 coupled to stay 684 that can be coupled to the controller 675 to enable wireless transmission of data from and/or to the controller 676 and/or sensors 681, 683. In some embodiments, a graphical user interface (GUI) 640 can be used to control and/or monitor the function of various functional aspects of the wireless brace system 630, including any of the components in the system 630. In some embodiments, the controller 675 can comprise a rechargeable power and control unit configured for stimulation and collection of sensor data.

In some embodiments, the controller 675 can manage sensing and/or stimulation of a patient wearing a brace system or garment (e.g., such as wireless brace system 630). In some embodiments of the invention, the controller 675 can configured (a) apply at least one stimulation sense pulse to the patient's tissue using at least one sensor and/or electrode, (b) measure at least one electrical parameter from the patient's tissue related to power dissipation of the sense pulse in the tissue, (c) adjustably apply the at least one stimulation pulse to the patient's tissue based at least in part on the measured power dissipation. In some embodiments, the at least one stimulation pulse can be adjustably controlled by the at least one controller to maintain a constant power output to the patient's tissue based at least in part on the at least one electrical parameter. In some embodiments, the steps (a) through (c) can be repeated at least once.

Figure 3B:
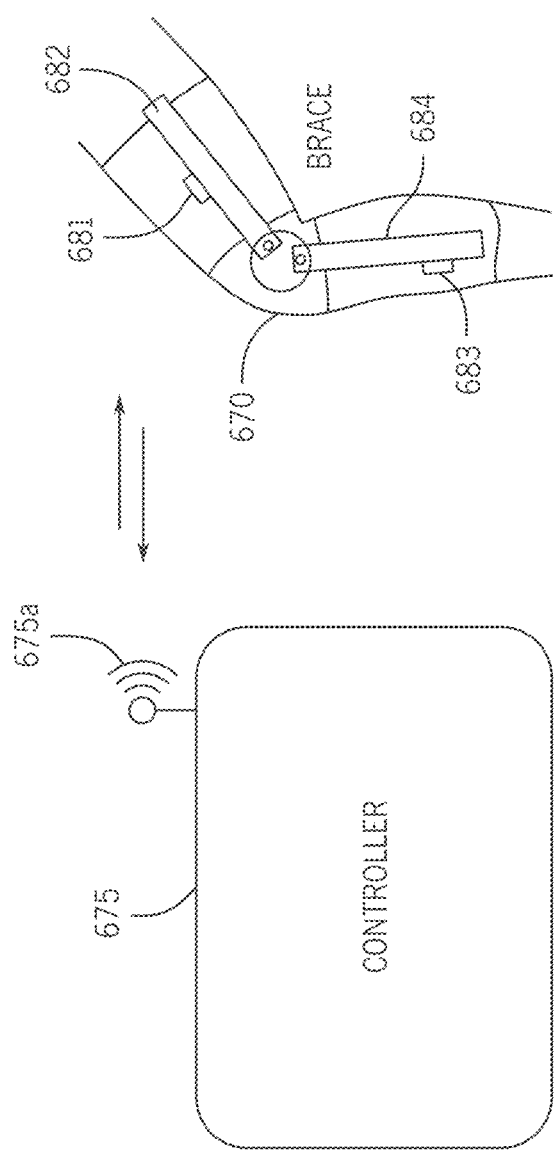
FIG. 3B depicts wireless data transfer data between a knee brace and a controller in accordance with some embodiments of the invention.

FIG. 3B depicts wireless data transfer data between the knee brace assembly 670 and the controller 675 in accordance with some embodiments of the invention. In some embodiments, a wireless RF transmission from the brace system 670 can be of sufficient power to enable reliable operation and transmission of data from the brace system with adequate bandwidth while minimizing tissue propagation characteristics and specific absorption rate (to avoid tissue heating) and reduce exposure of the user to near-field and far-field RF transmission. In some embodiments, the brace system 670 can be configured to transmit and/or receive an RF transmission including, but not limited to, a zero generation wireless signal, a first generation wireless signal, a second generation wireless signal, a third generation wireless signal, a fourth generation wireless signal, a fifth generation wireless signal, any global positioning satellite signal (such as "GPS" or "GLONASS"), an industrial, scientific, and medical (ISM) frequency bands (e.g., 2400-2493.5 MHz), a Bluetooth® wireless signal (such as IEEE 802.15.4 Bluetooth® class II), RFID electromagnetic radiation, a WiFi wireless signal, a two-way radio RF signal, a UHF or VHF signal (such as a citizen's band radio signal or other radio signal emitted from a 'walkie-talkie' type device), high-speed and millimeter wave signals, and a near-field wireless signal. Bluetooth® is a computing and telecommunications industry specification that details how mobile devices can easily interconnect with each other and with non-mobile devices using a short-range wireless connection. Bluetooth® is a registered trademark of Bluetooth SIG, Inc.

In some embodiments, the controller 675 can comprise a computer system or device. In some embodiments, the brace system can be configured to communicate (e.g., wirelessly or via a wired connection) with a computing device that may perform the function of the controller 675. Examples of the computing device include, but are not limited to, personal computers, digital assistants, personal digital assistants, mobile phones, wearable technology devices (e.g. smart watches, activity monitors, heart rate monitors, glasses, cameras, etc.), smartphones, tablets, or laptop computers. In some embodiments, the computing device can be the patient's device or a device associated with a medical professional. Both types of devices can enable the medical professional to retrieve and analyze data transmitted from the brace system. In one embodiment, this data is transmitted in real-time, so that the medical professional can analyze the data and/or adjust the brace at any time. For example, in some embodiments, the patient can access data using a mobile application on his device. In some further embodiments, a physician and/or therapist can access data via a web portal. In some embodiments, any data accessed through from any of the brace systems described herein, including any data collected or channel through a controller such as controller 675 can be secured using one or more conventional encryption methodologies. In some embodiments, the protocols and method for data transfer as described are HIPAA compliant.

Figure 4:
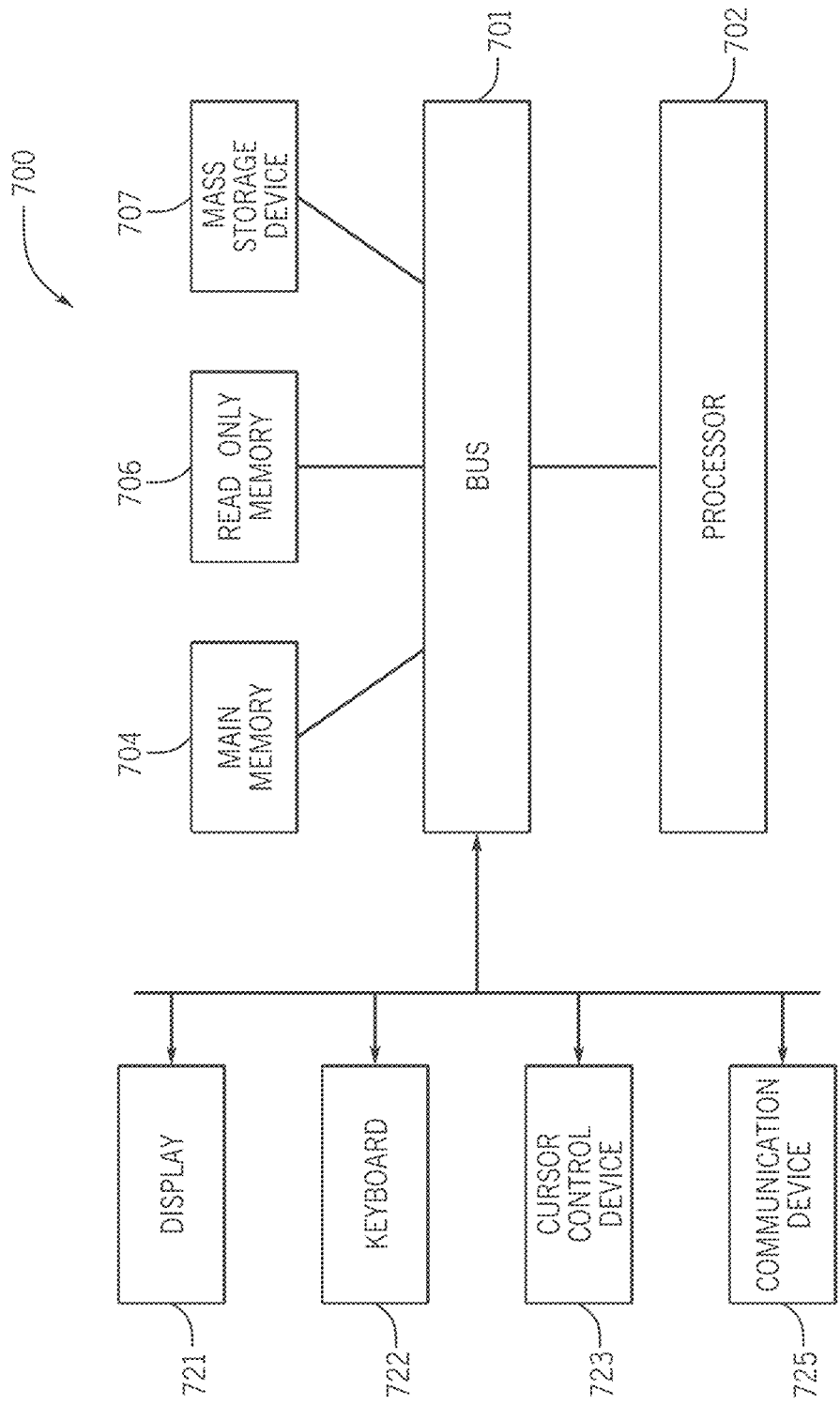
FIG. 4 illustrates a computer system controller in accordance with some embodiments of the invention.

Referring to FIG. 4, in some embodiments, any of the brace systems or assemblies described herein can electronically couple with a computer system 700 that can be configured to transfer data from and/or to the brace system. Further, in some embodiments, the brace system can also comprise brace control electronics that can be configured to provide the LAMES via a program selected from a plurality of programs. In at least one embodiment of the invention, the brace control electronics can be configured to receive, via a receiver, a selection of the program (e.g., from the patient, from a medical professional, etc.). In one embodiment, the medical professional can prevent patient control of the brace (e.g., for a period of time). Further, as illustrated in FIGS. 3A-3B, in some embodiments, a brace system (such as brace system 670) can communicate with the computer system 700 using a controller, such as controller 675. In some embodiments, the controller 675 can function as an interne transceiver coordinating and routing data between the brace and the computer system 700. In some embodiments, the system 700 comprises the controller 675. In some embodiments of the invention, the computer system 700 can be a local computer system (e.g., a computer system within the user's home) that can be configured to receive and/or send information to the brace system 670. In some embodiments, the computer system 700 can include a bus 701 for communicating information between the components in the computer system 700. Further, in some embodiments, at least one processor 702 can be coupled with the bus 701 for executing software code, or instructions, and processing information. In some embodiments of the invention, the computer system 700 further compromises a main memory 704, which can be implemented using random access memory (RAM) and/or other random memory storage devices. In some embodiments, the main memory 704 can be coupled to the bus 701 for storing information and instructions to be executed by the processor 702. Further, in some embodiments, the main memory 704 also can be used for storing temporary variables, NMES program parameters, or other intermediate information during the execution of instructions by the processor 702. In some embodiments, the computer system 700 can also include a read only memory (ROM) and/or other static storage device coupled to the bus 701 for storing static information and instructions for the processor 702. In some embodiments of the invention, the computer system 700 can include one or more peripheral components enabling user interaction with the system 700. For example, in some embodiments, the system 700 can include a cursor control device 723, such as a conventional mouse, touch mouse, trackball, track pad, or other type of cursor direction keys for communicating direction information and command selection to the processor 702 and for controlling movement of a cursor on the display 721. Further, the system 700 can also include at least one keyboard 722 for data input, and facilitation of command and control of the various aspects of the system 700, and at least one communication device 725 operatively coupled to the processor 702 via the bus 701.

Figure 5:
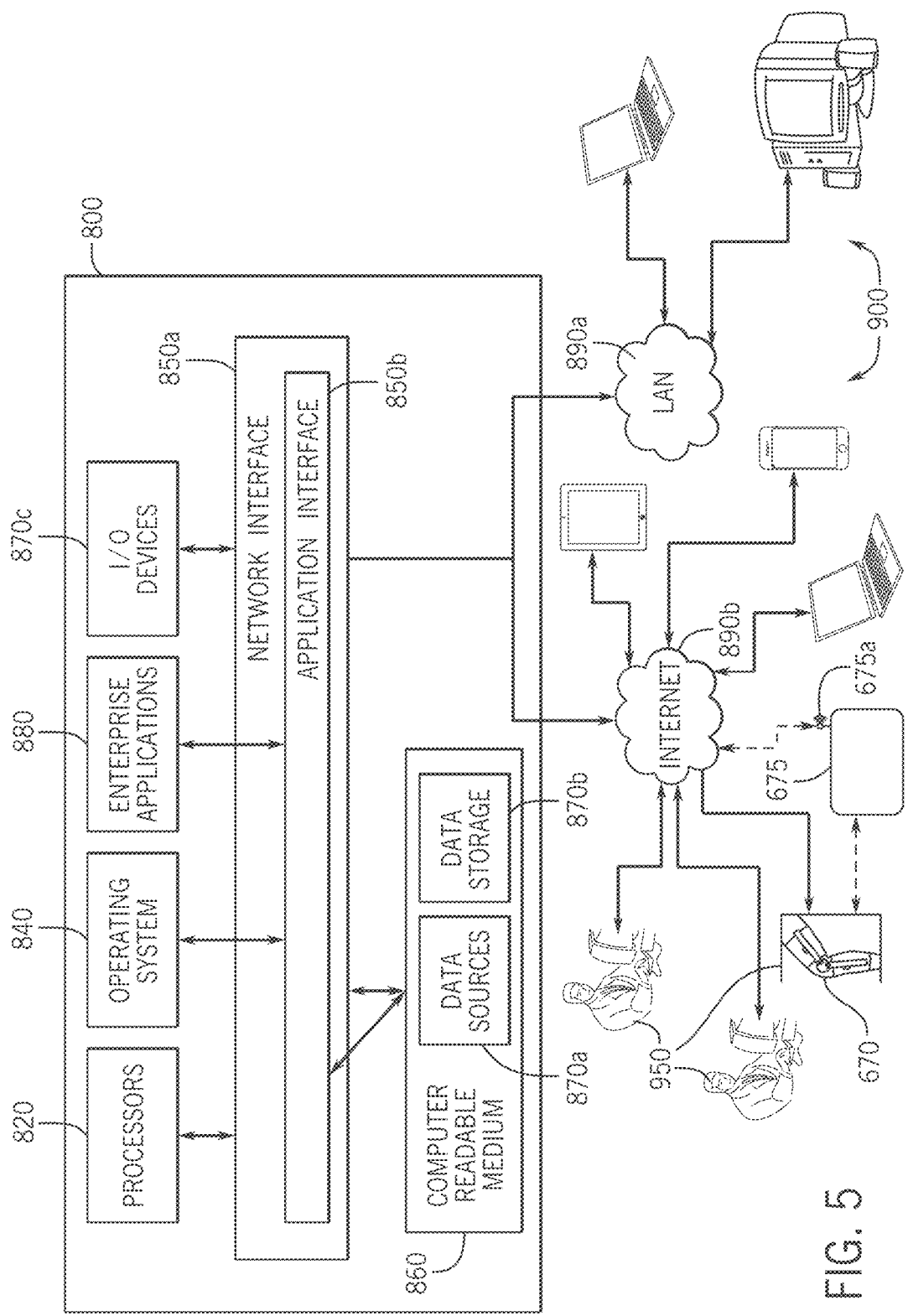
FIG. 5 illustrates a computer system including a backend server in accordance with some embodiments of the invention.

In some embodiments, any of the brace systems or assemblies described herein (including the brace system 670) can be coupled to and transfer data from and/or to a computer system that is configured to receive and/or send information to the brace system and any coupled computer system. Turning to FIG. 5, in some embodiments, a computer system 800 can comprise a backend system that can be used as a host computer for storing information measured and sent by the brace system. In some embodiments of the invention, the information can be received and/or sent between the brace system and the computer system 800 using the computer system 700 (i.e., a local computer system and/or controller that can be configured to receive and/or send information to the brace system locally). In some further embodiments, the information can be received and/or sent between the brace system and the computer system 800 directly (e.g., using a cellular wireless transmission). Further, in some embodiments, the brace can communicate with the computer system 800 and the computer system 700 using a controller, such as controller 100. In some embodiments, the controller can function as an internet transceiver coordinating and routing data between the brace and the computer systems 700, 800.

In some embodiments of the invention, the system 800 can include at least one computing device, including at least one or more processors 820. In some embodiments, some processors 820 can include processors 820 residing in one or more conventional server platforms. In some embodiments, the system 800 can include a network interface 850a and an application interface 850b coupled to at least one processors 820 capable of running at least one operating system 840. Further, the system 800 can include the network interface 850a and the application interface 850b coupled to at least one processor 820 capable of processing one or more of the software modules 880 (e.g., one or more enterprise applications). In some embodiments, the software modules 880 can comprise a server-based software platform. In some embodiments, the system 800 can also include at least one computer readable medium 860. In some embodiments, at least one computer readable medium 860 can be coupled to at least one data storage device 870*b*, and/or at least one data source 870*a*, and/or at least one input/output device 870*c*.

In some embodiments, the invention can also be embodied as computer readable code on a computer readable medium 860. In some embodiments, the computer readable medium 860 can be any data storage device that can store data, which can thereafter be read by a computer system. Examples of the computer readable medium 860 can include hard drives, network attached storage, read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor.

In some embodiments, the computer readable medium 860 can also be distributed over a conventional computer network. For example, in some embodiments, the computer readable medium 860 can also be distributed over and/or accessed via the network interface 850*a*. In this instance, computer readable code can be stored and executed in a distributed fashion using the computer system 800. For example, in some embodiments, one or more components of the system 800 can be tethered to send and/or receive data through a local area network ("LAN") 890*a*. In some further embodiments, one or more components of the system 800 can be tethered to send or receive data through an internet 890*b* (e.g., a wireless internet). In some embodiments, at least one software module 880 running on at least one processor 820 can be configured to be coupled for communication over a network 890*a*, 890*b*.

In some embodiments, one or more components of the network 890*a*, 890*b* can include one or more resources for data storage and retrieval. This can include any computer readable media in addition to the computer readable medium 860, and can be used for facilitating the communication of information from one electronic device to another electronic device. Also, in some embodiments, the network 890*a*, 890*b* can include wide area networks ("WAN"), direct connections (e.g., through a universal serial bus port), other forms of computer-readable medium 860, or any combination thereof. In some embodiments, the software modules 880 can be configured to send and receive data from a database (e.g., from a computer readable medium 860 including data sources 870*a* and data storage 870*b* that can comprise a database). Further, in some embodiments, data can be accessed and received by the software modules 880 from at least one other source.

In some embodiments, one or more components of the network 890*a*, 890*b* can include a number of user coupled devices 900 such personal computers including for example desktop computers, laptop computers, digital assistants, personal digital assistants, cellular phones, mobile phones, smart phones, wearable technology devices (e.g. smart watches, activity monitors, heart rate monitors), glasses, cameras, pagers, digital tablets, internet appliances, and other processor-based devices. In general, a client device can be any type of external or internal devices such as a mouse, a CD-ROM, DVD, a keyboard, a display, or other input or output devices 870*c*. In some embodiments, at least one of the software modules 880 can be configured within the system 800 to output data to a user via at least one digital display. Further, in some embodiments, various other forms of computer-readable medium 860 can transmit or carry instructions to a user interface such as a coupled device 900, including a router, private or public network, or other transmission device or channel, both wired and wireless.

In some embodiments, the system 800 as described can enable one or more users 950 to receive, analyze, input, modify, create and send data to and from the system 800, including to and from one or more software modules 880 running on the system 800. Some embodiments include at least one user 950 accessing one or more modules, including at least one software module 880 via a stationary I/O device 870*c* through a LAN 890*a*. In some other embodiments, the system 800 can enable at least one user 950 accessing software module 880 via a stationary or mobile I/O device 870*c* through an internet 890*a*.

In some embodiments, the brace system or controller can comprise software modules that are upgradeable. In some embodiments, the software modules can be upgraded by an Internet download (for example through the Internet 890*a* shown in FIG. 5). In some embodiments of the invention, the Internet download can comprise accessing at least one or more software modules stored in a cloud-based storage location. In some embodiments, the brace system can access a cloud-based storage location to perform periodic software updates and/or to store brace system data, and/or data from a brace system controller, and/or user data (i.e., data from a brace system attached to the user).

With the above embodiments in mind, it should be understood that some embodiments of the invention can employ various computer-implemented operations involving data stored in computer systems (such as the system 800 shown in FIG. 5). In addition, in some embodiments, the above-described applications of the monitoring system can be stored on computer-readable storage media (such as computer readable medium 860). These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Any of the operations described herein that form part of the invention are useful machine operations. The invention also relates to a device or an apparatus for performing these operations. The embodiments of the invention can be defined as a machine that transforms data from one state to another state. The data can represent an article, that can be represented as an electronic signal and electronically manipulate data. The transformed data can, in some cases, be visually rendered onto a display, representing the physical object that results from the transformation of data. The transformed data can be saved to storage generally or in particular formats that enable the construction or depiction of a physical and tangible object. In some embodiments, the manipulation can be performed by one or more processors 820. In such an example, the processors 820 can transform the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Further, the brace system as described will result in a large quantity of data that must be manipulated, transformed, refined, reduced, or changed from one state to another to be able to efficiently resolve into meaningful segments of data that the user or clinician can utilize and make medical based judgments upon. In one embodiment, the brace system or controller includes software that performs a data collection and pre-filtering algorithm that stores data onto storage media only after some of the desired conditions have been met (e.g. the user is wearing the brace and movement is occurring above/below a desired threshold, or ROM data is captured only when user is vertical, or in periodic time points throughout the day such as once per minute or during user awake hours, etc.) In another embodiment, the computer system 800 performs the data reduction and pre-filtering function. Computer-readable storage media (such as computer readable medium 860) as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

In some embodiments of the invention, the initiation of wireless data transfer from and/or to the brace system (e.g., by using cellular transfer of data) can be autonomous and/or semi-autonomous and can be configured to not require user configuration. For example, in some embodiments, the device can automatically check in when powered on. In some embodiments of the invention, the brace system can include a backend system comprising one or more servers that are looking for devices to check in at times for set usage. The backend system is the system of record for the patient compliance data. In some embodiments, if the device does not check in, the backend system or controller can send a message the patient (or anyone else on a contact list) to indicate that device should be checked in.

Some embodiments of the invention can include uploading data to the backend by coupling to a smart device or a computer. By way of example, in some embodiments, Bluetooth® products can be used to provide links between any of the brace systems or assemblies described herein and mobile computers, mobile phones, portable handheld devices, wearable technology devices (e.g. smart watches, activity monitors, heart rate monitors, glasses, cameras, etc.), personal digital assistants (PDAs), tablets, and other mobile devices and connectivity to the Internet. In some embodiments, wireless transmission can occur via a Bluetooth® wireless signal from the brace system to the smart device or computer. In some embodiments, a user interface screen can be used to enable pairing of devices by using the Bluetooth® protocol. In some further embodiments, uploading data to the backend can occur by coupling to WiFi to connect to the user's home network or office network. In some embodiments, this will require the creation of a user interface screen that allows the user to select a wireless network to connect to and to provide credentials to connect to that network.

In some embodiments of the invention, the brace system can utilize wireless protection schemes to control data access to and from the brace system. This can protect patient confidentiality and to protect the security of the data. Some embodiments include protection against unauthorized wireless access to device data and control. In some embodiments, this can include software and/or hardware enabled protocols that maintain the security of the communications while avoiding known shortcomings of existing older protocols (including for example the Wired Equivalent Privacy (WEP)). In some embodiments, usage data that is transmitted from the devices (via Bluetooth®, WiFi, or via other means) can be encrypted to ensure that only the patient or the patient's physician can obtain access to this medical information. The encryption can be done via either software executing on the processor or via external hardware that processes the data before it is transmitted. In one embodiment, each set of logs is uniquely tied to the device that created them. This can be done by the device tagging the data being transmitted from the device with a unique identifier associated with the device. The unique identifier is set either by the processor or by an external component of the system (e.g., a UUID chip).

In some embodiments, the wireless collection can include wireless collection of compliance data. For example, in some embodiments, brace system data comprising a user's compliance to certain daily movements and/or one or more physiotherapy or exercise routines can be wirelessly monitored and recorded. In some embodiments, the brace system can comprise a wireless collection of compliance data and can include creation of a record of all instances that brace system sensor determines a patient is wearing the brace system. In some embodiments, this can include stored data (e.g., data that has previously been measured and stored in a volatile or non-volatile memory by the brace system). For example, this can include a wireless collection of kinematic data, including data such as orientation data and acceleration data. In some embodiments, the brace system can continue to store and transmit data when the user is not wearing the brace system. In some embodiments, the data can be ignored, and in other embodiments, the data can be stored and/or wirelessly transmitted. In some embodiments, the brace system can wirelessly transmit data from the brace system to at least one telemedicine system. In some embodiments, the brace system can wirelessly transmit data from the brace system to at least one physiotherapist and/or physiotherapist system.

Figure 6:
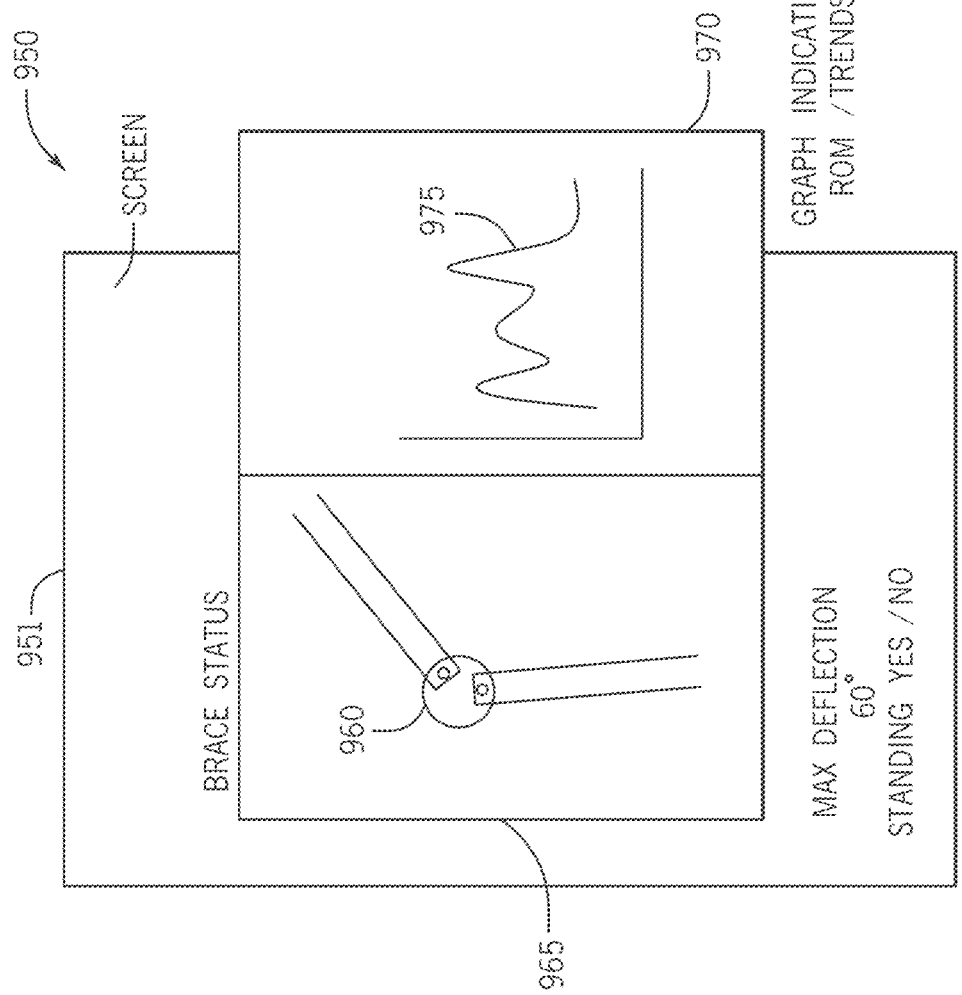
FIG. 6 illustrates an image of screen showing the current status of a brace including a representation of the degree of flexure and orientation relative to the ground in accordance with some embodiments of the invention.

FIG. 6 illustrates an image of screen 950 showing the current status of a brace assembly 960. In some embodiments of the invention, a brace system 951 can include a display screen 950 configured for projecting the status of the brace system 951 including the brace assembly 960, and displaying a representation 965 of the degree of flexure and orientation of the brace assembly 960 relative to the ground. In some embodiments, the brace system 951 can render a display of the brace system 951 substantially in real-time and can display graphical illustrations or data pertaining to sensor data (e.g. usage trends, muscle strength trends, ROM trends, etc.) obtain from the brace assembly 960 (see display portion 970 with trend data plot 975). In some embodiments of the invention, using one or more sensors, the brace system can communicate substantially in real time the position and movement of one or more portions or sections of the brace system 951. This information can be processed by the system 951 for representation on the display screen 950 and/or for communication through a wired or wireless connection (e.g., such as a wireless data transfer data between the knee brace assembly 670 and the controller 675 shown in FIG. 3B). In some embodiments, data collected by the brace system 951 can enable a medical professional to adjust the brace system 951 based on this data. For example, the brace system 951 can measure muscle strength surrounding the knee and/or the range of motion of the knee (e.g., obtained via an accelerometer or positional encoder). The medical professional can then utilize this feedback and data to adjust the treatment of the patient and/or adjust the brace system 951 based on these readings.

In some embodiments, one or more brace control programs can be selected by a medical professional or patient that can be dynamic (e.g., changeable or variable, not a fixed frequency, not fixed timing, not a fixed waveform, etc.) and can cause different types of EMS to be executed on different parts of the patient's body. For example, if the feedback data obtained and rendered by the brace system 951 from the brace system's control electronics indicates that the patient's vastus medialis oblique muscles are getting stronger while the patient's distal central hamstring (or, in another embodiment, the patient's calf muscle) is not getting stronger, a medical professional (e.g., physician or physical therapist) can instruct, via one or more of these programs, the brace system 951 to execute a predetermined brace control program. In some embodiments, the brace system 951 can include specific programs for the first week after surgery, specific programs for the first month after surgery, specific programs for arthritis, etc.

Figure 9:
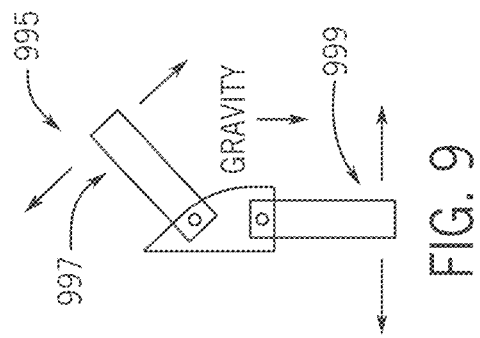
FIGS. 8-9 each provide representations of potential motion of various portions of a brace system that can be monitored in the brace system represented in FIG. 7 in accordance with some embodiments of the invention.
Figure 8:
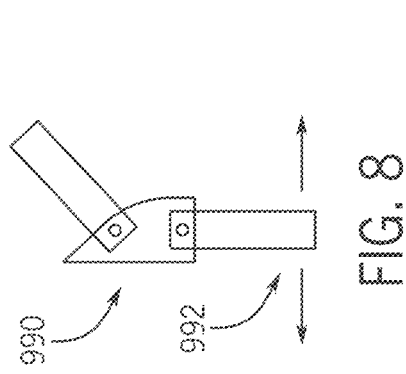
Figure 7:
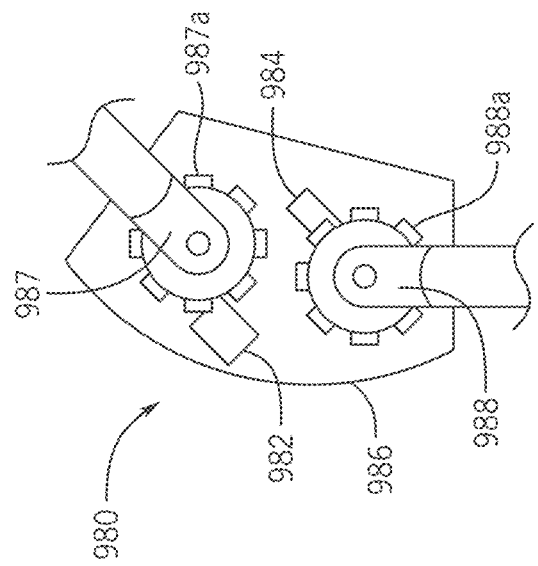
FIG. 7 shows a representation of a brace system with kinematic data collection sensors in accordance with some embodiments of the invention.

In some further embodiments, the motion of any portion of any of the brace assemblies or systems described herein can be sensed. In some embodiments, at least one optical or other type of sensor can be coupled or integrated with the assemblies or systems for sensing motion and/or position. For example, FIG. 7 shows a representation of brace system 980 with kinematic data collections sensors 982, 984 in accordance with some embodiments of the invention. In some embodiments, one or more components of the brace assembly 986 can be monitored by the sensors 982, 984. FIGS. 8-9 provide representations of the potential motion of various portions of the brace system that can be monitored in the brace system 950 represented in FIG. 7 (where brace system 980 represents brace system 950). In some embodiments, an optical sensor (e.g., such as sensors 982, 984) can be used in combination with a portion of the brace system 980 that includes an optically discernable region comprising an observed region. For example, in some embodiments, one or more optical sensors 982, 984 can be positioned to detect motion of a neighboring region of the brace system 980 that comprises an observed region (i.e., a region of the brace system that is sensed by the optical sensor). In some other embodiments, one or more optical sensors 982, 984 can be positioned to detect motion relative to a neighboring region of the brace system that comprises an observed region (e.g., the portion of the brace system comprising the observed region remains motionless and the portion of the brace system including the optical sensors can move relative to the observed region). In some embodiments of the invention, the observed region can comprise an optically reflective material. In some further embodiments, the observed region can comprise one or more markings capable of being detected by the one or more optical sensors. In some embodiments, observed region can comprise an optical emitter. For example, in some embodiments, one or more of the observed regions can comprise an optical or infra-red LED. For example, in some embodiments, the position and/or movement of stay 987 can be monitored by sensor 982. In some embodiments, the sensor 982 can comprise an optical sensor, and the stay 987 can include optical encoders 987a (e.g., tabs or marks that can be read or sensed by the sensor 982). Further, in some embodiments, the position and/or movement of stay 988 can be monitored by sensor 984. In some embodiments, the sensor 984 can comprise an optical sensor, and the stay 988 can include optical encoders 988a (e.g., tabs or marks that can be read or sensed by the sensor 984).

In some other embodiments of the invention, electrical sensing of motion of the brace system 950 can be used. For example, in some embodiments, a component of the brace system 950 (e.g., a hinge) can include an electrical resistor and/or electrically resistive portion with an electrical resistance that changes as a portion of the brace system 950 moves. For example, in some embodiments, the electrical resistance can start at a known value, and increase as the degree of openness of the hinge increases.

In some embodiments, one or more of the sensors 982, 984 can comprise linear, angular, rotary based position sensors/encoders. Some embodiments of the invention can comprise linear displacement sensors that are utilized on hinge bars to determine what length setting the patient has selected. In some embodiments, positional sensors can be used to determine which ROM stops have been engaged, and compared to what ROM limits should or should not be employed or if the extension lockouts have been applied as prescribed. In some other embodiments, any of the brace systems or assemblies (e.g., such as brace system 950) described herein can comprise force sensors, torque sensors, and/or a dynamometer that can be integrated to determine the strength or force/torque output of the joint and correlated to recovery of the patient.

Conventional LAMES uses various dc, ac, and biphasic waveforms to induce muscle response in human tissue. These can be either voltage or current driven and open or closed loop, and the amplitude of the wave can be directly controlled by the settings of the device. Electrical stimulation can also be used to reduce edema or swelling in the target tissues. FIG. 10 illustrates a sensor assembly 1000 for surface edema detection through optical sensing in accordance with some embodiments of the invention. In some embodiments, the assembly 1000 can be used for regulating closed loop feedback for electrical stimulation therapies for edema. In some embodiments, an emitter/sensor assembly 1005 can be configured to emit red light from one or more LED's 1010 into the patient's skin epidermis (1060) and dermis layers (1070), and detecting the light signals and wavelengths (1085) reflected back from the skin using one or more photodetectors (e.g., such as photo transistor 1020.) In some embodiments, the assembly 1000 can optically determine the level of surface edema near the detector. Water has a characteristic optical absorption band that can be used to make this determination. In some embodiments, using output from this assembly 1000 in a closed loop feedback manner can enable the electrical stimulation system to optimize stimulation parameters to achieve the desired level of edema reduction. Some embodiments include waveform modulation by setting a maximum current to set the wave amplitude. Further, in some embodiments, two separate feedback loops can be used to modulate the wave (dynamically vary both current and voltage) to maintain constant power dissipation. The amplitude of the current and voltage waveforms can be changed, but not the general shape of the waveform. In some embodiments, waveforms can build up on a carrier pulse of about 30 Hz to about 100 Hz and provide a pulse block that is about 100 μs to about 10,000 μs wide. Some embodiments include a closed loop feedback mechanism. In some embodiments, the power supply can provide a high current low voltage supply with multiple nested feedback loops that when summed create a time approximated constant power system. In some embodiments, the power supply can maintain a constant power output, by trying to maintain the current load of the system first, and the voltage load of the system second. When the power supply output is summed over time, it can be relatively constant and based on the amplitude selected by the user in the user interface.

In some embodiments, feedback can be collected on the back side of the feedback loop, after it has passed through the user. Some embodiments include control systems that are configured to maintain a constant output from the system. In some embodiments, the system can be configured to maintain a constant output as is passes through the user. In some embodiments, during the course of LAMES, the conductive properties of a user's tissues change. In some embodiments of the invention, the brace system can comprise a feedback loop that compensates for tissue changes by attempting to keep the output constant. As the resistance rises, the system can induce more current to keep the power dissipation levels constant in the system. In some embodiments, if the resistance gets beyond a certain point the voltage of the system will spike to attempt to break through the high resistance element and allow current to flow.

Some embodiments of the invention can comprise systems for pain relief. In some embodiments, pain relief can be provided using electrical stimulation without the use of narcotics. In some embodiments, the electrical stimulation can be provided by one or more electrical stimulators coupled to a user using a brace system. In some embodiments, a brace system can comprise at least one electrical stimulator configured to provide electrical stimulation to provide pain relief to the user. Nerves responsible for transmitting sharp pain send out an encoded burst of signals back to the autonomic nervous system. The introduction of a constant signal can disrupt the encoding of the pain signal and offer some pain relief. Some embodiments of the invention are configured to enable a user to self-tune the signal for maximum effectiveness. In some embodiments, this can be achieved by varying pulse amplitude, pulse width, and/or pulse duration. For example, FIG. 11 illustrates a system 1100 for non-narcotic pain relief using electrical stimulation therapy to override pain impulses in accordance with some embodiments of the invention. In some embodiments of the invention, non-narcotic pain relief can be provided using electrical stimulation to override a pain impulse. In some embodiments, the non-narcotic pain relief system can comprise a control unit 1105 coupled to epidermis 1103 via electrodes 1110, 1115 configured to provide a current flow 1120 through nociceptors 1125 of the user 1101.

Some embodiments of the invention can include systems configured for obtaining biological feedback. In some embodiments, biological feedback can be provided by one or more biological feedback sensors coupled to a user using a brace system. In some embodiments, one or more of the brace systems or assemblies described herein can comprise at least one biological feedback sensor configured to provide biological feedback data from a user. For example, in some embodiments, the human contact sensors shown in FIG. 2T can comprise one or more biological feedback sensors positioned within the inner region of a brace. In some embodiments, these sensors can be proximity or contact sensors capable of determining if a device (e.g., such as a brace) is being worn by a user. Further, for example, electrical sensors can be included to determine the impedance between sensors to determine if the device is attached to human skin. In some further embodiments, other sensors can be used such as blood pressure sensors, blood oxygen level sensors, heart rate sensors, laser or ultrasound based sensors for measuring movement of tissues or fluids, hydration sensors that measure the interstitial fluid levels to determine hydration levels, force or pressure sensors for measuring the muscle activity/response, or electromyography type sensors to measure muscle recruitment from the electrical stimulation therapy, or to measure the level of muscle fatigue. In some further embodiments, by measuring the hydration levels of the user, the system can tune the electrical stimulation signals to be more optimized or less painful for the user or provide feedback to the user to drink more fluids.

In some further embodiments, the biological feedback sensor can comprise one or more temperature sensors. In some embodiments, one or more temperature sensors can be coupled to or integrated with a brace system, and used to monitor temperature proximate the user. In some embodiments, one or more temperature sensors can be used in combination with NMES therapy and used to sense temperatures proximate stimulation electrodes. In some embodiments of the invention, one or more temperature sensors can be used in combination with NMES therapy and used for feedback control. For example, in some embodiments, the brace system can include a closed loop feedback system that provides electrical muscle stimulation (EMS) to a joint of a human patient in response to feedback from a sensed temperature. In some embodiments, the brace system can include one or more sensors in physical contact with the skin of the patient and configured to obtain a sense and/or obtain information from a region of the skin and/or of a NMES electrode contacting the skin of a patient. For example, in some embodiments, one or more temperature sensors can be used to sense temperature proximate one or more NMES electrodes. In some embodiments, the brace system can also include brace control electronics in communication with the sensor(s) to form a closed loop system via a combination of bracing the joint and electrical muscle stimulation (EMS). Further, in some embodiments, the brace control electronics can be configured to receive temperature measurements of the skin of the patient and/or of one or more of the electrodes, and is further configured to instruct the sensor to apply a current/voltage/power onto the skin based on the temperature. For example, NMES can be reduced or increased based at least in part a temperature measurement from the one or more temperature electrodes. In some embodiments, using one or more temperature sensors to sense temperature proximate one or more NMES electrodes, where the sensed temperature is used for control of NMES, NMES burns can be substantially reduced or eliminated. In some further embodiments, one or more temperature sensors sensing changes in a user's body and/or body core temperature can be used to estimate a user's activity level, or the presence of an infection.

Some embodiments of the invention include systems for monitoring for the presence or concentration of at least one chemical, biochemical marker or other analyte. In some embodiments, analytes can include naturally occurring or synthetic compounds or molecules, and/or metabolites. For example, in some embodiments, the brace system can include a blood oxygen sensor apparatus configured for measuring the oxygen content of blood. In some embodiments, a brace system configured with blood oxygen monitors can enable an assessment of blood pooling and can be used to prevention of deep vein thrombosis (DVT), and other potentially fatal events such as pulmonary embolism, extremity edema, and so on. For example, an example of biological feedback collection is shown in FIG. 12. Some embodiments include a blood oxygen sensor 1200 coupled with a stimulation system that include at least two electrodes 1205, 1210.

In some further embodiments, one or more of the brace systems or assemblies described herein can include a sensor apparatus configured for measuring nicotine, nicotine metabolites, and/or other drugs or drug metabolites including stimulants, depressants, hallucinogens, designer drugs, and anabolic steroids. In some embodiments, at least one of the brace systems or assemblies described herein can comprise one or more sensors configured to detect one or more of these substances in-vivo and to notify the healthcare professional since they may affect the healing and rehabilitation process. In some other embodiments, the brace system can be configured with sensors to detect the immediate environment of a user. For example, in some embodiments, nicotine from first-hand or second-hand smoke can be sensed using one or more brace system chemical sensors and used to determine if the user may have smoked and/or has been exposed to high levels of tobacco smoke.

In some embodiments, any of the brace systems or assemblies described herein can include at least one sensor configured to measure a heart-rate of a user. For example, in some embodiments, at least one heart rate sensor can be used to determine if patients are performing prescribed exercises and/or physical therapy. Further, in some embodiments, at least one heart rate sensor can be used to determine a user's overall activity level (used for healing and data correlation). In some further embodiments, lung and/or breath sensors can be used to provide data for a $VO_2$ max calculation, and provide additional data on activity level. In some embodiments, the brace system can include at least one heart-rate sensor integrated with a portion of a brace. In other embodiments, the brace system can include at least one heart-rate sensor coupled to and adjacent to or some distance from the brace.

Some embodiments of the invention can comprise a non-invasive blood pressure sensor configured to measure arterial blood pressure continuously or intermittently. In some further embodiments, a user's heart-rate can be measured in addition to sensing the user's blood pressure. In some embodiments, one or more of the brace systems or assemblies described herein can include at least one blood pressure sensor integrated with a portion of a brace. In other embodiments, the brace system can include at least one blood pressure sensor coupled to and adjacent to or some distance from the brace.

In some further embodiments of the invention, some one or more of the brace systems or assemblies described herein can comprise an electromyography sensor, a strain gage sensor or other sensor configured to measure strains continuously or intermittently. In some embodiments, these measurements can be used to assess motion, deflection, or provide quantifiable data of muscle growth, muscle contraction, or forces, torques or pressures resulting from a muscle contraction. The muscle contraction may be voluntary or involuntarily elicited via electrical muscle stimulation. In some embodiments, the data collected from the electromyography sensor or strain gage sensor can be utilized in a closed loop feedback control methodology in order to optimize/customize the electrical stimulation parameters to provide the most efficient or strongest muscle contraction for that patient. The data can also be utilized by the healthcare provider to fine tune the treatment programs based on the patient's data captured from the electromyography or strain gage sensor.

Figure 13:
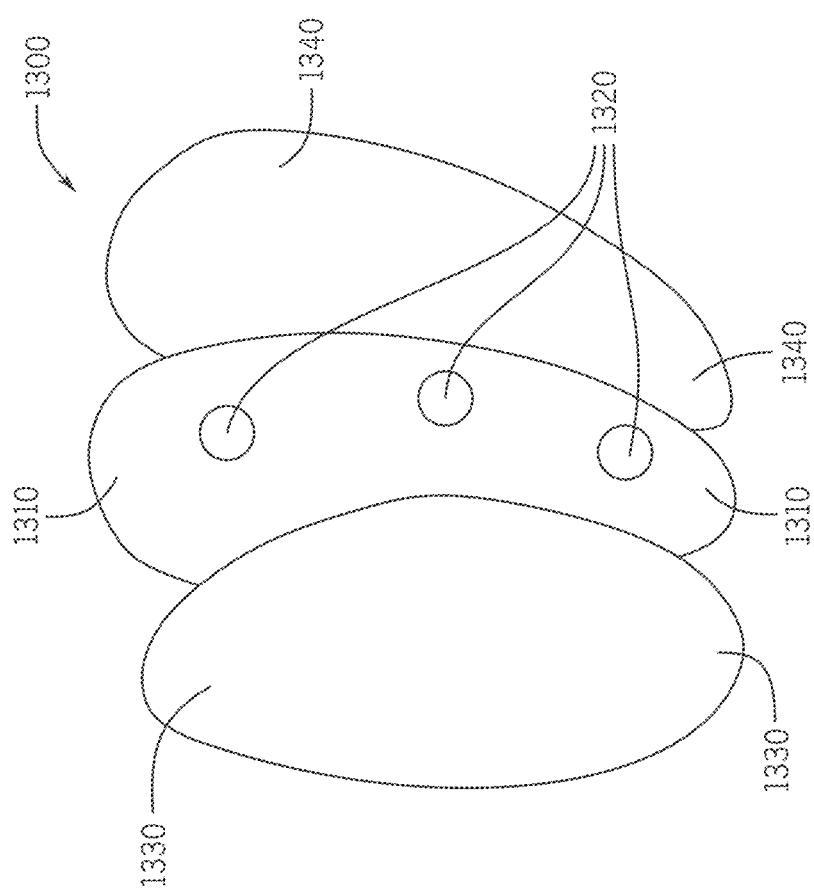
FIG. 13 illustrates a smart electrode in accordance with some embodiments of the invention.

Some embodiments of the invention can include a brace system or assembly described herein that can include at least one smart electrode. For example, FIG. 13 illustrates a smart electrode 1300 in accordance with some embodiments of the invention. In some embodiments, at least one of the brace systems, assemblies, or methods described herein can comprise one or more smart electrodes 1300 that can comprise a temperature responsive color change pigment that can be used to determine if the electrode has experienced an overheated condition. In some embodiments, the temperature responsive color change can be used to determine if the electrode has been heated past a point that would cause a dielectric breakdown of the electrode material. The degradation of a stimulation electrode through dielectric breakdown can produce an unsafe electrode because of a change in the electrical characteristics, and a degraded electrode of this type should not be used on a person. In some embodiments, any color change within the smart electrode 1300 can be used to signify whether the electrode is safe to use or whether the electrode should be replaced. In some embodiments, the color change can also be used to indicate to the physical therapist whether the electrode may have potentially resulted in a skin burn or to allow the physical therapist to select electrical stimulation settings that produce energy outputs below the temperature threshold where skin burns can occur. Some embodiments of the smart electrode 1300 can include a conductive silicon layer 1310 including one or more sensors 1320 comprising a temperature sensitive color change material mounted on a fabric base 1340. Further, some embodiments include a clear hydrogel layer 1330 covering at least a portion of the conductive silicon layer. The clear hydrogel layer 1330 can provide physical protection to the sensor layer that is optically transparent to enable detection of the one or more sensors. In some other embodiments, the conductive silicon layer can be replaced by alternative conductive or semi-conductive layers, including PCB, HDMI, conductive glass layers, conductive polymer layers, ceramic layers, and so on. In some other embodiments, an optical sensor or photo detector element) can be included to detect color change in the smart electrode. In some embodiments, this automation can be accomplished by including a color detection sensor that is placed directly on and/or proximate the electrodes surface where it can be configured to monitor the color of at least a portion of the electrode. In some embodiments, the color sensor can be coupled to a controller to monitor changes to a color of the electrode that denotes an unsafe electrode operational condition for human use. In some embodiments, the color sensor can be used by the system to identify the change and to disable the output of the system after the change is detected. Further, in some embodiments, the color change can be detected automatically and can be used in a closed-loop feedback fashion to optimize electrical stimulation parameters to prevent excessive temperatures and patient burns from occurring during electrical stimulation.

Figure 14C:
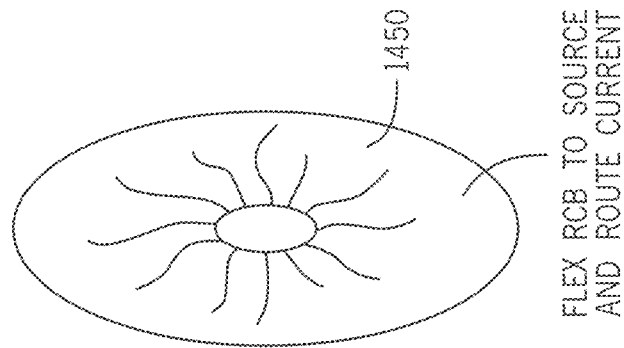
FIGS. 14A-14C illustrate adaptive electrodes in accordance with some embodiments of the invention.
Figure 14B:
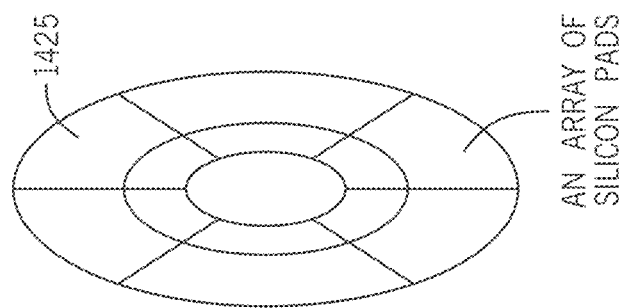
Figure 14A:
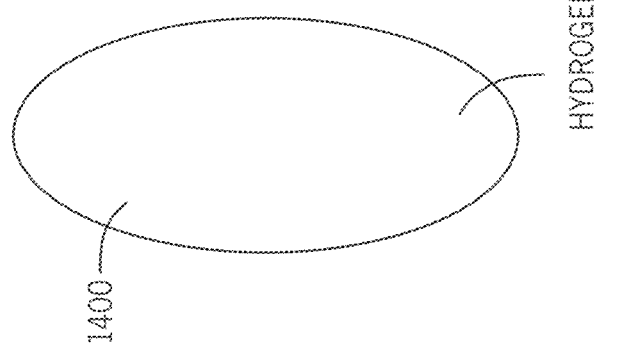

In some embodiments of the invention, at least one of the brace systems or assemblies described herein can include at least one adaptive electrode. For example, FIG. 14A-14C illustrates adaptive electrodes 1400, 1425, 1450 in accordance with some embodiments of the invention. In some embodiments, the adaptive electrodes can be placed relative to one or more muscles to provide stimulation. In some embodiments, the electrode can comprise a flexible PCB layer (shown as layer 1450), a layer comprising an array of silicon pads (layer 1425), and a hydrogel layer (layer 1400). Some embodiments include electrode clusters that contain a plurality of individual electrodes (e.g., such as electrodes comprising the layers 1400, 1425, 1450). In some embodiments of the invention, the brace system can self-tune by allowing current to pass through a selective number or all of the electrodes. In some embodiments, electrode selectivity can comprise sets with the lowest power dissipation, with greater conductor performance, that can be an indicator of being aligned with muscle fibers or with muscle motor points. Further, by splitting a single electrode into a collection of electrodes it can be possible to provide improved distribution of current as applied to the surface of a user's skin. Moreover, current electrodes have the highest current density around the edge of their pads, and the use of an adaptive electrode as described can effectively tile the electrodes to distribute current out of hot zones, and over a larger area to improve user comfort and to prevent skin burns.

In some further embodiments of the invention, the brace system can comprise one or more electrodes that comprise a circuit board located at the electrode. Some embodiments of the invention include systems and methods for using an SPI communication from the controller to communicate to a set gate at the electrode site. Further, the set gate can determine which section of the electrode produces effective electrical stimulation signals. In some embodiments of the invention, one or more electrodes and/or an array of electrodes can include a placement of electrodes configured for a specific stimulation pattern to cause the muscles of a given limb to contract in a pattern that will introduce blood flow in the tissue of that limb or to reduce edema in that region.

Some embodiments of the invention include a brace system with integrated stimulation coupled with cold therapy or heat therapy. In some embodiments, the brace system can apply selective heat and cold therapy that can be delivered to limbs in braces using an embedded system that can change the internal temperature of at least a portion of the brace. In some embodiments, this can be achieved in conjunction with applying stimulation to the selected limb. In some embodiments, the heating and/or cooling can either be applied to the entire inside of the brace, or to selected locations inside of the brace. In some embodiments, the brace system can comprise solid state heat exchangers that use the Peltier effect to directly heat or cool a specific location or region of the inside of the brace. Some embodiments of this system can use heat exchangers that are external to the brace. For example, in some embodiments, a system of tubes in a thermally conductive material can circulate a fluid that is cooled by external heat exchangers. In some further embodiments, this system can use a phase change cooling material to provide cooling to the entire inside of the brace, or to selected locations inside of the brace. In some embodiments, the system can use a phase change cooling material that freezes at 58° F., and does not reduce the temperature of the treated limb below a safe level.

Some embodiments of the invention can comprise a brace system that provides mechanical manipulation of the muscle to improve blood flow, and/or to prevent the formation of blood clots. Some embodiments of the invention can use multiple air bladders that form concentric rings around a given limb. In some embodiments, if the pressure in these rings is increased in successive rings that are in line with each other, a peristaltic pumping action can be introduced into the underlying tissue causing an increase in the flow of blood in the tissue of the given limb.

Some embodiments include a shoulder vest or sling with integrated electrical stimulation electrodes and inflatable bolsters that can be utilized to apply pressure to the electrodes for enhanced contact, conductivity and comfort with the skin. In some embodiments, inflation of an air bladder can be selectively applied and electronically controlled as a method to improve contact pressure of the electrode and resulting comfort for the user without mechanical repositioning of the electrode. Further, in some embodiments, a pump, and/or an expanding gas and/or fluid system (e.g., comprising a bladder) can be used for electrode compression. Further, in some embodiments, the inflatable bolsters can be utilized to increase or reduce pressures on specific tissues for patient comfort during exercising, sleep, or other activities. For example, an inflatable bolster can be applied posterior to the shoulder joint complex during sleeping and inflated manually by the user to provide pain relief and comfort while lying down.

Some embodiments include a brace system with an integrated pressure therapy system. For example, in some embodiments, an integrated pressure therapy system can be used to treat deep vein thrombosis, as well as perform general compression therapy. For example, in some embodiments, using inflatable bolsters or bladders in combination with selectively applied and electronically controlled actuation, the brace system can function as a pressure therapy system. In some embodiments, this pressure therapy system can be combined with electrical stimulation electrodes and system to provide a comprehensive tissue treatment system. Further, in some embodiments, the pressure therapy system can be combined with the electrical stimulation system and combined with the application of heat/ice temperature therapy to provide a comprehensive tissue treatment system.

Figure 15:
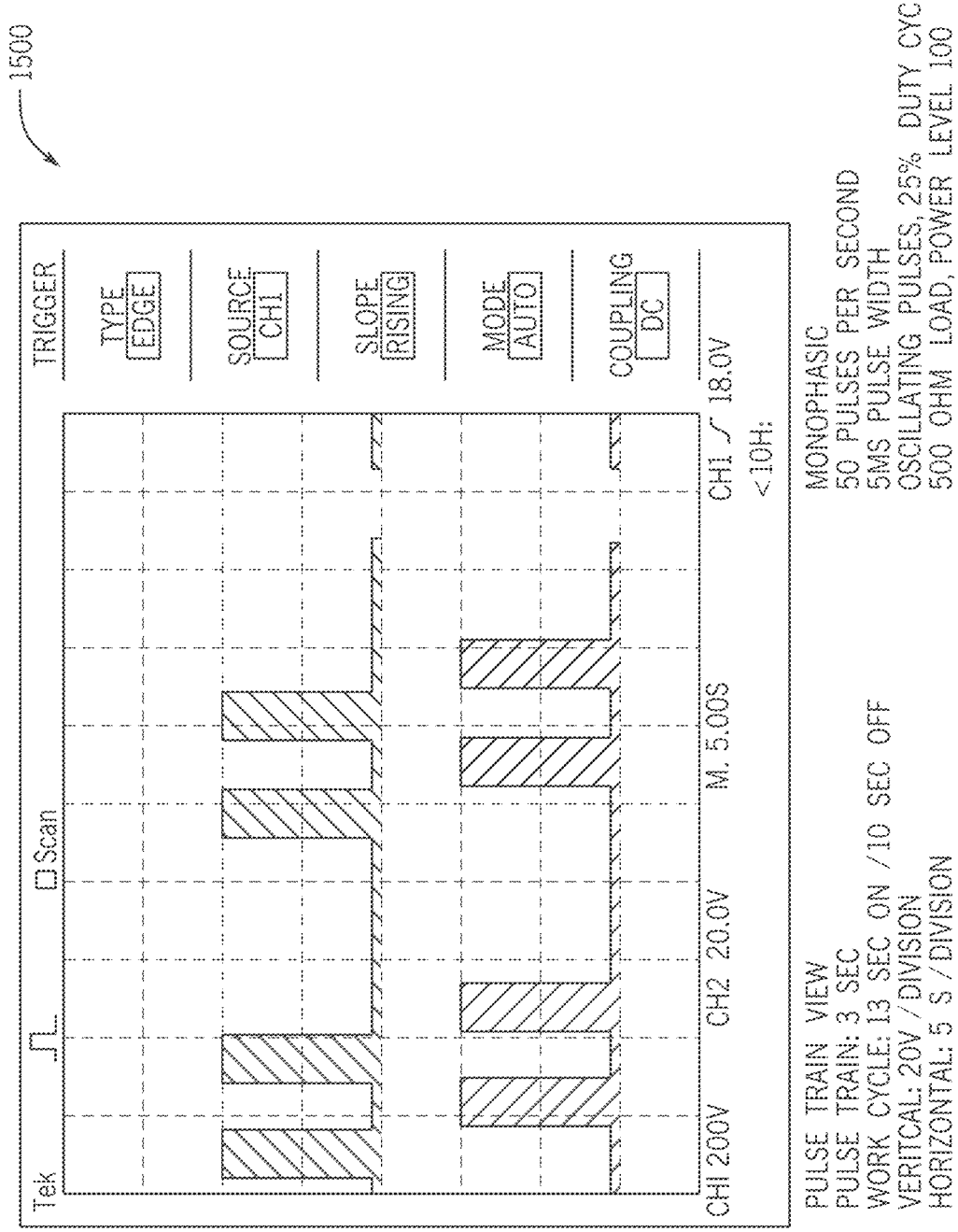
FIG. 15 illustrates an NMES post-operative oscilloscope scan of pulse trains in accordance with some embodiments of the invention.

FIGS. 15-22 show oscilloscope scan data of LAMES under various stimulation conditions produced using at least one of the brace systems or assemblies described herein. For example, referring initially to FIG. 15, illustrating an LAMES post-operative oscilloscope scan 1500 of pulse trains, the scan illustrates a pulse train view with a pulse train duration of 3 sec, a work cycle of 13 sec on/10 sec off with vertical divisions of 20V and horizontal divisions of 5 sec. The electrical stimulation pulses shown are monophasic pulses at a rate of about 50 pulses per second with a 5 ms pulse width, 25% duty cycle, and under a 500 ohm load with power level set at 100 on the device. As shown, the pulse trains oscillate between channels (e.g. muscle groups) over time and do not overlap. In some embodiments, the pulse trains are an extended time of 3 seconds in order to better allow the patient to coordinate voluntary contraction with the electrically stimulated contraction to restore volition.

Figure 16:
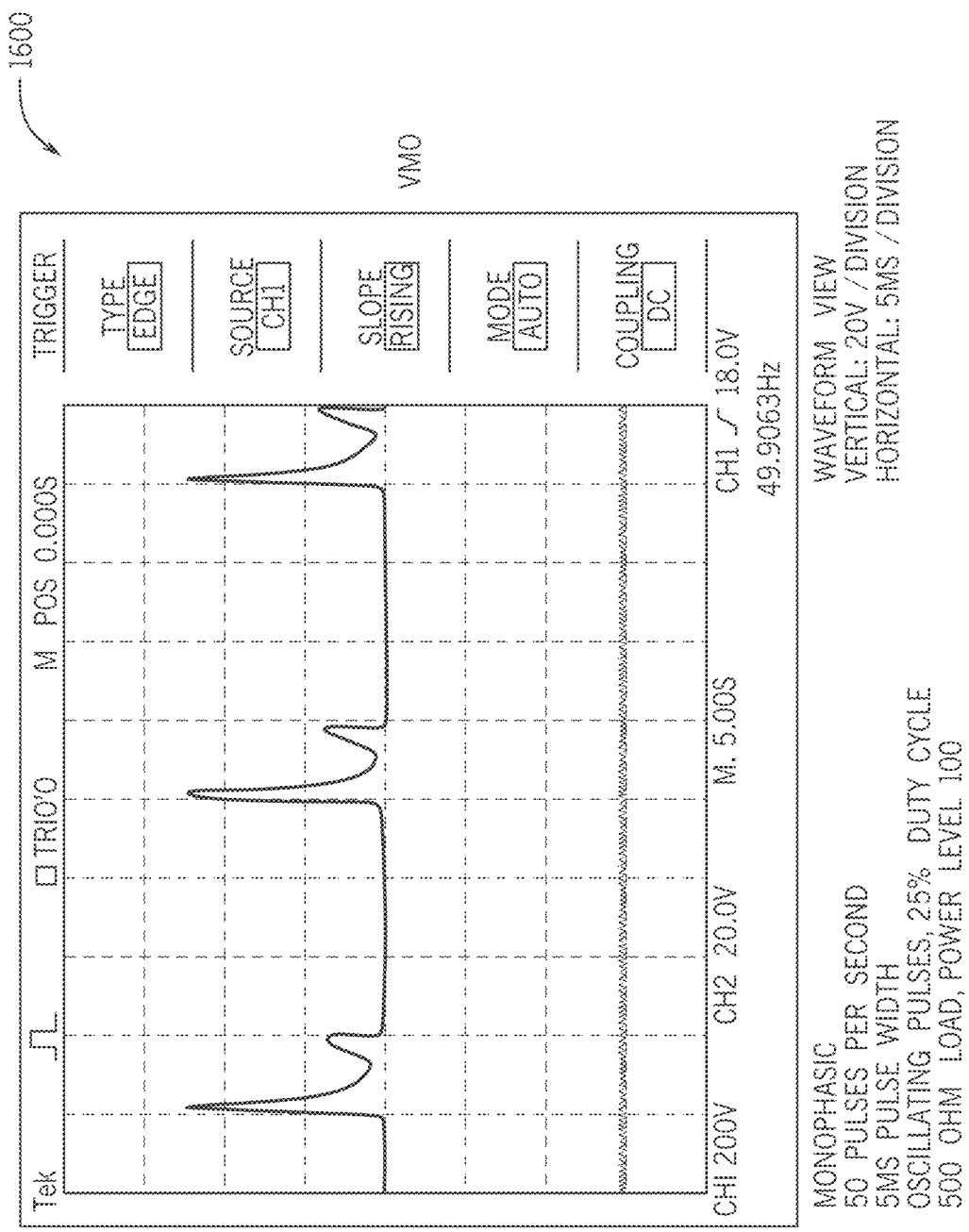
FIG. 16 illustrates an NMES post-operative oscilloscope scan of a channel's individual pulses in accordance with some embodiments of the invention.
Figure 17:
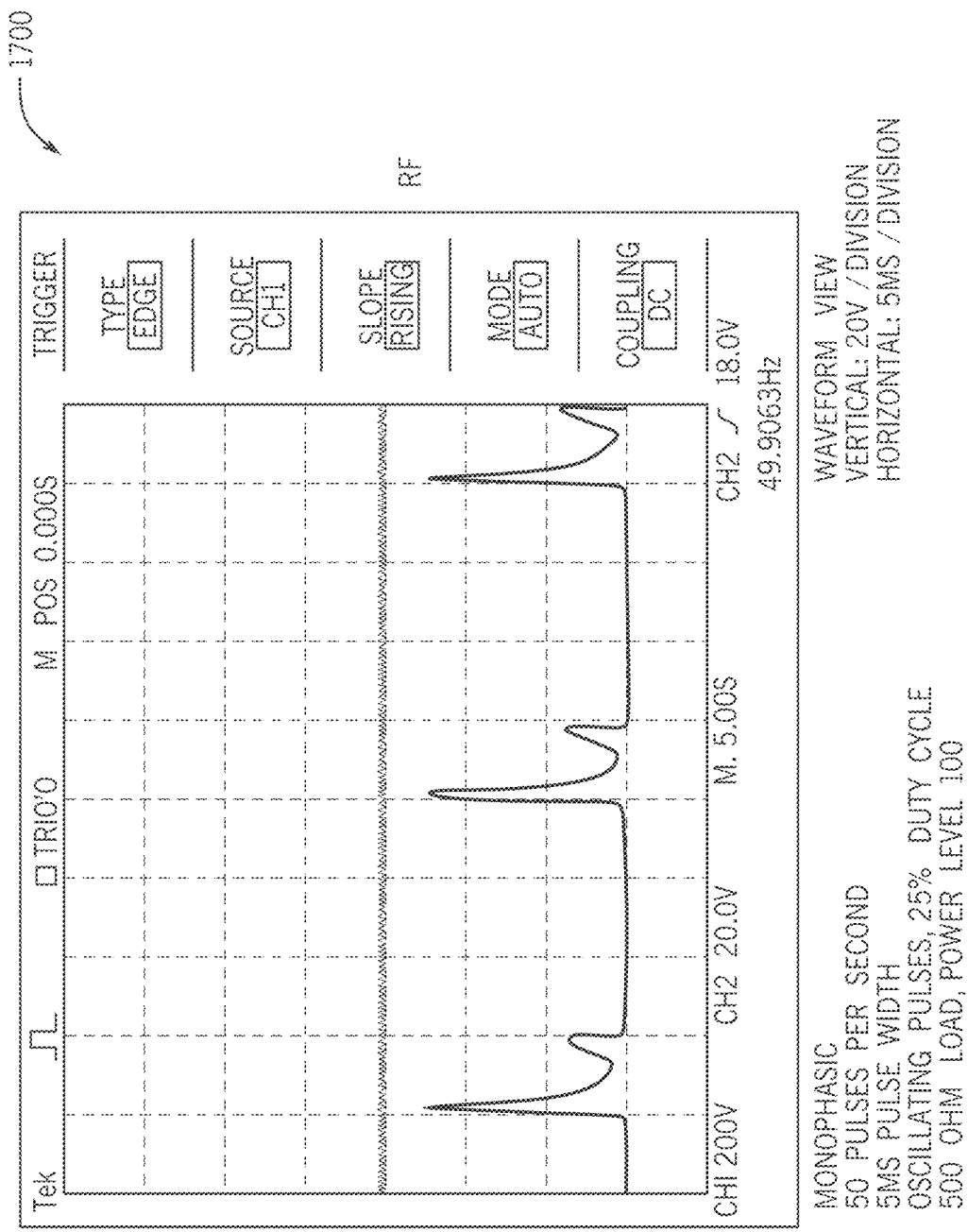
FIG. 17 illustrates an NMES post-operative oscilloscope scan of a channel's individual pulses in accordance with some embodiments of the invention.

FIG. 16 illustrates an LAMES post-operative oscilloscope scan 1600 of a channel's individual pulses in accordance with some embodiments of the invention illustrating a waveform view with vertical divisions of 20V, horizontal divisions of 5 milliseconds (hereinafter "ms"). The monophasic pulses are applied at a rate of about 50 pulses per second, with a 5 ms pulse width, 25% duty cycle, under a 500 ohm load and with the device power level set at 100. The waveform shown is not a typical waveform seen during electrical stimulation, as it is not a standard square, sinusoidal, triangular, sawtooth, or other waveform. The waveform shown is a complex waveform that has a high voltage spike on the leading end which quickly transitions to a lower voltage saddle followed by an increase in voltage towards the end of the pulse. The waveform is illustrative of the closed loop feedback power control that the system employs, as it quickly responds to the desired power delivery and current flow per the device settings. The voltages are much lower and the pulse widths much longer than conventional LAMES electrical stimulation parameters. FIG. 16 is illustrative of the electrical stimulation pulse targeted towards the Vastus Medialis Oblique (VMO) muscle group. FIG. 17 is similar to FIG. 16 and illustrates the scan 1700 with waveform targeted towards the Rectus Femoris (RF) muscle group. In some embodiments, this waveform is identical to the VMO, but in other embodiments, this waveform is modified and different for optimal stimulation of both muscle groups.

Figure 18:
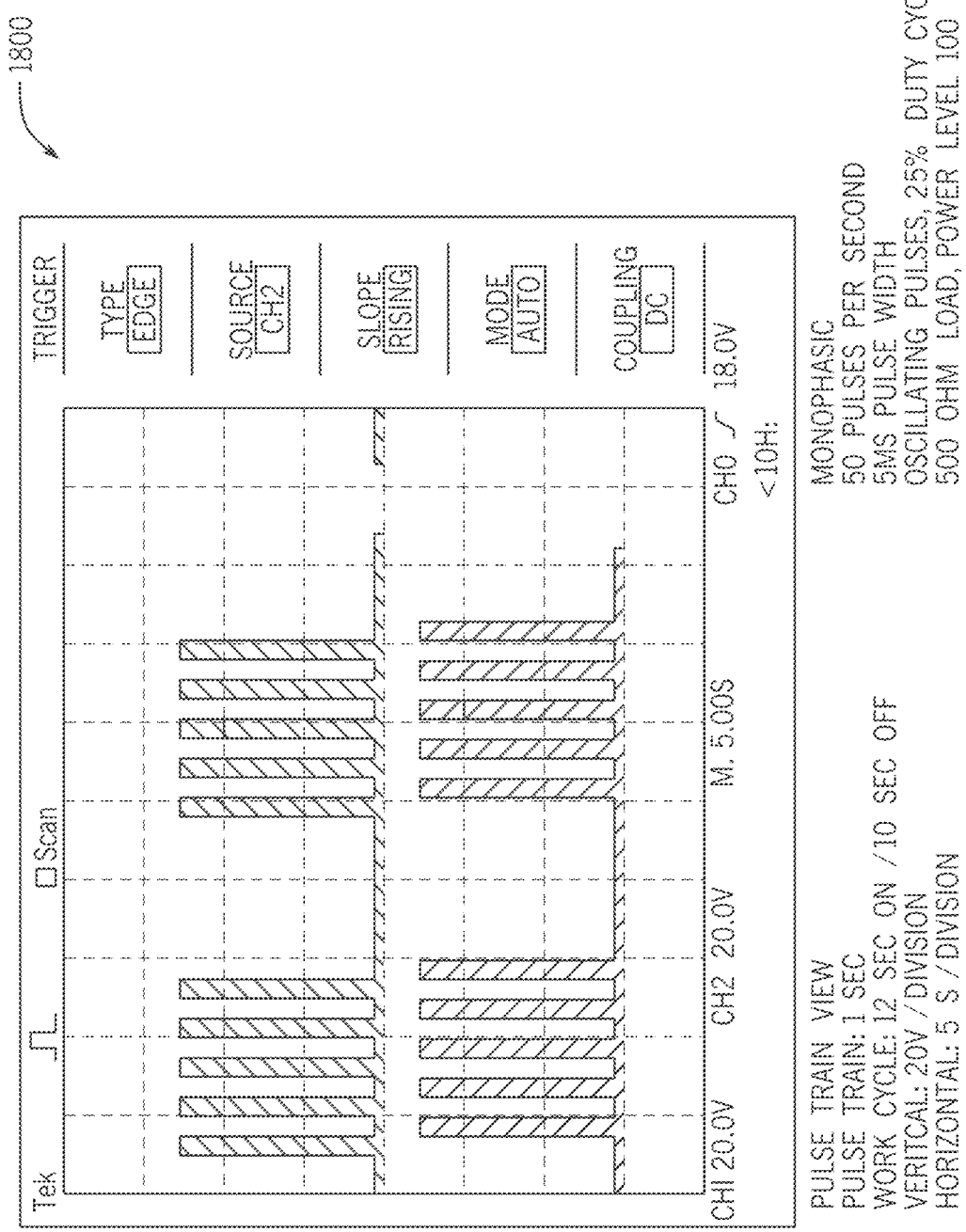
FIG. 18 illustrates an NMES strength oscilloscope scan of pulse trains in accordance with some embodiments of the invention.

FIG. 18 illustrates an LAMES strength oscilloscope scan 1800 of pulse trains in accordance with some embodiments of the invention. It illustrates a pulse train view showing pulse train duration of 1 sec with a work cycle of 12 sec on/10 sec off. The vertical divisions are 20V, and the horizontal divisions are 5 sec. The view illustrates monophasic pulses at a rate of 50 pulses per second with 5 ms pulse width, 25% duty cycle, under a 500 ohm load and with device power level set at 100. As can be seen in the oscilloscope scan, the pulse trains oscillate between channels (e.g. muscle groups) over time and do not overlap. The pulse train of 1 second allows a sustained contraction time that is similar to contraction lengths that the patient would experience during exercise.

Figure 19:
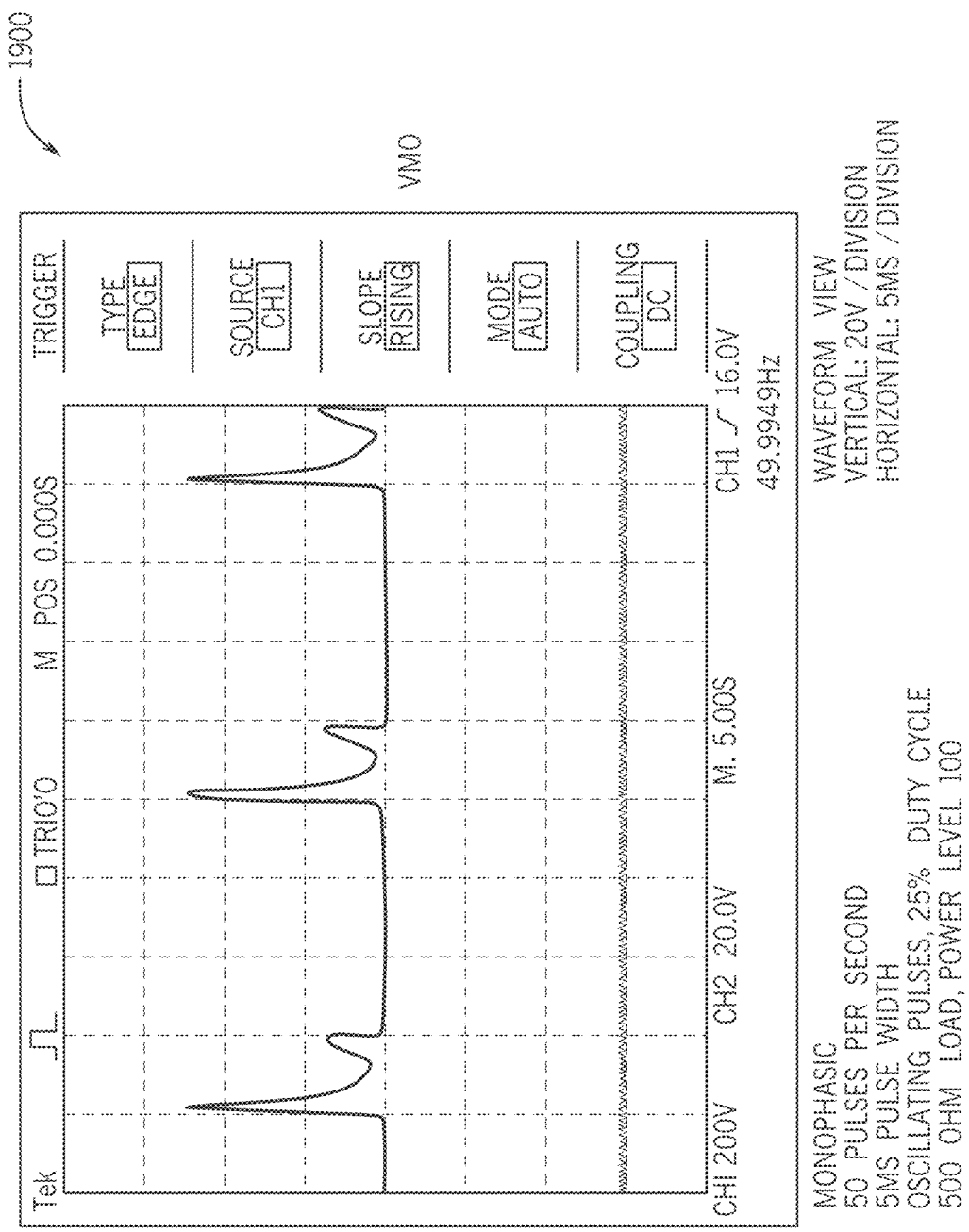
FIG. 19 illustrates an NMES strength oscilloscope scan of a channel's individual pulses in accordance with some embodiments of the invention.
Figure 20:
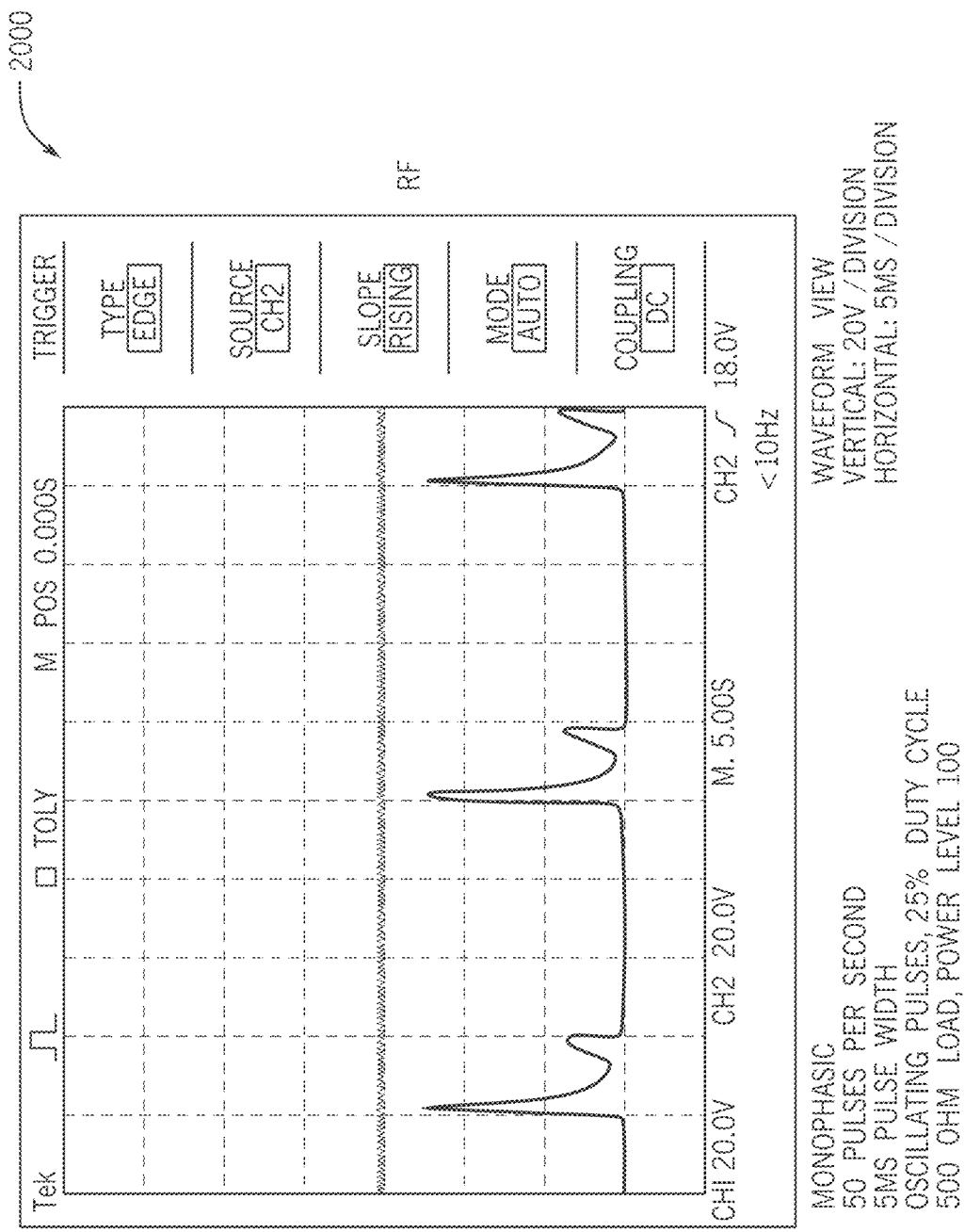
FIG. 20 illustrates an NMES strength oscilloscope scan of a channel's individual pulses in accordance with some embodiments of the invention.

FIG. 19 illustrates a scan 1900 with view of the electrical stimulation pulse waveform with vertical divisions of 20 V, and horizontal divisions of 5 ms. It illustrates a monophasic pulse at a rate of 50 pulses per second with 5 ms pulse width, 25% duty cycle, under a 500 ohm load and with device power level set at 100. The waveform shown is not a typical waveform seen during electrical stimulation, as it is not a standard square, sinusoidal, triangular, sawtooth, or other waveform. The waveform shown is a complex waveform that has a high voltage spike on the leading end which quickly transitions to a lower voltage saddle followed by an increase in voltage towards the end of the pulse. The waveform is illustrative of the closed loop feedback power control that the system employs, as it quickly responds to the desired power delivery and current flow per the device settings. The voltages are much lower and the pulse widths much longer than conventional LAMES electrical stimulation parameters. FIG. 19 is illustrative of the electrical stimulation pulse targeted towards the Vastus Medialis Oblique (VMO) muscle group. FIG. 20 is similar to FIG. 19 and illustrates a scan 1900 with the waveform targeted towards the Rectus Femoris (RF) muscle group. In some embodiments, this waveform is identical to the VMO, but in other embodiments, this waveform is modified and different for optimal stimulation of both muscle groups.

Figure 21:
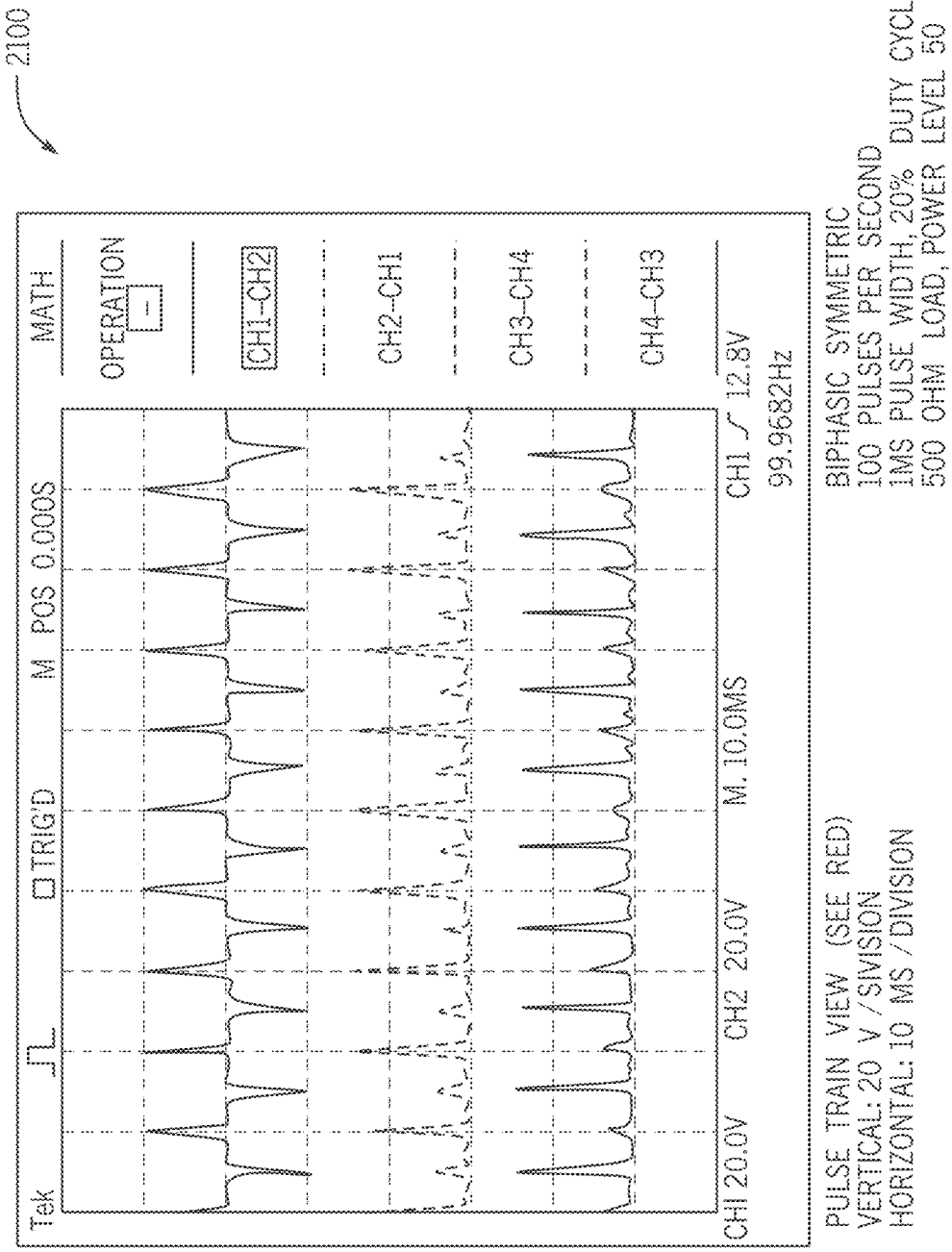
FIG. 21 illustrates a TENS oscilloscope scan of a pulse train in accordance with some embodiments of the invention.

FIG. 21 illustrates a TENS oscilloscope scan 2100 of a pulse train in accordance with some embodiments of the invention. FIG. 21 illustrates a pulse train view with vertical divisions of 20 V and horizontal divisions of 10 ms. The electrical stimulation pulse is a biphasic symmetric pulse at a rate of 100 pulses per second with 1 ms pulse width, 20% duty cycle, under a500 ohm load and with device power level set at 50.

Figure 22:
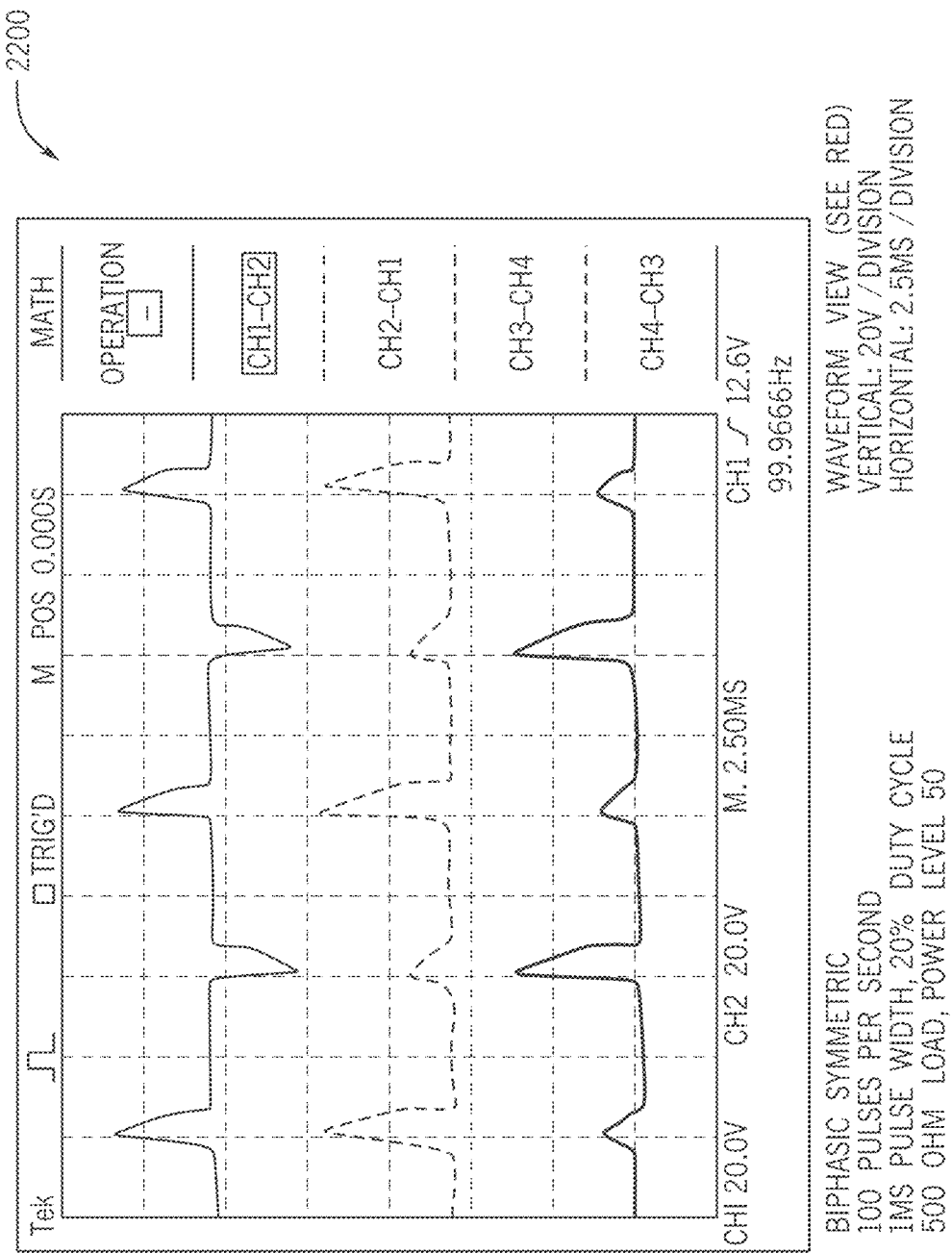
FIG. 22 illustrates a TENS oscilloscope scan of individual pulses in accordance with some embodiments of the invention.

FIG. 22 illustrates a TENS oscilloscope scan 2200 of individual pulses in accordance with some embodiments of the invention. This figure illustrates a view of the electrical stimulation pulse waveform with vertical divisions of 20 V and horizontal divisions of 2.5 ms. The electrical stimulations pulse is a biphasic symmetric pulse at a rate of 100 pulses per second with 1 ms pulse width, 20% duty cycle, under a 500 ohm load with device power level set at 50. The waveform shown is not a typical waveform seen during electrical stimulation, as it is not a standard square, sinusoidal, triangular, a sawtooth, or other waveform. The waveform shown is a complex waveform that has a high voltage spike on the leading end which quickly transitions to a lower voltage ramp down at the end of the pulse. The waveform is illustrative of the closed loop feedback power control that the system employs, as it quickly responds to the desired power delivery and current flow per the device settings. The voltages are much lower and the pulse widths much longer than conventional TENS electrical stimulation parameters.

As described earlier, some embodiments of the invention can include brace systems or assemblies that include a controller 675 coupled to a computer system or device such as a personal computers and/or a smart phone. When coupled as a therapy control system, one or more functional and/or operational aspects of a wearer's brace system or assembly can be controlled or monitored through a graphical user interface ("GUI") using the computer system or device. For example, FIG. 23 illustrates a display 2300 of a therapy system control GUI in accordance with some embodiments of the invention. In some embodiments, the display 2300 can include an introduction and start menu or process to encourage and enable a user to couple, pair or synchronize, and/or register a brace assembly for use, and/or to review help information, including text, audio, video, and/or other media files. Further, the display 2300 can include one or more selectable actions or steps from which a user can select to couple, pair, and/or register the brace assembly, or to access help information as described. For example, in some embodiments, step 2310 can include a "locate barcode" selector that a user can optionally select to initiate delivery of help information for display on the GUI and/or for delivery of audio information (e.g., such as verbal instructions) to sound generator coupled to the user's computer system or device. In some further embodiments, step 2320 can be used to select an in-application scanner to scan and synchronize a brace or brace assembly comprising a garment. In some further embodiments, step 2330 can be used to add further documents to the system and associated applications. In other embodiments, alternative optionally selectable steps or processes can be used in place of steps 2310, 2320, 2330, and/or further optionally selectable steps can be included.

In some embodiments, if a user selects step 2310, a media window can display instructions for barcode location. For example, FIG. 24 illustrates a display 2400 of a therapy system control GUI in accordance with some embodiments of the invention. In some embodiments, the display 2400 can include media window 2410 within which can be displayed information related to location of a garments barcode. The information can include text, graphics, video, still images or a combination thereof. In some embodiments, audio information can be played in place of or in addition to text, graphics, video, still images or a combination thereof.

In some embodiments of the invention, a user can download a therapy control application into a wireless device (e.g., such as a mobile phone or smart phone). In some embodiments, the user can sets up a profile, and can then pair the application to the user's brace to commence stimulation and/or range of motion treatments using the user's GUI. For example, in some embodiments of the invention, the user's GUI can be used to initiate, direct, or monitor Bluetooth® enabled pairing or coupling of one or more components of the therapy control system. FIG. 25 illustrates one embodiments of display 2500 of a therapy system control GUI in accordance with some embodiments of the invention. In some embodiments, the display 2500 can include at least one indicator 2510 showing or indicating the status of a synchronization with a user's garment. In some embodiments, the display 2500 can include step 2520 to enable a user to activate Bluetooth®. Further, in some embodiments, step 2530 can be used to synchronize with a mobile device.

FIG. 26 illustrates a display 2600 of a therapy system control GUI in accordance with some embodiments of the invention. In some embodiments, the display 2600 can include media window 2610 within which can be displayed information related to Bluetooth® synchronization. The information can include text, graphics, video, still images or a combination thereof. In some embodiments, audio information can be displayed in place of or in addition to text, graphics, video, still images or a combination thereof.

FIG. 27 illustrates a display 2700 of a therapy system control GUI in accordance with some embodiments of the invention. In some embodiments, display 2700 can include a visual icon 2710 encouraging a user to pair a user's garment with a user's device using a selector bar 2720. In some embodiments, information bar 2730 can display the status of the Bluetooth® coupling between the user's garment and device. Further, FIG. 28 illustrates a display 2800 of a therapy system control GUI in accordance with some embodiments of the invention. In some embodiments, display 2800 can include information bar 2810 indicating an error connection.

Figure 30:
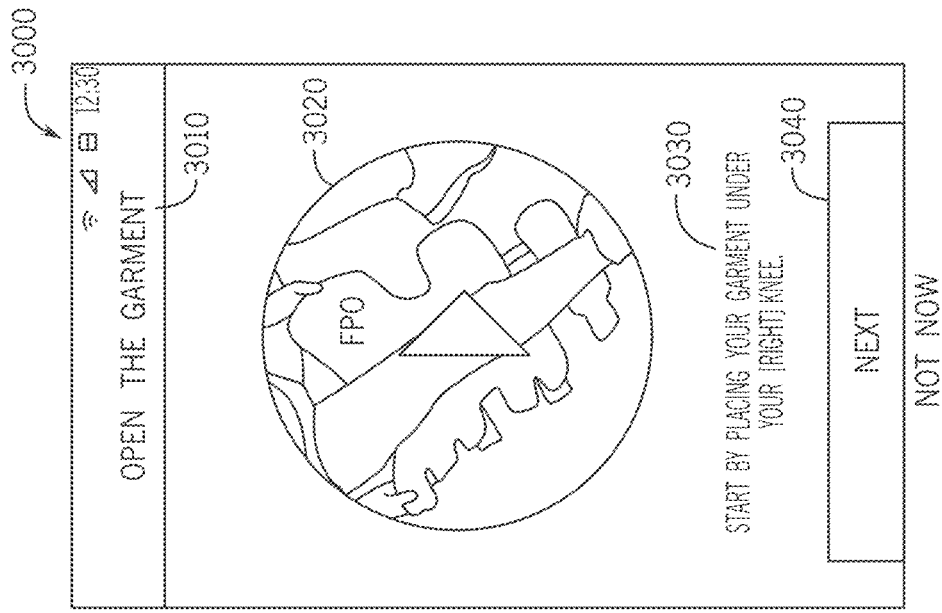
FIG. 30 illustrates a display of a therapy system control GUI in accordance with some embodiments of the invention.
Figure 29:
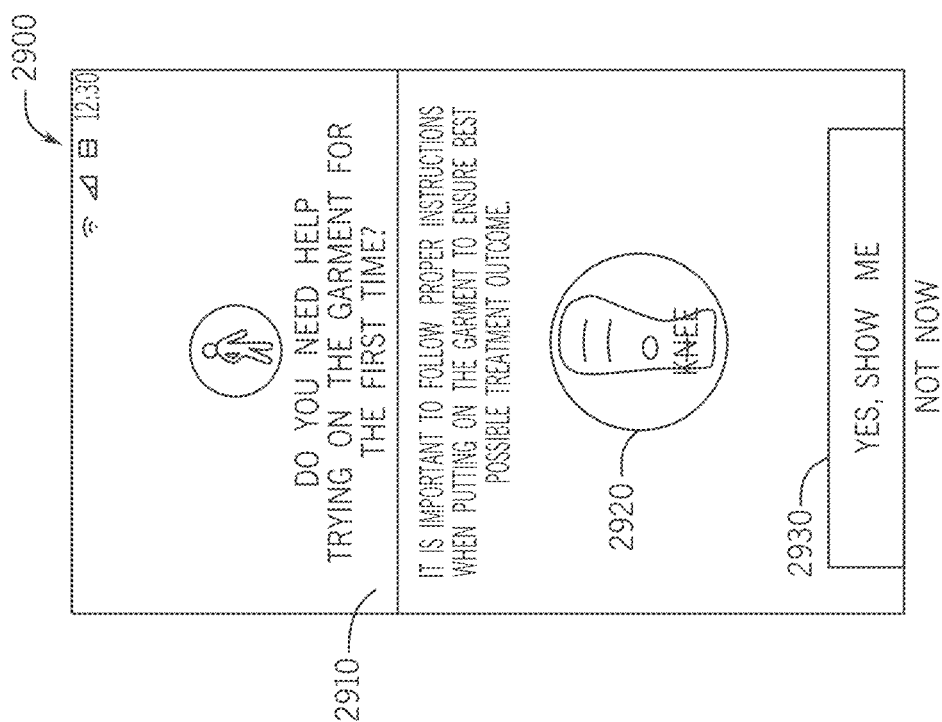
FIG. 29 illustrates a display of a therapy system control GUI in accordance with some embodiments of the invention.

In some embodiments of the invention, the GUI can provide guidance for use of a garment. For example, FIG. 29 illustrates a display 2900 of a therapy system control GUI in accordance with some embodiments of the invention. In some embodiments, information display 2910 can query a user regarding help for fitting garment. Further, an associated visual icon 2920 can provide a display of a garment with which the user may need assistance or guidance with fitting, and selector bar 2930 can provide a user with optional access to a help display. For example, FIG. 30 illustrates a display 3000 of a therapy system control GUI in accordance with some embodiments of the invention. In some embodiments, the display 3000 can include an information bar 3010 with one or more instructions, and information segment 3030 can include instructions for fitting. Further, visual indicator 3020 can include a visual display of text, graphics, video, still images or a combination thereof showing or illustrating one or more steps of a fitting procedure for a garment. In some embodiments, audio information can be played in place of or in addition to text, graphics, video, still images or a combination thereof.

Figure 31:
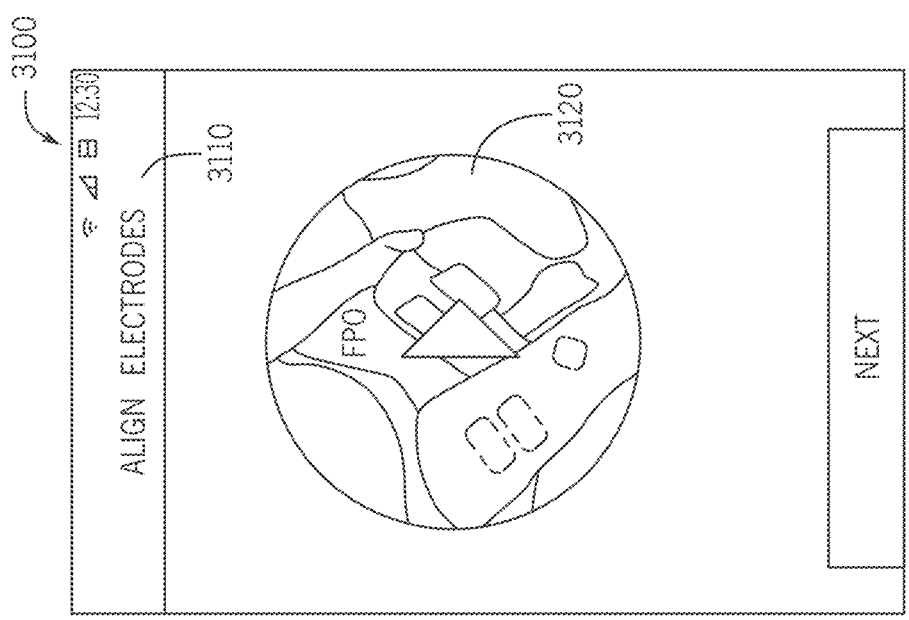
FIG. 31 illustrates a display of a therapy system control GUI in accordance with some embodiments of the invention.

In some embodiments, a selector bar 3040 can be used to exit help or advance to another help step or subject. For example, FIG. 31 illustrates a display 3100 of a therapy system control GUI in accordance with some embodiments of the invention. In some embodiments, display 3100 can include information bar 3110 indicating help for alignment of electrodes. Further, visual indicator 3120 can include a visual display of text, graphics, video, still images or a combination thereof showing or illustrating one or more steps of a fitting procedure for aligning electrodes. In some embodiments, audio information can be played in place of or in addition to text, graphics, video, still images or a combination thereof.

Figure 32:
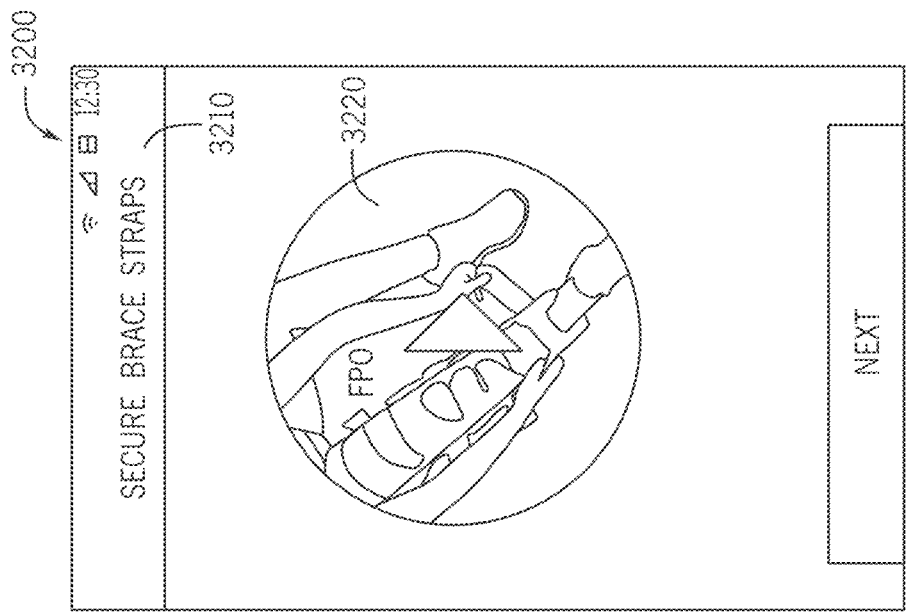
FIG. 32 illustrates a display of a therapy system control GUI in accordance with some embodiments of the invention.

FIG. 32 illustrates a display 3200 of a therapy system control GUI in accordance with some embodiments of the invention. In some embodiments, display 3200 can include information bar 3210 indicating help for securing brace straps. Further, visual indicator 3220 can include a visual display of text, graphics, video, still images or a combination thereof showing or illustrating one or more steps of a fitting procedure for securing brace straps. In some embodiments, audio information can be played in place of or in addition to text, graphics, video, still images or a combination thereof.

FIG. 33 illustrates a display 3300 of a therapy system control GUI in accordance with some embodiments of the invention. In some embodiments, a display 3300 can include information bar 3310 indicating instructions for plugging in the garment controller. Further, A visual indicator 3320 can include a visual display of text, graphics, video, still images or a combination thereof showing or illustrating one or more steps of plugging in the garment controller. In some embodiments, audio information can be played in place of or in addition to text, graphics, video, still images or a combination thereof.

In some embodiments, the GUI can be used to activate the garment. For example, FIG. 34 illustrates a display 3400 of a therapy system control GUI in accordance with some embodiments of the invention. In some embodiments, the display 3400 can include information or action bar 3410 signifying garment activation. In some embodiments, information segment 3420 can include instructions or information related to garment activation status or procedures. In some embodiments, the visual indicator 3425 can include an illustration of the garment requiring activation, and action selector 3430 can include a test garment action icon 3430.

In some embodiments of the invention, the GUI can enable a user to test a garment. For example, FIG. 35 illustrates a display 3500 of a therapy system control GUI in accordance with some embodiments of the invention. In some embodiments, display 3500 information related to the status of various aspects of the user's garment. For example, in some embodiments, function 3515 can include an indicator 3515*a* related to Bluetooth® connection status. Further, function 3520 can include an indicator 3520*a* related to the connection of a controller. Display portions 3600 and 3650 shown in FIG. 36 illustrate different Bluetooth® status and connection states. For example, display portion 3600 includes status 3610 indicating Bluetooth® connection is in process, and display portion 3650 includes status 3625 indicating controller connection is in process.

Figure 37:
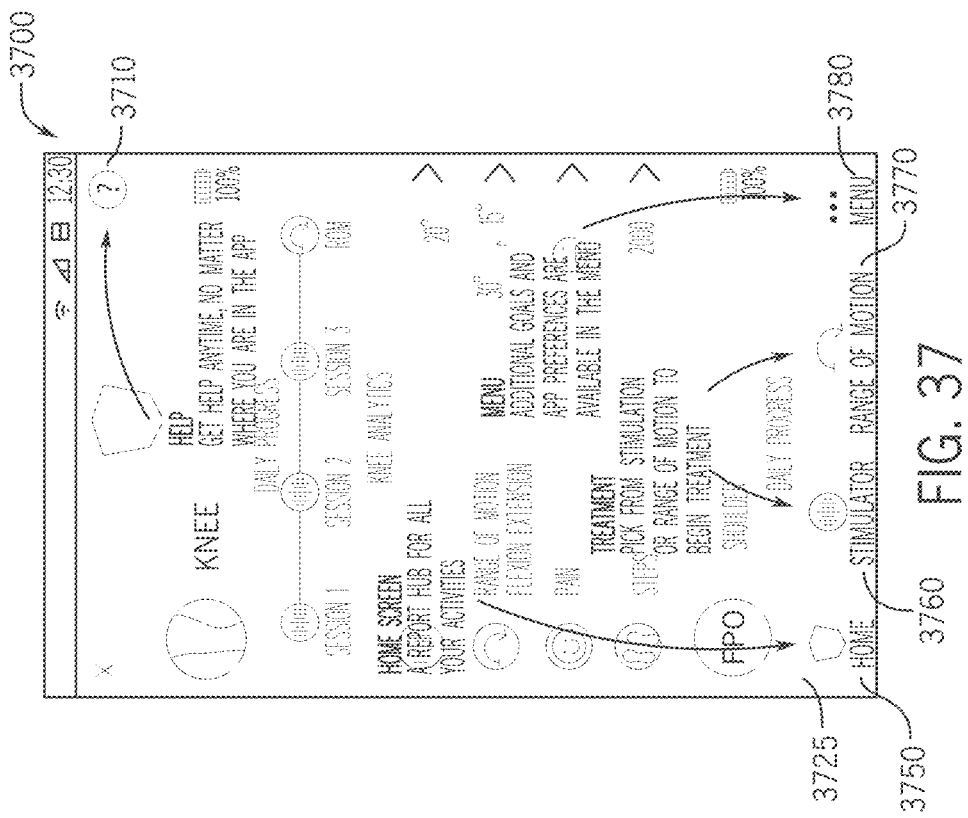
FIG. 37 illustrates a display of a therapy system control GUI in accordance with some embodiments of the invention.

FIG. 37 illustrates a display 3700 of a therapy system control GUI in accordance with some embodiments of the invention. In some embodiments, the display 3700 can include help icon 3710 to enable a user to access one or more help information sections (e.g., such as those described earlier). The display 3700 can also include access bar 3725 including various function or access icons. For example, a home icon 3750 can be used to direct to a home page of the GUI. Further, stimulator icon 3760 or range of motion icon 3770 can be used by a user to select treatment. For example, the stimulator icon 3760 can be used to access one or more functions or status of a stimulator coupled or integrated with the user's garment, and the range of motion icon 3770 can be used to begin treatment designed to enhance a wearer's range of motion. Further, the menu icon 3780 can enable a user to access additional goals and application preferences.

Figure 39:
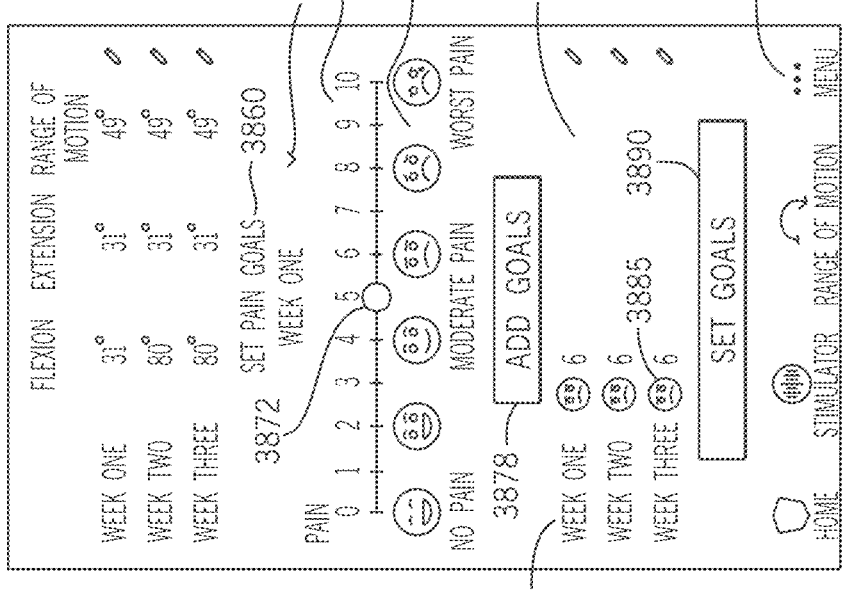
FIG. 39 illustrates a display portion of a therapy system control GUI in accordance with some embodiments of the invention.
Figure 38:
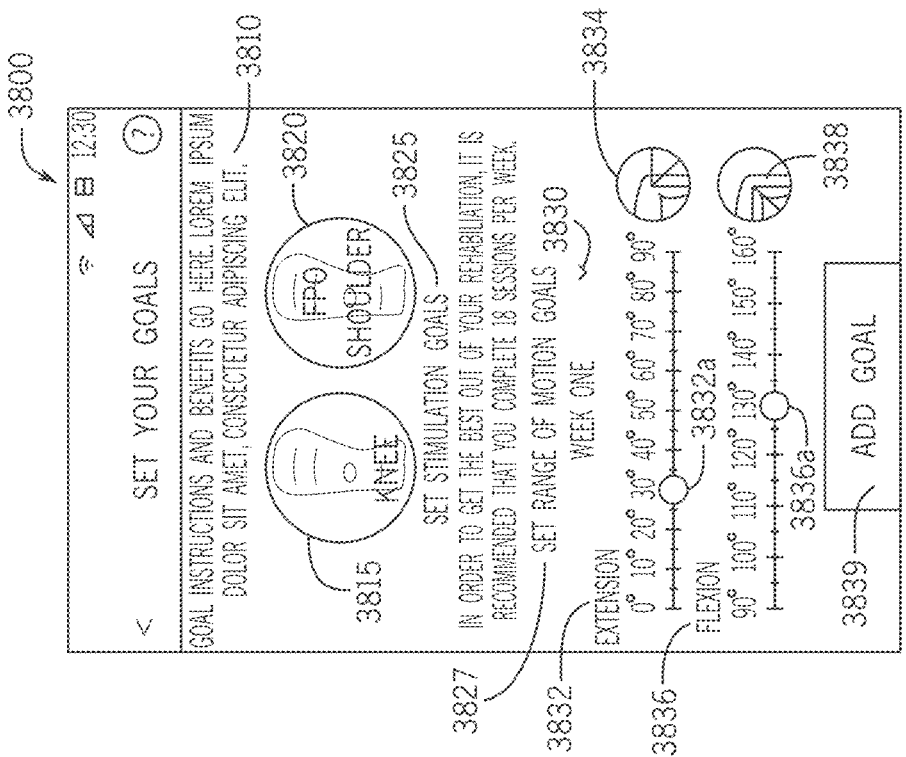
FIG. 38 illustrates a display portion of a therapy system control GUI in accordance with some embodiments of the invention.

In some embodiments, the GUI can enable to set goals for treatment. For example, FIG. 38 illustrates a display portion 3800 of a therapy system control GUI in accordance with some embodiments of the invention. In some embodiments, the display 3800 can include a goal section 3810, set stimulation goal section 3825 including a range of motion goal section 3827. In some embodiments, the goal section 3910 can include one or more icons referring to areas of treatment. For example, icon 3815 can comprise a reference to knee treatment, and icon 3820 can include a reference to shoulder treatment. In some embodiments, the set stimulation goal 3825 section can include advice related to the goal and benefits of the goal, including advised methods of treatment. In some embodiments, the range of motion goal 3827 can include a date selector 3830 configured to enable a user to select a treatment date. In some embodiments, an exercise setting display 3832 can include a moveable indicator 3832*a* for setting a user's target goal related to a body portion displayed as icon 3834. For example, referring to goals related to a user's selection of icon 3815 for knee treatment, exercise setting display 3832 can include a moveable indicator 3832*a* for setting a user's desired target extension angle. Further, exercise setting display 3836 can include a moveable indicator 3836a for setting a user's target goal related to a body portion displayed as icon 3838. In this instance, the exercise setting display 3836 can include a moveable indicator 3836a for setting a user's desired target flexion angle. Further, FIG. 39 illustrates a display portion 3900 of a therapy system control GUI in accordance with some embodiments of the invention. In some embodiments, the display 3900 can include information chart 3850 with goals selected by the user including goals as a function of date as selected by date selector 3830. For example, in some embodiments, user defined flexion, extension, and range of motion goals can be displayed as a function of date.

Some embodiments enable the user to increase the number of goals. For example, in some embodiments, pain reduction goals section 3860 can be used to set target pain reduction goals. In some embodiments, this can be set as a function of date as defined using date selector 3860a. In some embodiments, a pain gauge 3870 can be used to set a target level of pain using moveable indicator 3872. Further, the pain gauge 3870 can include a plurality of icons 3875 representing levels of pain from no pain, to moderate pain, to worst pain. Further, in some embodiments, action indicator 3878 can be used to add a goal, and action selector 3890 can be used to set a goal. In some embodiments, display 3879 can include a display of goals displayed as a function of date 3880 and pain level 3885. At any time, access bar 3892 can be provided to enable a user to access other functions of the system.

Figures 40, 41:
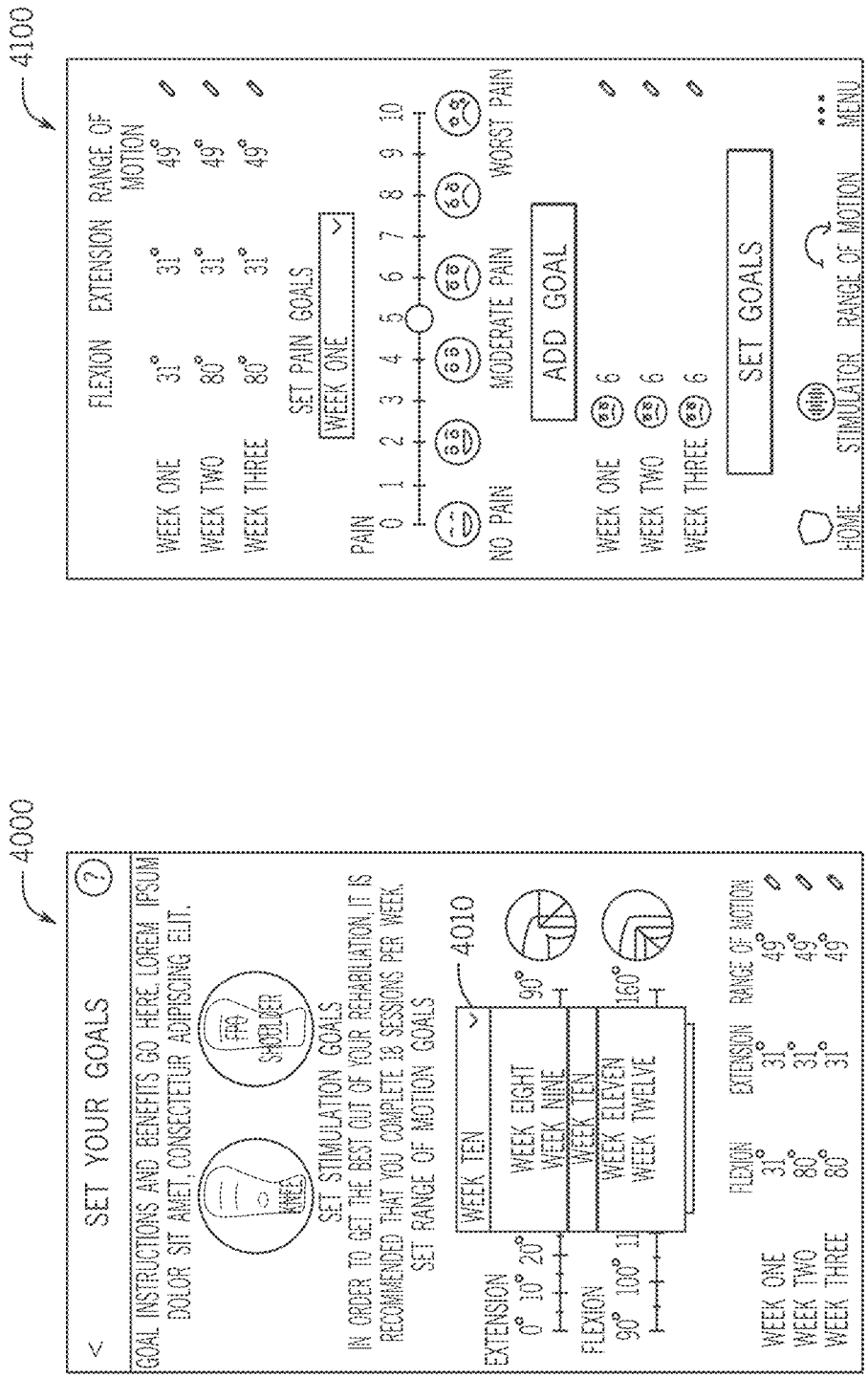
FIG. 40 illustrates a display of a therapy system control GUI in accordance with some embodiments of the invention.
FIG. 41 illustrates a display of a therapy system control GUI in accordance with some embodiments of the invention.

FIG. 40 illustrates a display portion 4000 of a therapy system control GUI in accordance with some embodiments of the invention. In some embodiments, the display 4000 can comprise a drop down menu 4010 configured for selection of a date range, and FIG. 41 illustrates a corresponding display portion 4100 of a therapy system control GUI in accordance with some embodiments of the invention.

Figure 44:
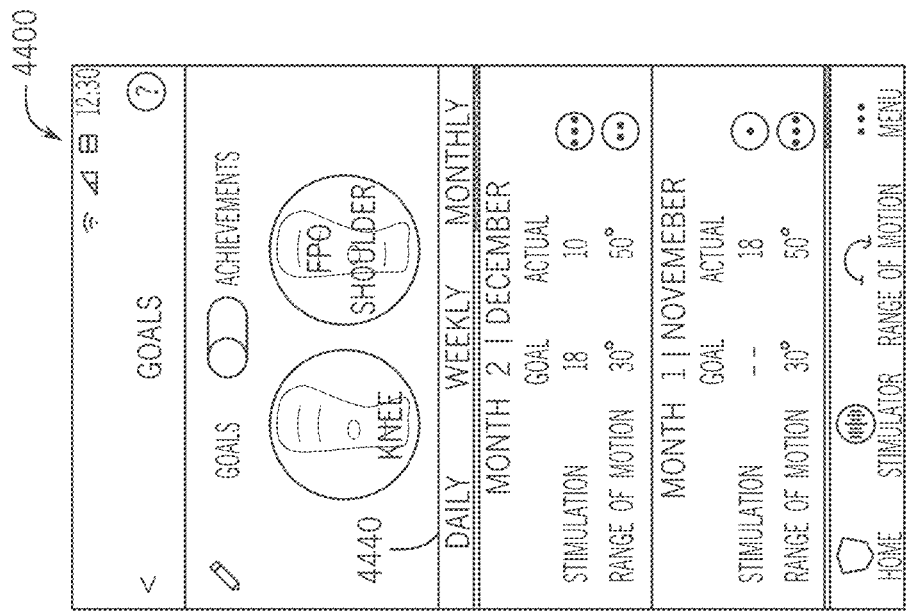
FIG. 44 illustrates a display of a therapy system control GUI in accordance with some embodiments of the invention.

FIG. 42 illustrates a display portion 4200 of a therapy system control GUI in accordance with some embodiments of the invention. In some embodiments, the display portion 4200 can include a selector 4220 configured to enable a user to switch between goals and achievements. In some embodiments, icons 4230 can display one or more body portions related to goals or achievements, and goal and achievements display 4240 can include a display of target goal 4245 versus actual achievements 4250 as function of therapy type 4260 and date 4270 (e.g., such as daily, weekly, and/or monthly goals). In some embodiments, the goal and achievements display 4240 can configure as goals and achievements display 4340 with a daily comparison of goals and achievements (e.g., see FIG. 43 and display portion 4300). FIG. 44 illustrates a display 4400 of a therapy system control GUI in accordance with some embodiments of the invention, and displays a monthly version of the goal and achievements display 4240 (shown as goal and achievements display 4440).

Figure 46:
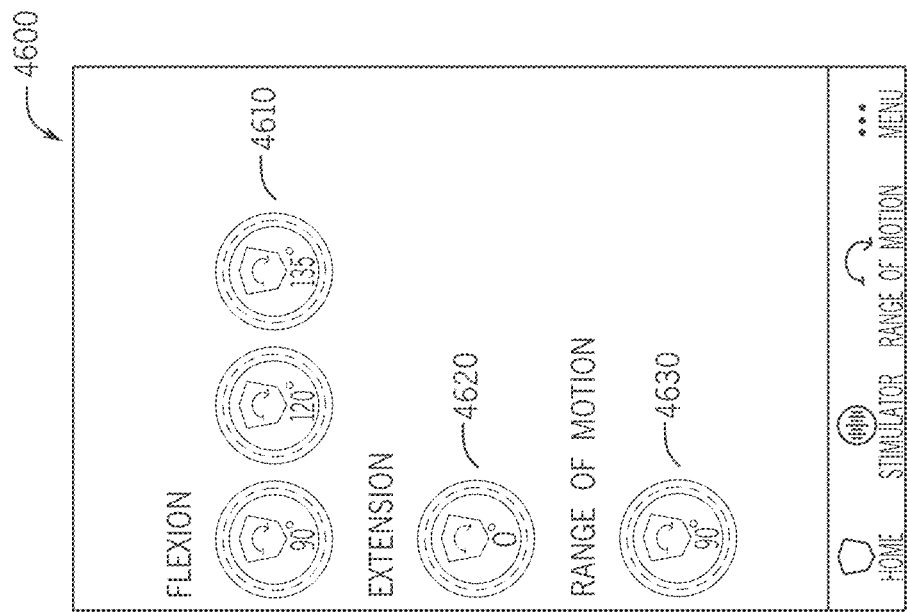
FIG. 46 illustrates a display of a therapy system control GUI in accordance with some embodiments of the invention.
Figure 45:
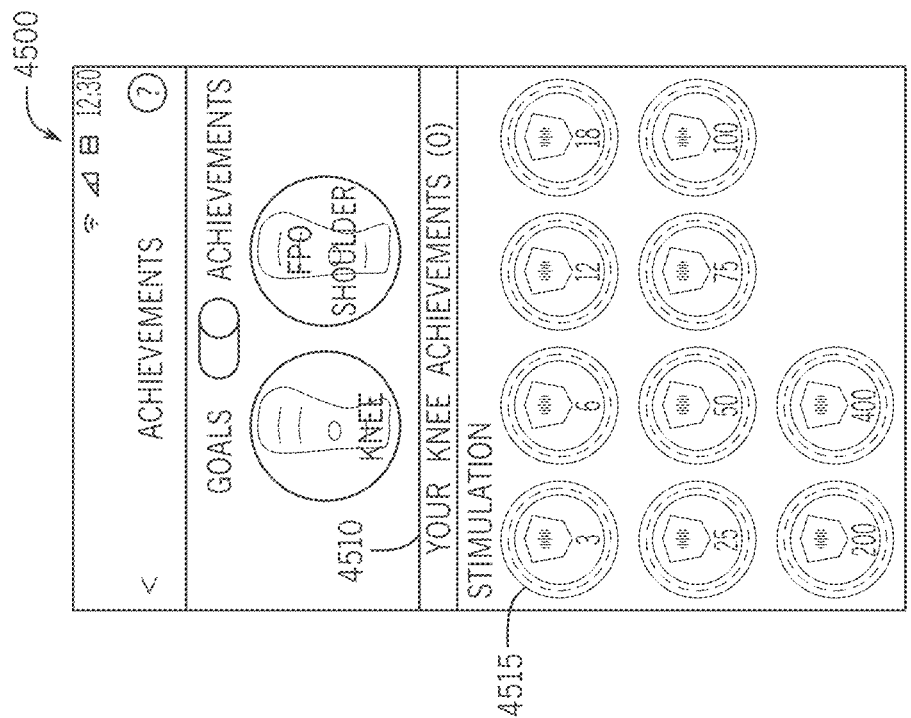
FIG. 45 illustrates a display of a therapy system control GUI in accordance with some embodiments of the invention.
Figure 48:
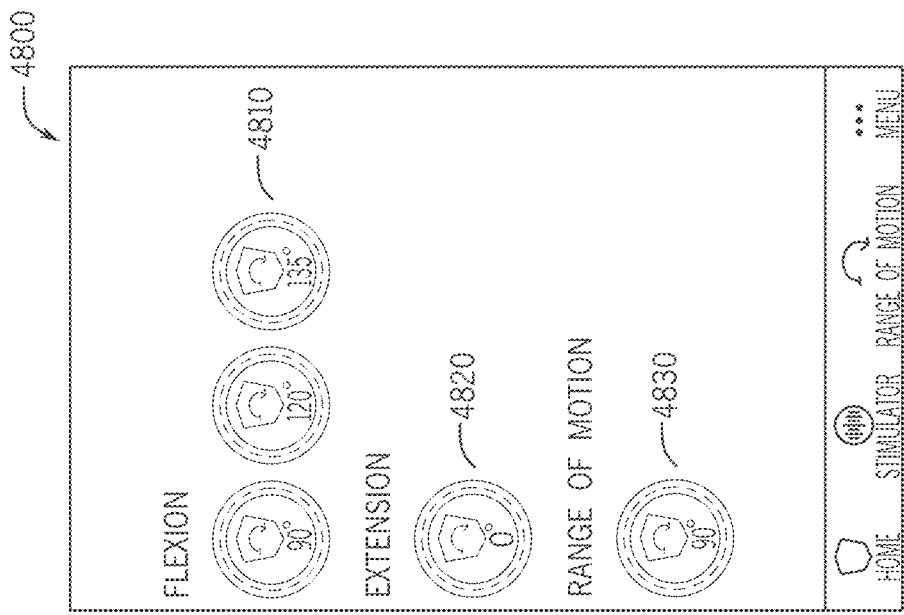
FIG. 48 illustrates a display of a therapy system control GUI in accordance with some embodiments of the invention.
Figure 47:
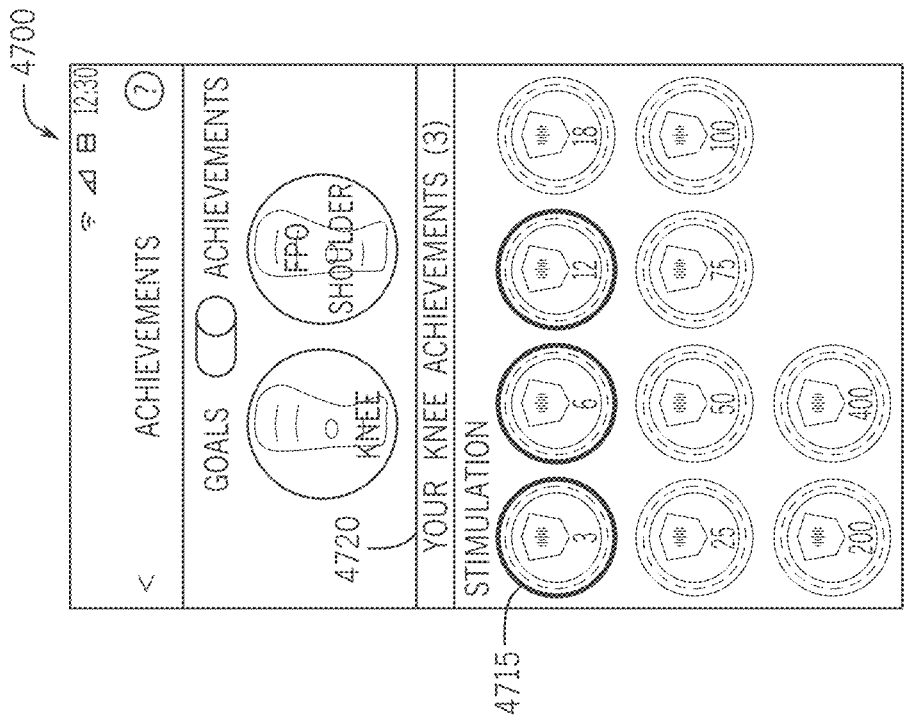
FIG. 47 illustrates a display of a therapy system control GUI in accordance with some embodiments of the invention.
Figure 50:
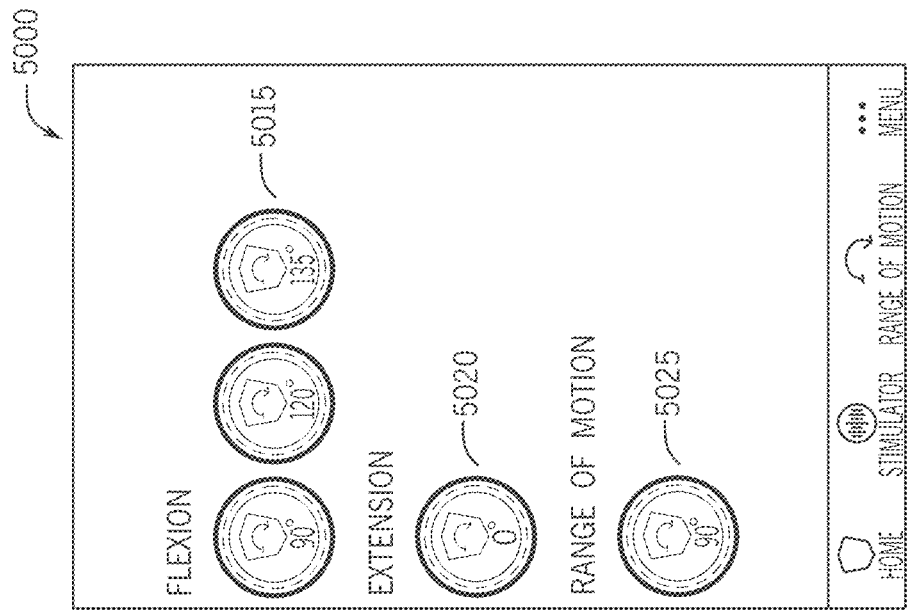
FIG. 50 illustrates a display of a therapy system control GUI in accordance with some embodiments of the invention.
Figure 49:
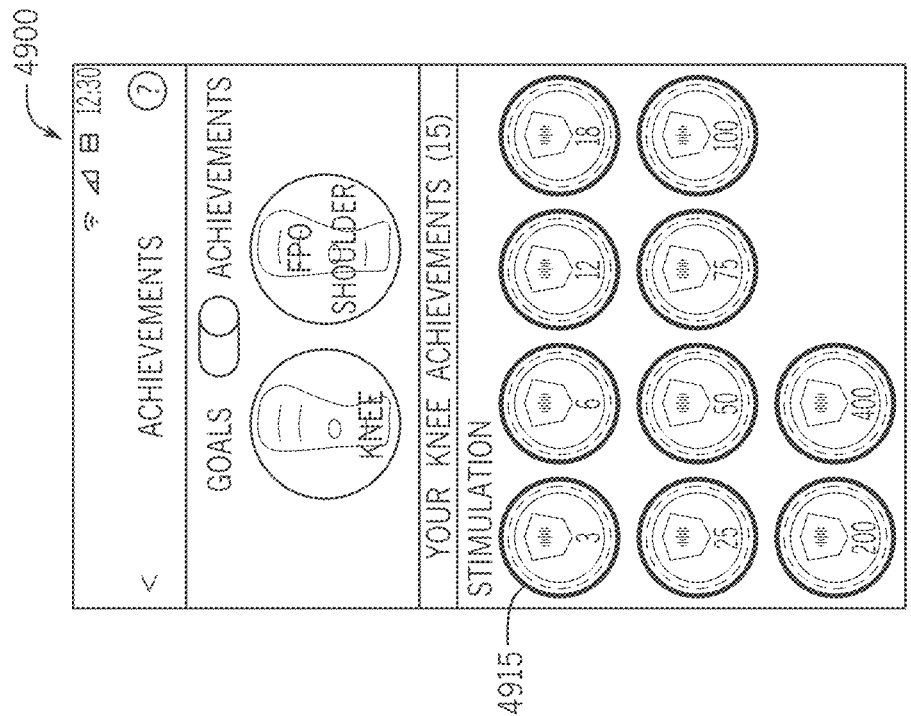
FIG. 49 illustrates a display of a therapy system control GUI in accordance with some embodiments of the invention.

FIG. 45 illustrates a display portion 4500 of a therapy system control GUI in accordance with some embodiments of the invention. In some embodiments, the display portion 4500 can comprise an achievement display 4510 (with selector toggle 4505 set to achievements), where award section 4515 can include one or more achievement awards based on the user reaching or exceeding specific or non-specific goals. Award section 4515 can include awards for stimulation goals. FIG. 46 illustrates a display portion 4600 of a therapy system control GUI in accordance with some embodiments of the invention, and shows awards related to flexion (awards display 4610), extension (awards display 4620), and range of motion (awards display 4630). FIG. 47 illustrates a display portion 4700 of a therapy system control GUI in accordance with some embodiments of the invention, and includes awards display 4715 with awarded awards 4720, and FIG. 48 illustrates a display portion 4800 of a therapy system control GUI in accordance with some embodiments of the invention, and includes awards display 4810, awards display 4820, and awards display 4830. FIG. 49 illustrates a display portion 4900 of a therapy system control GUI in accordance with some embodiments of the invention, and includes awards display 4915 with awards 4918, and FIG. 50 illustrates a display portion 5000 of a therapy system control GUI in accordance with some embodiments of the invention, and shows awards display 5015, awards display 5020, and awards display 5025.

Figure 51:
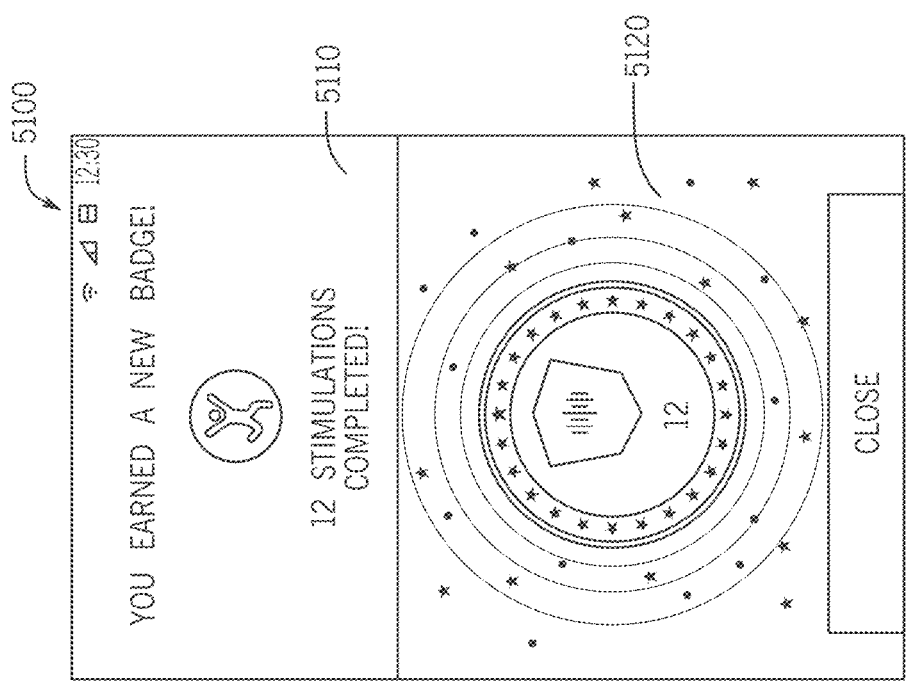
FIG. 51 illustrates a display of a therapy system control GUI in accordance with some embodiments of the invention.

FIG. 51 illustrates a display 5100 of a therapy system control GUI in accordance with some embodiments of the invention. In some embodiments, display 5100 can comprise an announcements or information display 5110 configured to display therapy status (e.g., such as number of stimulations completed). In some embodiments, an award indicator 5120 can be displayed based on the display therapy status.

FIG. 52 illustrates a display 5200 of a therapy system control GUI in accordance with some embodiments of the invention. In some embodiments, display 5200 can be displayed based on a user's selection of access bar 3725. In some embodiments, the display 5200 can include a help icon 5210 to enable a user to access one or more help menus. The display 5200 can also include a garment selector 5220 that can be optionally selected by a user to add additional garments to a stimulation session. Further, in some embodiments, a battery indicator 5230 can be used to show battery charge of the user's device. Stimulation pulse activity can also be monitored. For example, FIG. 53 illustrates a display 5300 of a therapy system control GUI in accordance with some embodiments of the invention. In some embodiments, the display 5300 can include pulse current indicator 5310 and/or pulse level indicator 5320.

Figure 54:
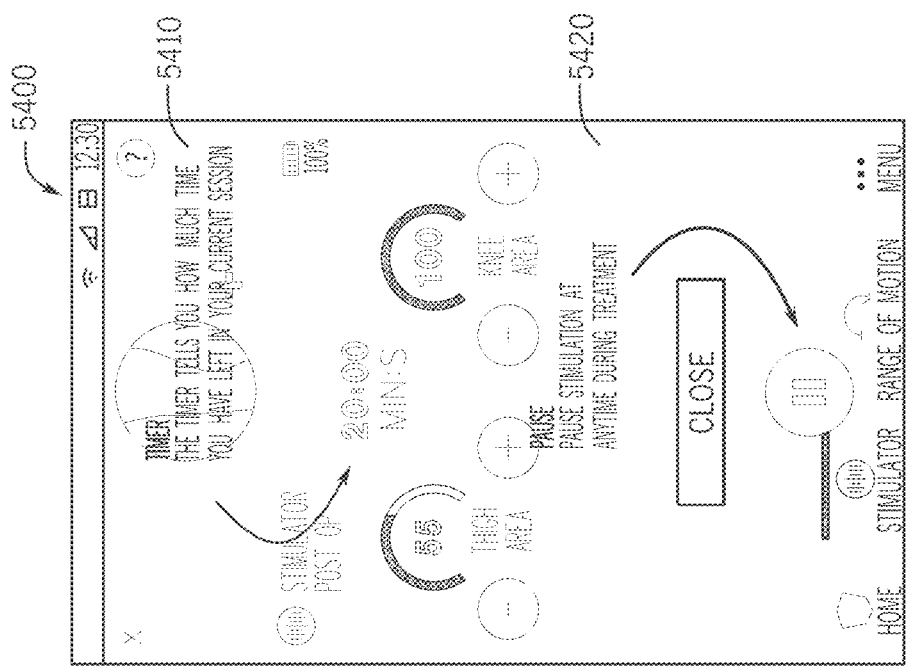
FIG. 54 illustrates a display of a therapy system control GUI in accordance with some embodiments of the invention.

FIG. 54 illustrates a display 5400 of a therapy system control GUI in accordance with some embodiments of the invention. In some embodiments, display 5400 can comprise a timer 5410 that can display time left in a therapy session. Further, some embodiments include a pause selector 5420 configured to enable a user to pause a therapy session.

Figures 55, 56:
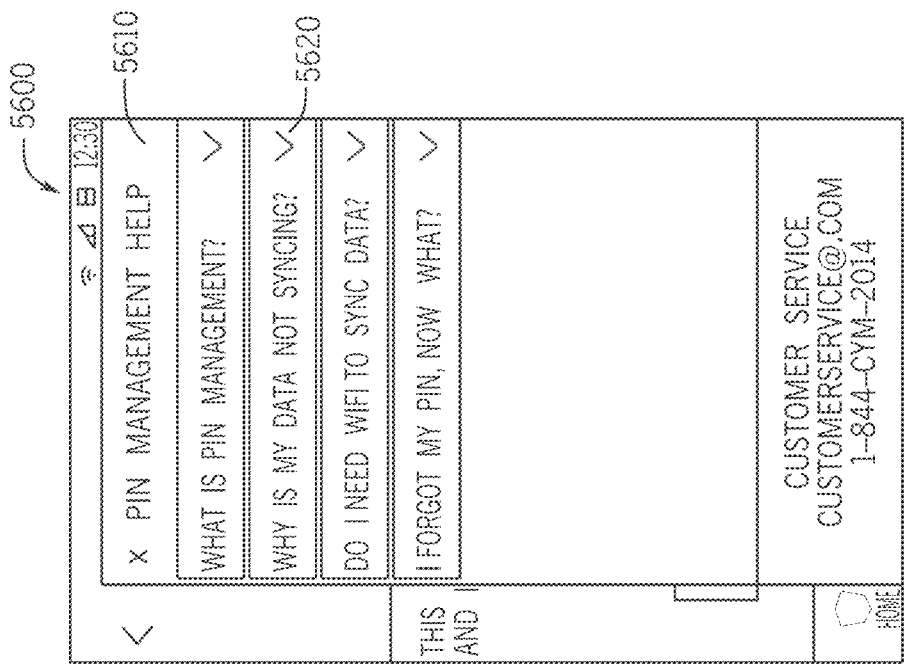
FIG. 55 illustrates a display of a therapy system control GUI in accordance with some embodiments of the invention.
FIG. 56 illustrates a display of a therapy system control GUI in accordance with some embodiments of the invention.

In some embodiments, the GUI can be configured with various help menus that enable a user to select from various help topics. For example, FIG. 55 illustrates a display 5500 of a therapy system control GUI in accordance with some embodiments of the invention. In some embodiments, the display 5500 can comprise a dashboard help section 5510 that includes a menu 5525 that can enable a user to select one or more help subjects. Further, FIG. 56 illustrates a display 5600 of a therapy system control GUI in accordance with some embodiments of the invention. In some embodiments, the display 5600 can include a pin management help section 5610 that can include a menu 5620 configured with selectable topics related to pin management.

Figures 57, 58:
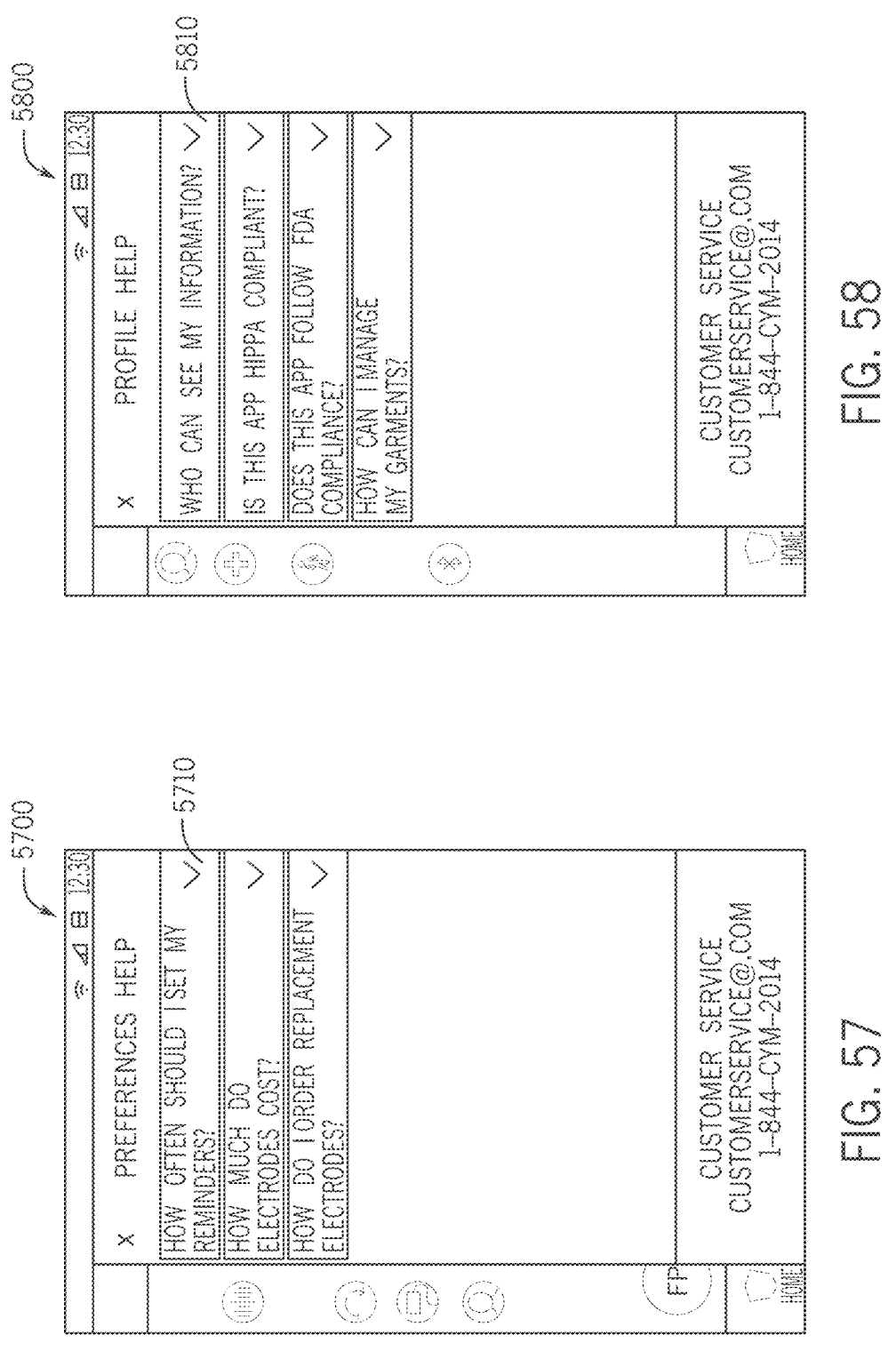
Figure 60:
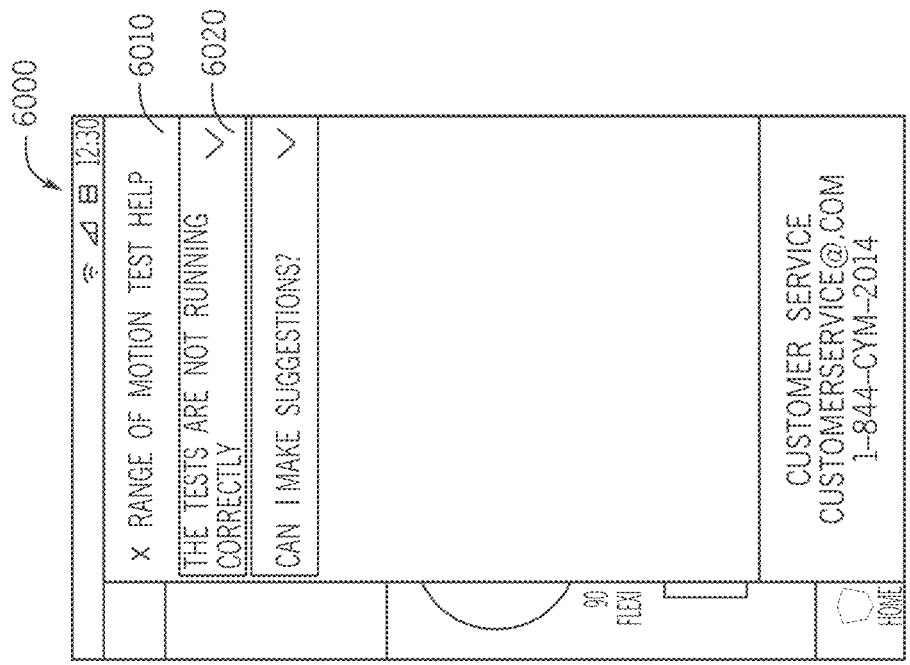
FIG. 60 illustrates a display of a therapy system control GUI in accordance with some embodiments of the invention.
Figure 59:
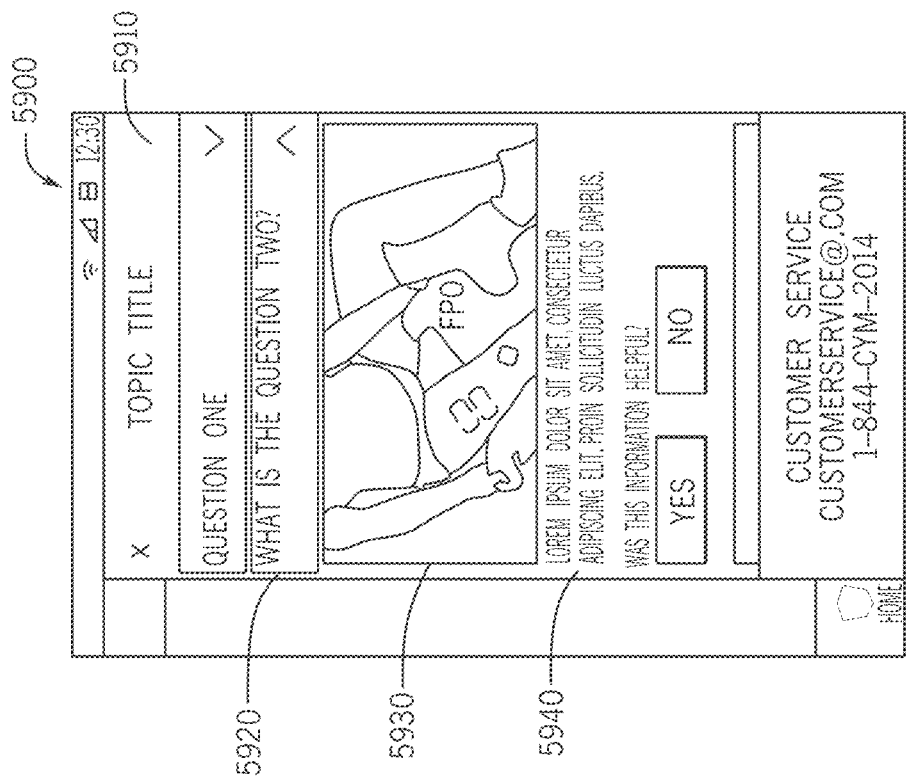
FIG. 59 illustrates a display of a therapy system control GUI in accordance with some embodiments of the invention.

FIG. 57 illustrates a display 5700 of a therapy system control GUI in accordance with some embodiments of the invention. In some embodiments, the display 5700 can include a menu 5710 configured with selectable preferences. Further, FIG. 58 illustrates a display 5800 of a therapy system control GUI in accordance with some embodiments of the invention. In some embodiments, the display 5800 can include a menu 5810 configured with user selectable profile help topics. FIG. 59 illustrates a display 5900 of a therapy system control GUI in accordance with some embodiments of the invention. In some embodiments, the display 5900 can comprise a topic title 5910, and a menu 5920 can include one or more questions related to the topic. The visual window 5930 can include a visual overview of the therapy, and information segment 5940 can include instructions, advice, or other information related to the therapy. Further, FIG. 60 illustrates a display 6000 of a therapy system control GUI in accordance with some embodiments of the invention. In some embodiments, display 6000 can include a range of motion test help 6010 including a menu 6020 configured for selection of at least one help topic.

Figure 62:
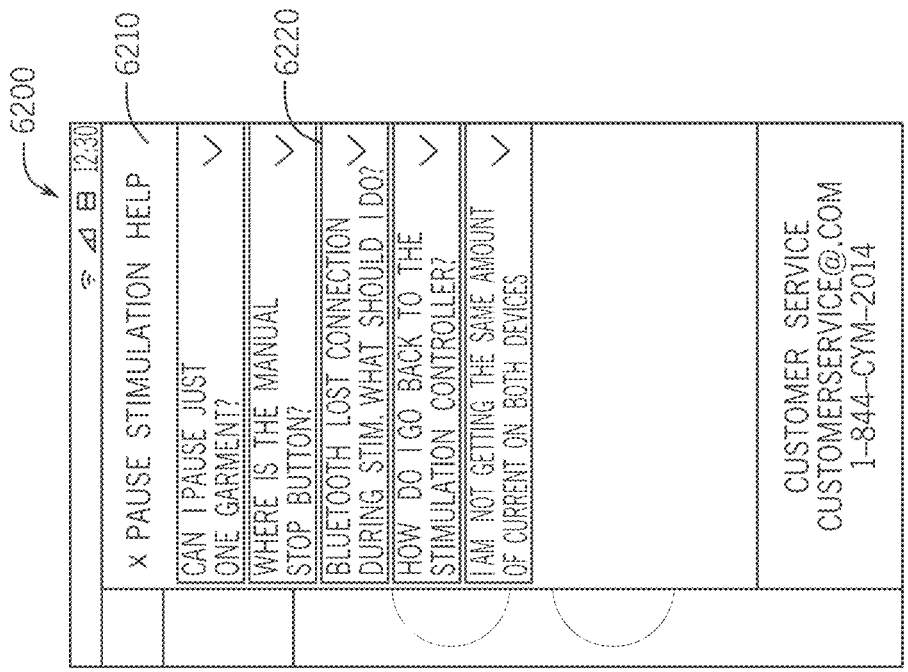
FIG. 62 illustrates a display of a therapy system control GUI in accordance with some embodiments of the invention.
Figure 61:
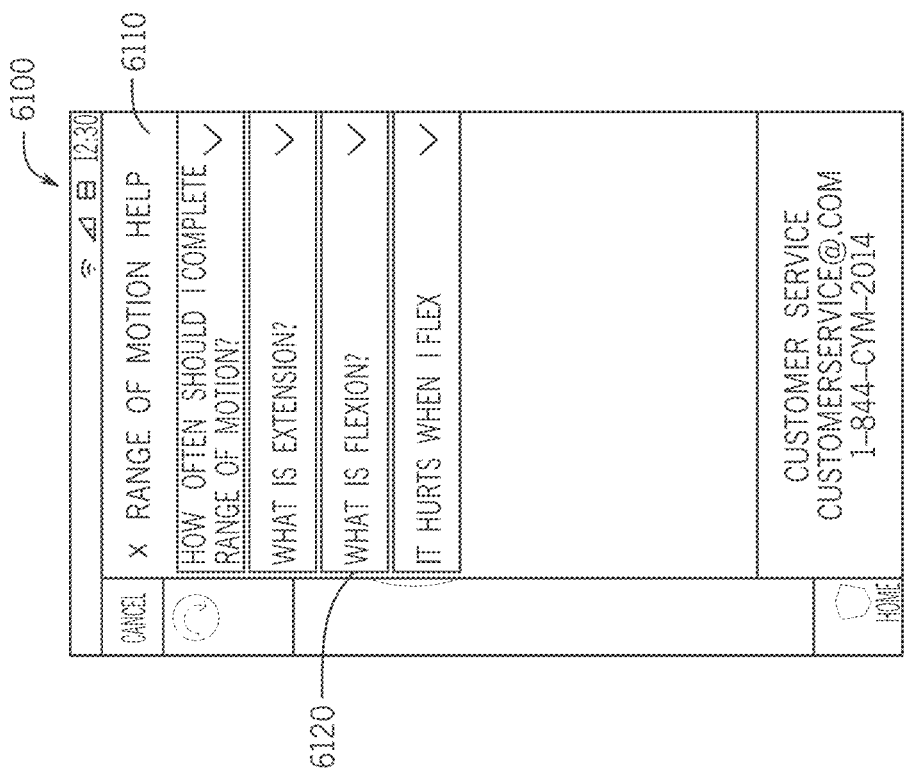
FIG. 61 illustrates a display of a therapy system control GUI in accordance with some embodiments of the invention.
Figure 63:
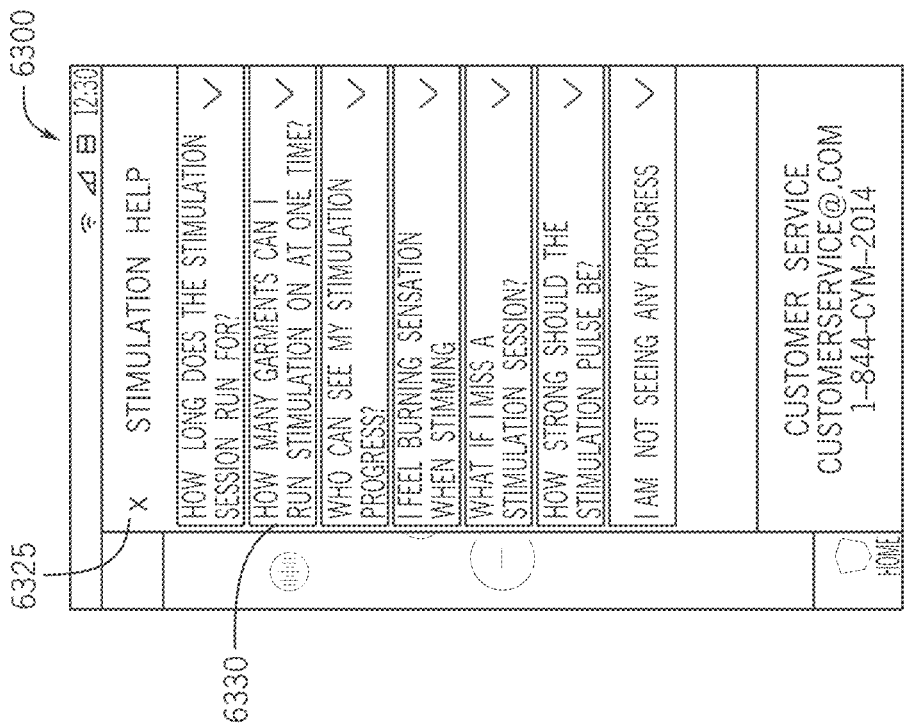
FIG. 63 illustrates a display of a therapy system control GUI in accordance with some embodiments of the invention.

FIG. 61 illustrates a display 6100 of a therapy system control GUI in accordance with some embodiments of the invention. In some embodiments, the display 6100 can comprise a range of motion help 6110 including a menu 6120 comprising a one or more selectable help topics. Further, FIG. 62 illustrates a display 6200 of a therapy system control GUI in accordance with some embodiments of the invention. In some embodiments, the display 6200 can include a pause stimulation help 6210 including a menu 6220 comprising one or more help topics related to stimulation. Further, FIG. 63 illustrates a display 6300 of a therapy system control GUI in accordance with some embodiments of the invention. In some embodiments, the display 6300 can include a pause stimulation help 6325 including a menu 6330 comprising one or more help topics related to stimulation.

Figure 64:
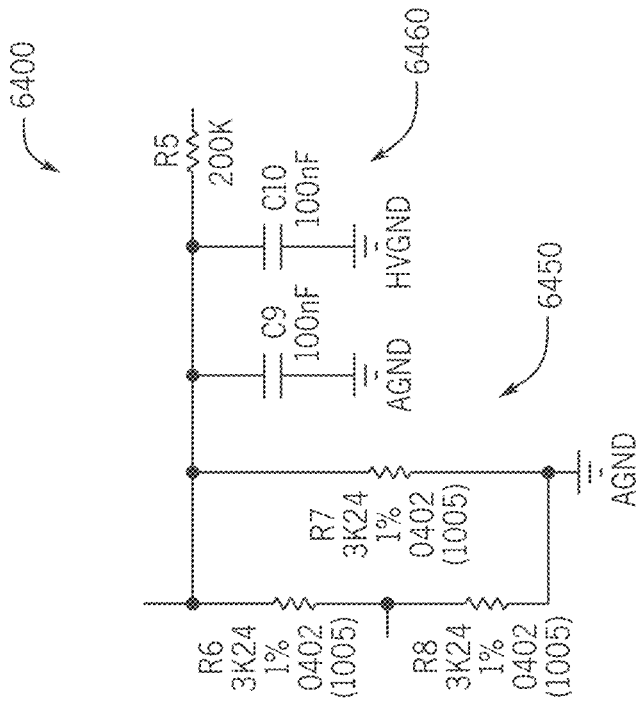
FIG. 64 illustrates a portion of a stimulation circuit of a therapy control system in accordance with some embodiments of the invention.

FIG. 64 illustrates a portion of a stimulation circuit 6400 of a therapy control system in accordance with some embodiments of the invention. In some embodiments, the circuit 6400 can comprise at least one resistor 6450 coupled in parallel with at least one capacitor 6460 coupled to ground. In some embodiments, this configuration enables a comfortable stimulation pulse when delivered to a wearer.

Figure 65B:
Figure 65A:

FIG. 65A illustrates a display 6500 of a therapy control system in accordance with some embodiments of the invention. In some embodiments, the display 6500 can enable a user to enter and/or review personal information within an information window 6510, including, but not limited to height, weight, date of birth, and gender. Further, FIG. 65B illustrates a display 6550 of a therapy control system in accordance with some embodiments of the invention. In some embodiments, the display 6550 can include an information window 6560 that includes at least some of the user's health information. For example, in some embodiments, certain specific information can include information regarding a previous surgery related to current or pending therapy provided by the therapy control system.

Figure 66:
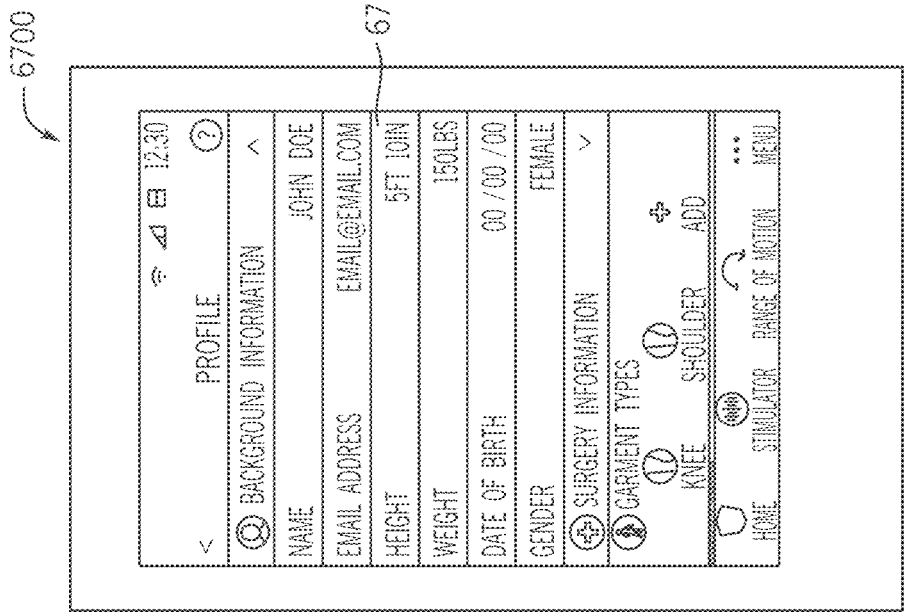
Figure 67:
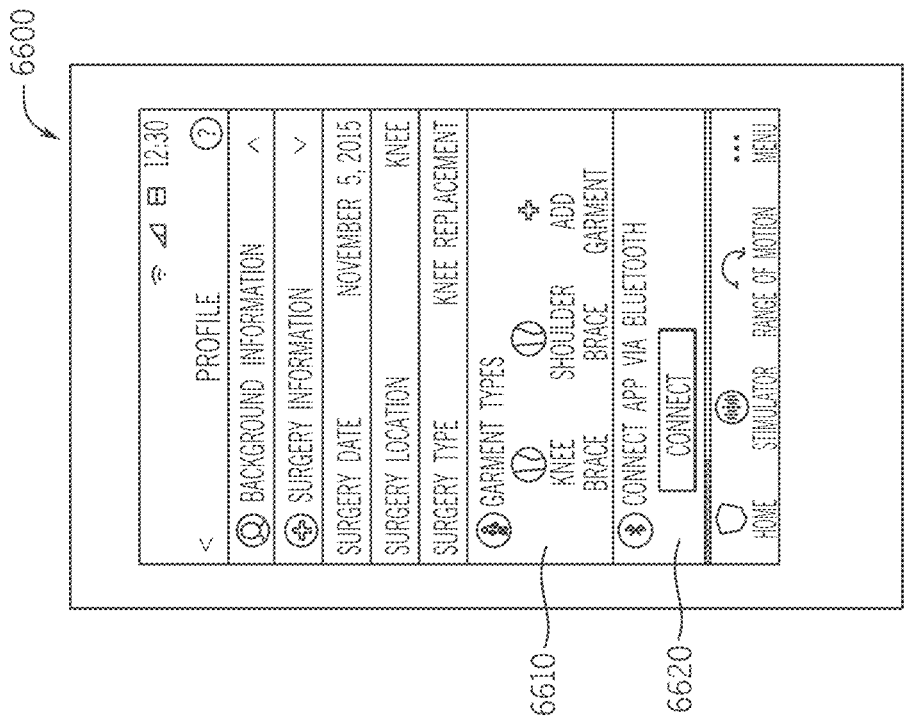

In some embodiments, a user can select a garment type and initiate connection to the garment. For example, FIG. 66 illustrates a display 6600 of a therapy control system in accordance with some embodiments of the invention. In some embodiments, the display 6600 can include a garment type 6610 from which a user can select and add one or more garments for use in one or more therapy sessions. Using Bluetooth® connect 6620, a user can connect to the one or more garments to commence a therapy session. Further, FIG. 67 illustrates a display 6700 of a therapy control system include a scrolled portion of the display 6600 illustrating background information window 6710. In some embodiments, a user can scroll the information window 6710 to access different portions of the window 6710.

In some embodiments, a user can monitor and track therapy sessions using a dashboard. For example, FIG. 68 illustrates a display 6800 of a therapy control system including a dashboard 6810. In this example focused on knee therapy, a progress bar 6820 can comprise the status of therapy including the number of and type of completed or in-progress therapy sessions, and/or the number and type of pending or planned therapy sessions. Further, in some embodiments, one or more access tabs can enable a user to access various therapy session or programs, session or program settings, or data recorded during any session or program. For example, some embodiments include stimulation tab 6830, and/or ROM/flexion/extension tab 6840, pain indicator tab 6850, and steps indicator tab 6860.

Some embodiments include a display of therapy settings that can be configured or reconfigured by a user. For example, FIG. 69 illustrates a display 6900 of a therapy control system in accordance with some embodiments of the invention. In some embodiments, the display 6900 can include a therapy session window 6910 including one or more therapy settings or controls. For example, some embodiments include a thigh area dial 6920, and/or a knee area dial 6930, and/or an area three dial 6940, and/or an area four dial 6950. In some embodiments, any of the dials 6920, 6930, 6940, 6950 can include controls to enable a user to increase or decrease one or more therapy parameters represented by the dials 6920, 6930, 6940, 6950.

Figure 70:
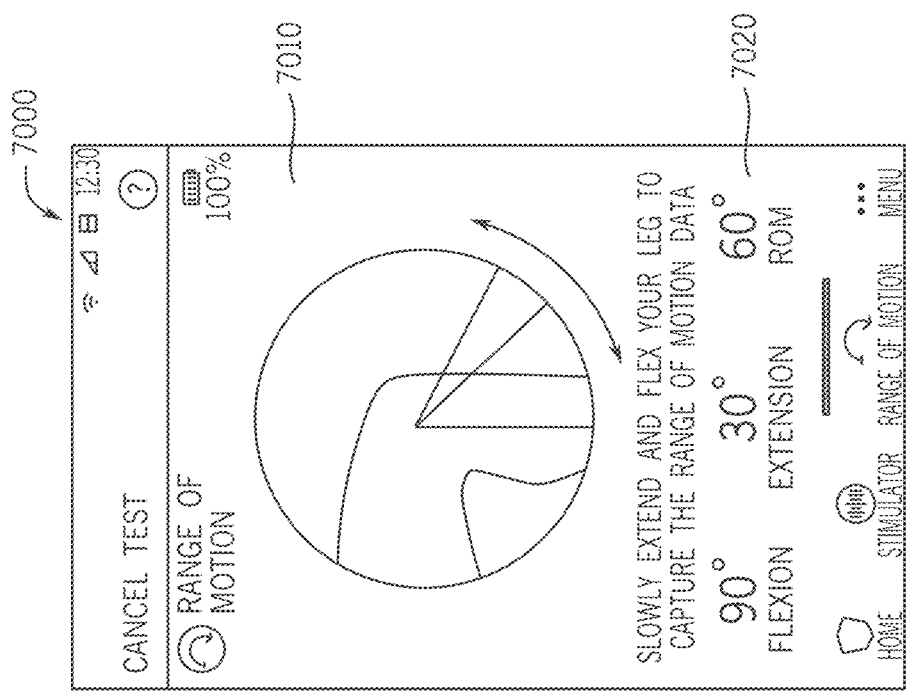

Some embodiments can include a visual or graphical display during a therapy session. For example, FIG. 70 illustrates a display 7000 of a therapy control system in accordance with some embodiments of the invention. In some embodiments, the display 7000 can include a visual guide 7010 providing an anatomical representation of a portion of a user's body undergoing therapy. In some embodiments, the visual guide 7010 can include therapy parameters 7020 from the user including flexion, and/or extension, and/or range of motion data. In some further embodiments, the therapy parameters 7020 can be tracked and plotted over time. For example, FIG. 71 illustrates a display 7100 of a therapy control system in accordance with some embodiments of the invention. In some embodiments, the display 7100 can include a therapy progress plot 7110 illustrating flexion, and/or extension, and/or range of motion data plotted as a function of time. Further, in some embodiments, a details section 7120 can comprises tabulated data of flexion, and/or extension, and/or range of motion data, alongside pain data. Referring to FIG. 72, some further embodiments include a display 7200 with a therapy progress plot 7210 showing progress represented as average power. The display 7200 can also include a therapy dates section 7220 to enable a user to display the plot 7210 with a selected data range. Further, session details section 7230 can include tabulated session data including the start and end time of the therapy session, and the average power from the session.

Figures 73, 74:
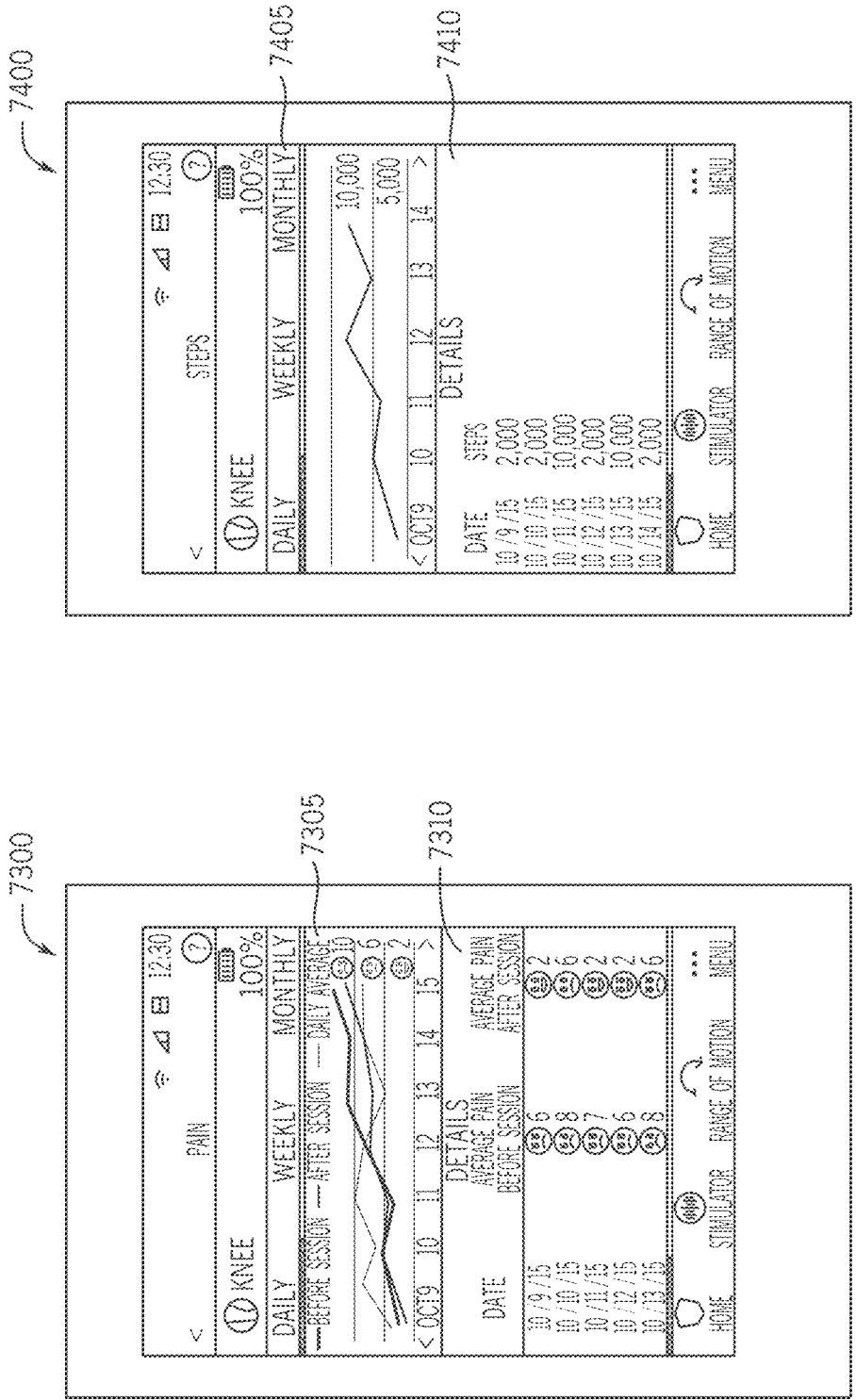

In some embodiments, a user can monitor pain based on timing, session activity or other desired parameters. For example, FIG. 73 illustrates a display 7300 of a therapy control system in accordance with some embodiments of the invention. In some embodiments, the display 7300 can include a therapy pain plot 7305 comprising before session pain, and/or after session pain, and/or a daily average pain level. Further, a session details section 7310 can include tabulated pain data as a function of session date.

In some other embodiments of the invention, a user's steps can be monitored and displayed. For example, FIG. 74 illustrates a display 7400 of a therapy control system in accordance with some embodiments of the invention. In some embodiments, the display 7400 can comprise a therapy steps plot 7405 comprising steps as a function of time, with session details section 7410 providing tabulated steps as a function of date.

Figure 75:
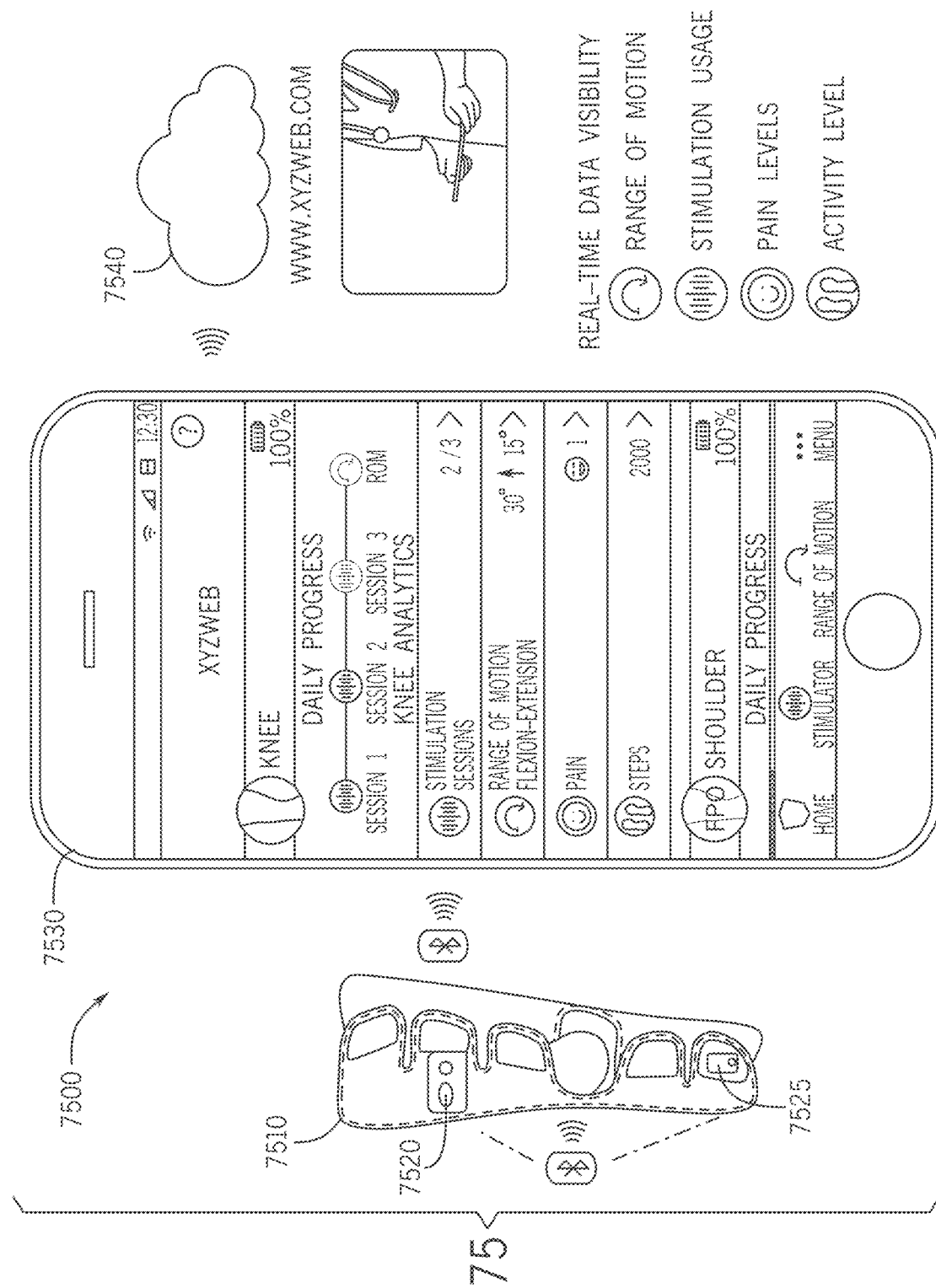
FIG. 75 illustrates a therapy system in accordance with some embodiments of the invention.

As described earlier with respect to FIGS. 3A and 3B, some embodiments include various electronic components can be integrated into one or more modules of a brace system, and the modules can be combined and recombined into various configurations. For example, FIG. 75 illustrates a therapy system 7500 that includes a garment 7510 including a controller 7520 integrated or coupled to the garment 7510. Further, some embodiments include one or more sensor pods 7525 integrated or coupled to the garment 7510. In some embodiments, the controller 7520 includes rechargeable power storage. Further in some embodiments, the sensor pod includes onboard power.

Figure 76:
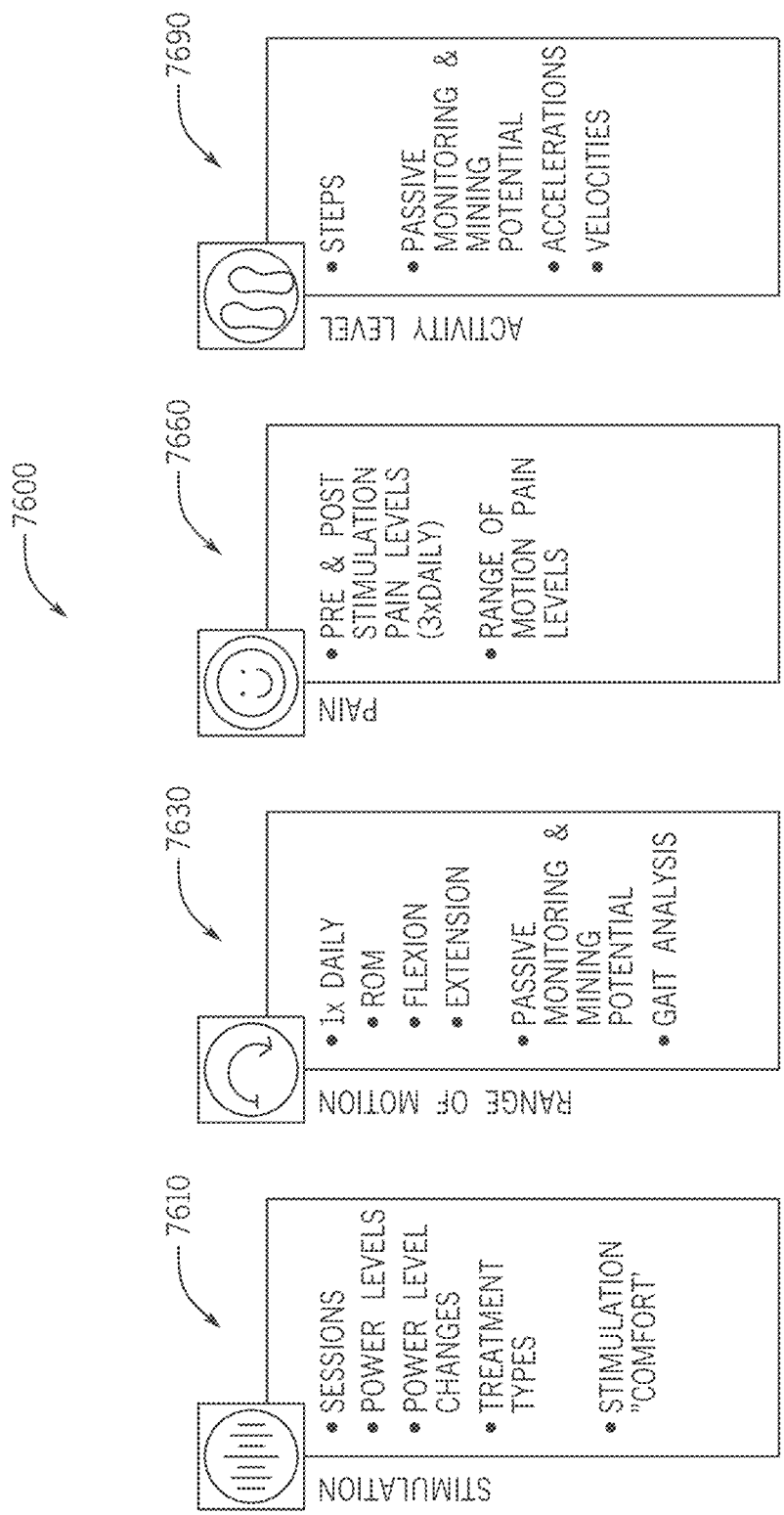
FIG. 76 illustrates data types for the therapy system of FIG. 75 in accordance with some embodiments of the invention.

In some embodiments, one or more sensor pods 7525 can be linked to the controller 7520 using a wired or wireless link. For example, in some embodiments, one or more sensor pods 7525 can be linked to the controller 7520 using a Bluetooth® wireless link. In some embodiments, one or more of the sensor pods 7525 can exchange data with the controller 7520, which can exchange the data, or related data to a user's device such as mobile device 7530. Further, in some embodiments, the mobile device 7530 can exchange the data or related data to an external server system 7540 (e.g., such as a cloud server and/or storage system). In some embodiments, the controller 7520 can be configured to exchange information with the one or more of the sensor pods 7525 and the mobile device 7530 at substantially the same time. Referring to FIG. 76, illustrating data types 7600 for the therapy system of FIG. 75 in accordance with some embodiments of the invention, in some embodiments, exchanged data can include stimulation data 7610, and/or range of motion data 7630, and/or pain data 7660, and/or activity level data 7690. In some embodiments, the stimulation data 7610 can include information or data from one or more therapy sessions, and/or therapy power levels, and/or power level changes, and/or treatment types, and/or stimulation comfort. In some embodiments, the range of motion data 7630 can include range of motion, and/or flexion, and/or extension information or data once daily (or over other time times). In some embodiments, this data can enable passive monitoring and gait analysis. In some further embodiments, the pain data 7660 can include pre and post stimulation pain levels measured and/or distributed at least three times on a daily basis or over other time periods. In some other embodiments, the activity level data 7690 can include the number of steps, accelerations and velocity data.

Some embodiments of the invention analyze activity level data 7690 comprising gait phases using one or more of ROM, accelerometers, gyroscopes, and EMG. Such gait phase analyses can compare post-injury or post-training data to pre-injury, pre-therapy or pre-training baseline data to better evaluate rehabilitation and/or training progress. Gait analyses can also be used alone or with other biometric analyses to identify patients in some embodiments.

In some embodiments, EMG signal and force relationship analyses can also help evaluate rehabilitation and training progress. Some embodiments provide customized therapy and/or training based on feedback from the gait phase or EMG signal and force analyses. In some embodiments, EMG signals are evaluated alternately with stimulation therapy. In some other embodiments, EMG signals are evaluated simultaneously with stimulation therapy using conventional signal filtering and analysis techniques. Finally, in some embodiments, surface EMG analyses can be used to diagnose muscle and/or neurological disease characteristics.

Figure 77:
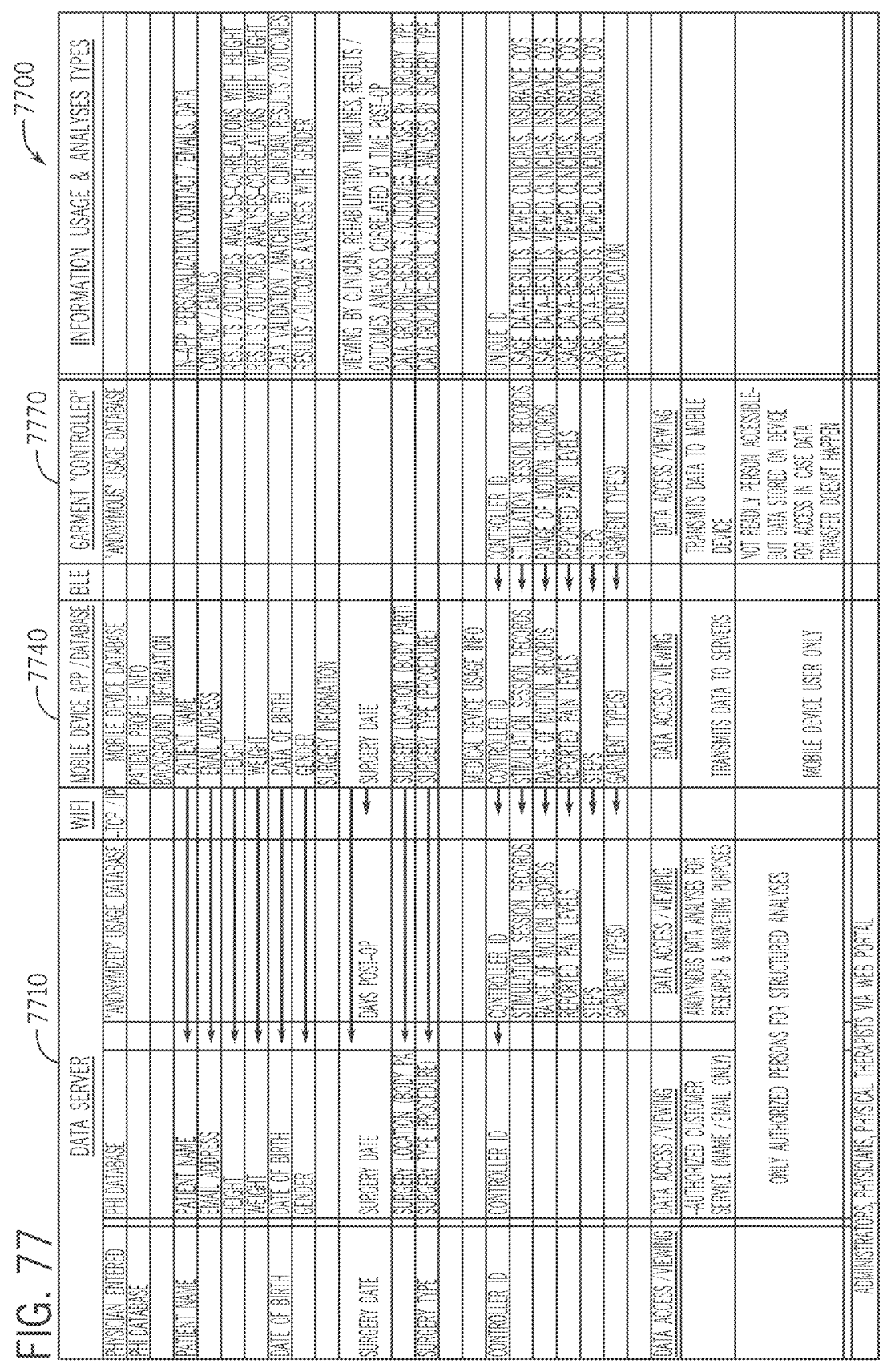

FIG. 77 illustrates data categories 7700 exchanged between and stored within components of the therapy system of FIG. 75 in accordance with some embodiments of the invention. For example, some embodiments include server data categories 7710 comprising data or information exchanged between and/or stored on a server such as where the mobile device 7530 can exchange the data or related data to an external server system 7540 (e.g., a cloud server and/or storage system). Some embodiments also include mobile device application data categories 7740 comprising data exchanged between and/or stored on the a user's device such as mobile device 7530. Further embodiments include garment controller data categories 7770 comprising data exchanged between and/or stored on a garment controller such as controller 7520. In some embodiments, any of the data categories can include a read/write access setting restricting access or providing a level of access. In some embodiments, the read/write access protocols and method of data transfer can be set HIPAA compliance.

Figure 78:
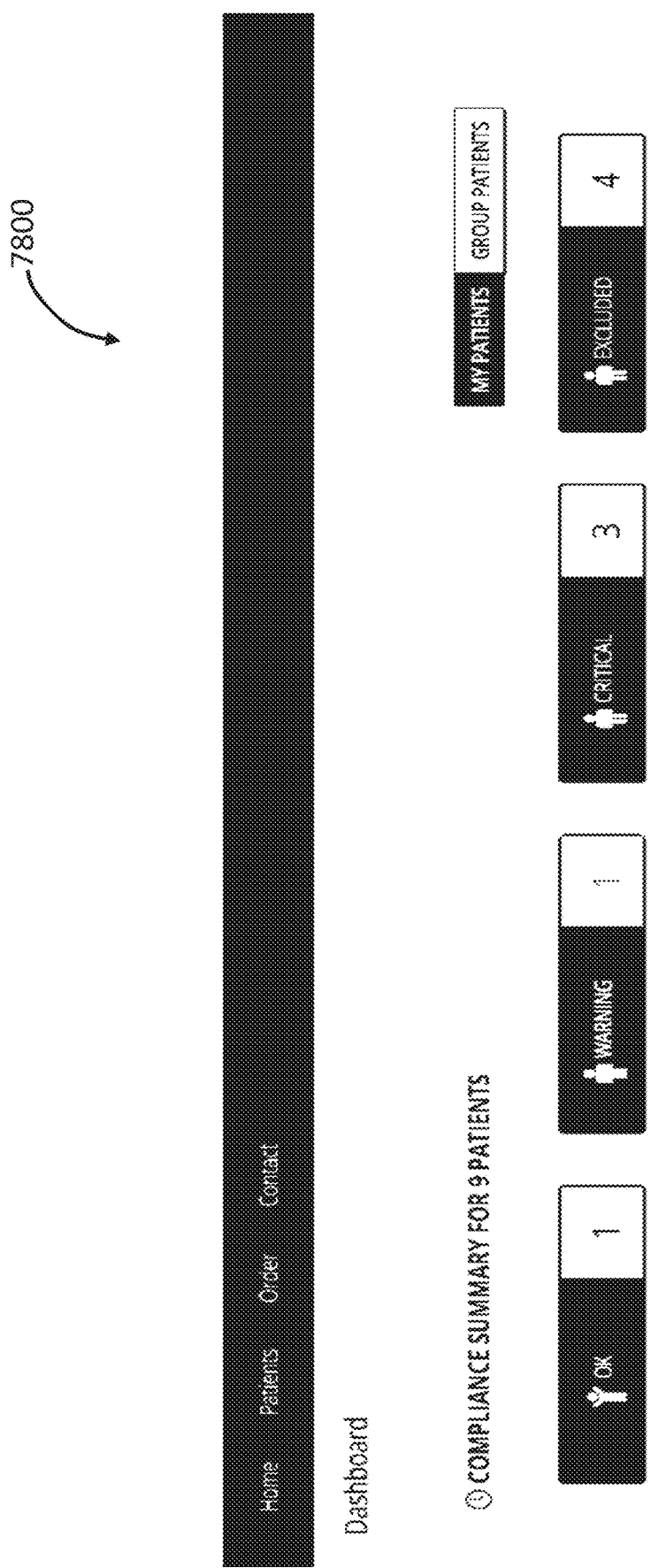
FIG. 78 illustrates a portion of a provider portal dashboard in accordance with some embodiments of the invention.

In some embodiments, a healthcare provider can log into a physician portal of the system (website or software application, mobile app, etc.) In some embodiments, the website can allow the provider to register for an account. In some embodiments, the website can allow a provider to add a device (patient) to his patient list via a unique device ID. In some embodiments of the invention, the website can interact with a cloud server to display a physician's patient data. In some embodiments, a portal dashboard can allow a healthcare provider to view his/her patients or the group's (healthcare practice's) patients. In some embodiments, the system can allow a healthcare providers to customize criteria for categorizing patients (e.g., using red/yellow/green/excluded category types), etc. In some embodiments, the system can utilize push alerts (email, SMS, secure messages, etc.) via customizable criteria sent to healthcare provider to notify if patient's progress is outside of desired zones or at risk for re-admissions. For example, FIG. 78 illustrates a portion of a provider portal dashboard 7800 including categorization of patients based on physician customizable criteria so that physician can receive alerts based on his/her preferences. For example, a compliance summary for a patient can include an example embodiment such as an "ok" compliance alert that is colored green. In a further embodiments, a "warning" alert can be colored yellow. In another embodiment, a "critical" alert can be colored red, and an "excluded" alert can be colored black or grey. One of ordinary skill in the art can recognize that other colors, images, graphics, animations, or combinations thereof can be used to represent the compliance summary.

Figure 79:
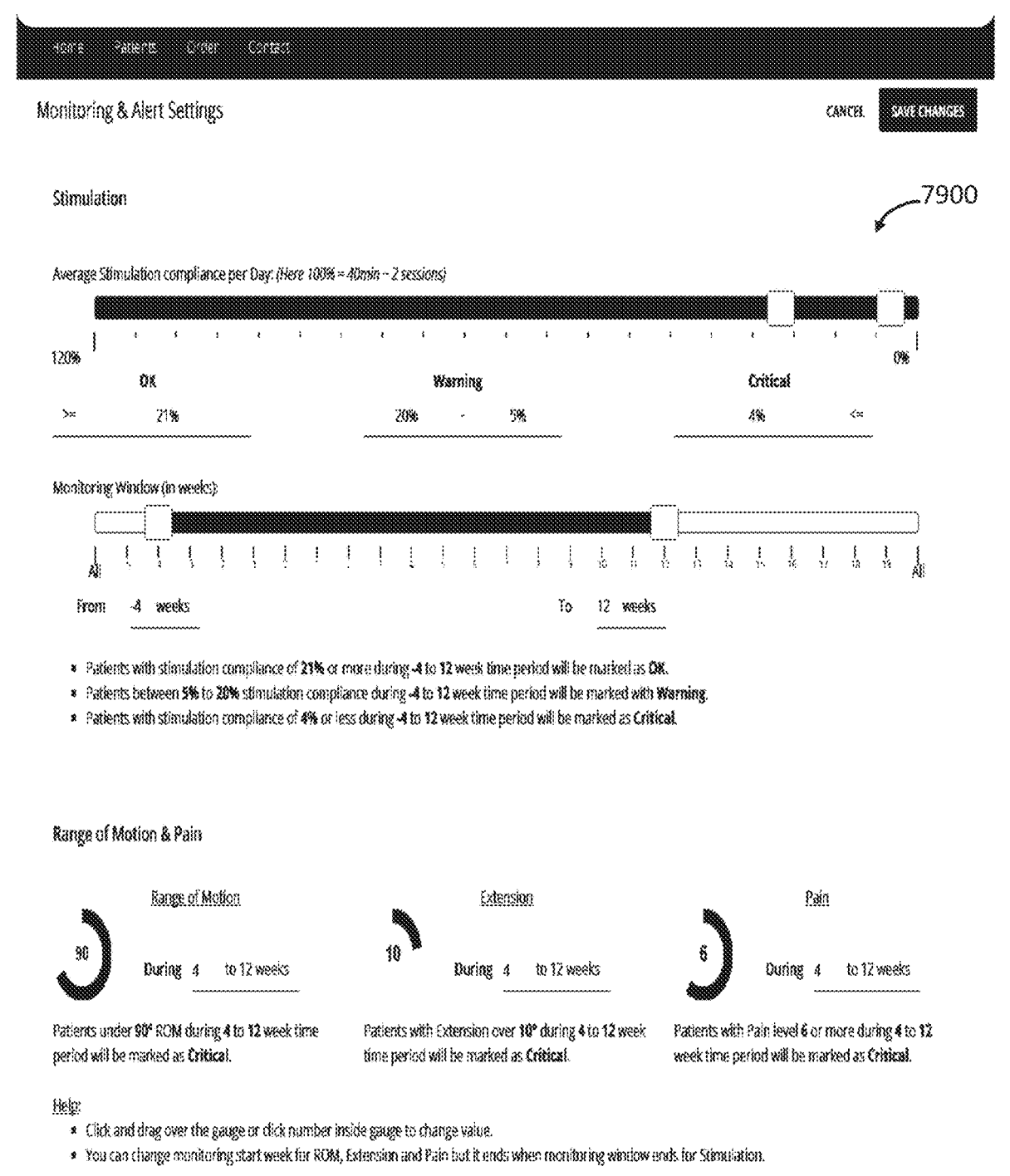

FIG. 79 illustrates a customizable panel and alerts window 7900 of the provider portal dashboard in accordance with some embodiments of the invention. In some embodiments, the window 7900 can comprise a customization panel for categorization & alerts including, but not limited to, a monitoring (time) window (pre-op, post-op, etc.), and/or usage/compliance rates, and/or ROM, and/or extension, and/or pain values.

Figure 80:
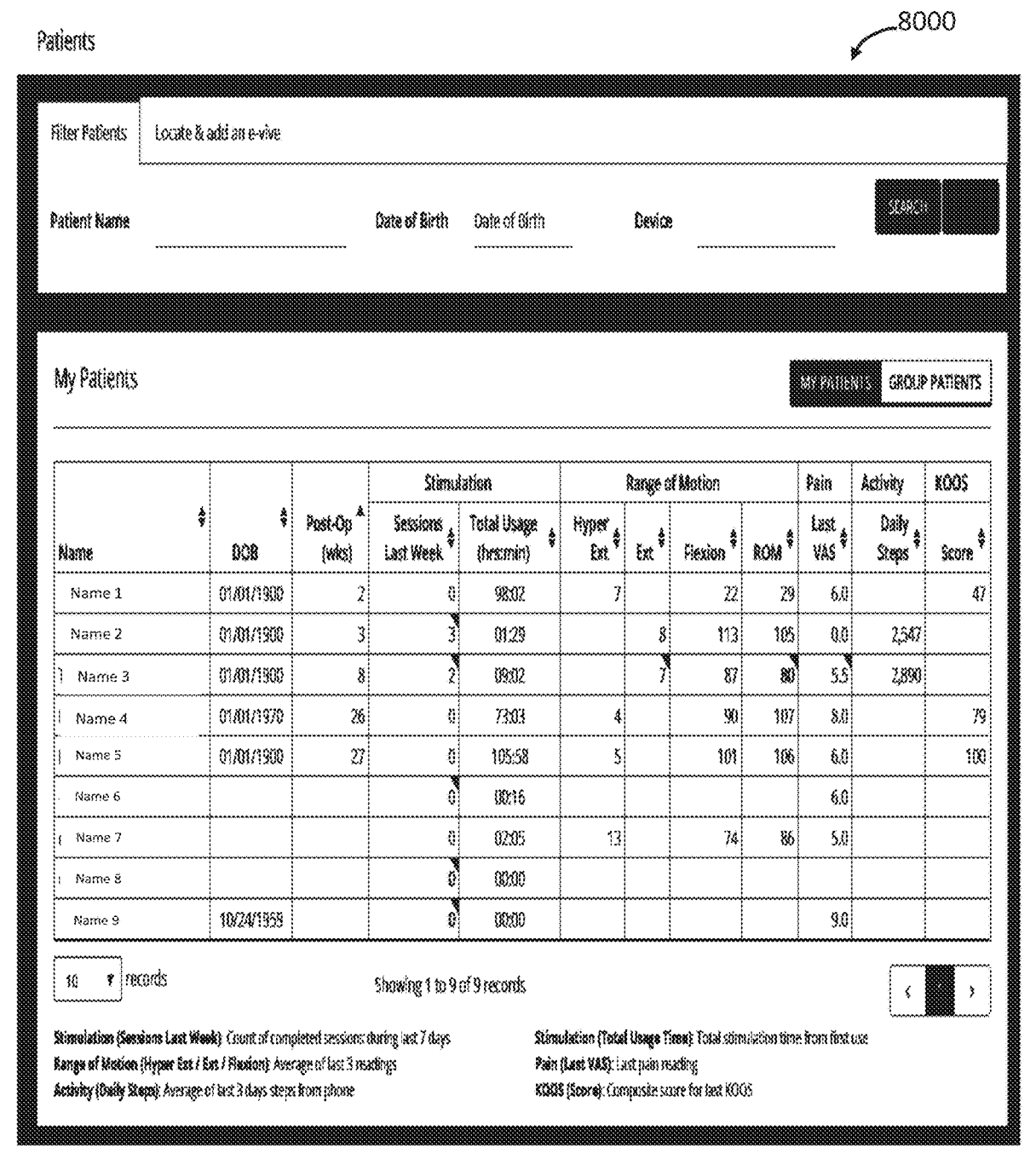

In reference to FIG. 80, some embodiments include a provider portal patient list window 8000 that can be used to provide a patient list with visible flags indicating categorization of patients based on provider's customized criteria. In some embodiments, the provider portal patient list window 8000 can include an ability to search/filter/sort records, and/or to add devices/patients to a patient list. In some embodiments, the window 8000 can be customized to provide a "my patients" view and/or a "group patients" view.

Figure 81:
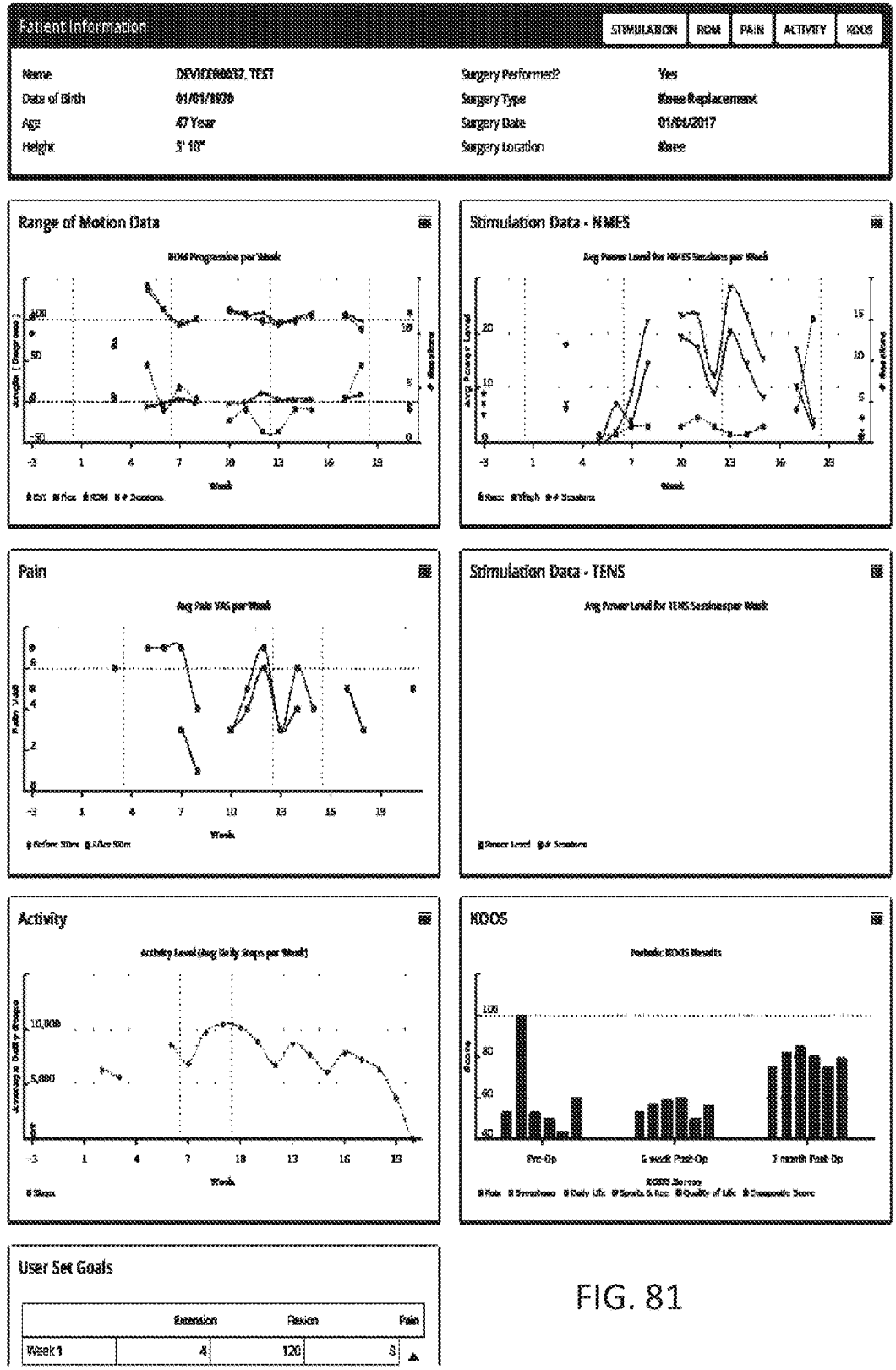
FIG. 81 illustrates a patient overview window in accordance with some embodiments of the invention.
Figure 82:
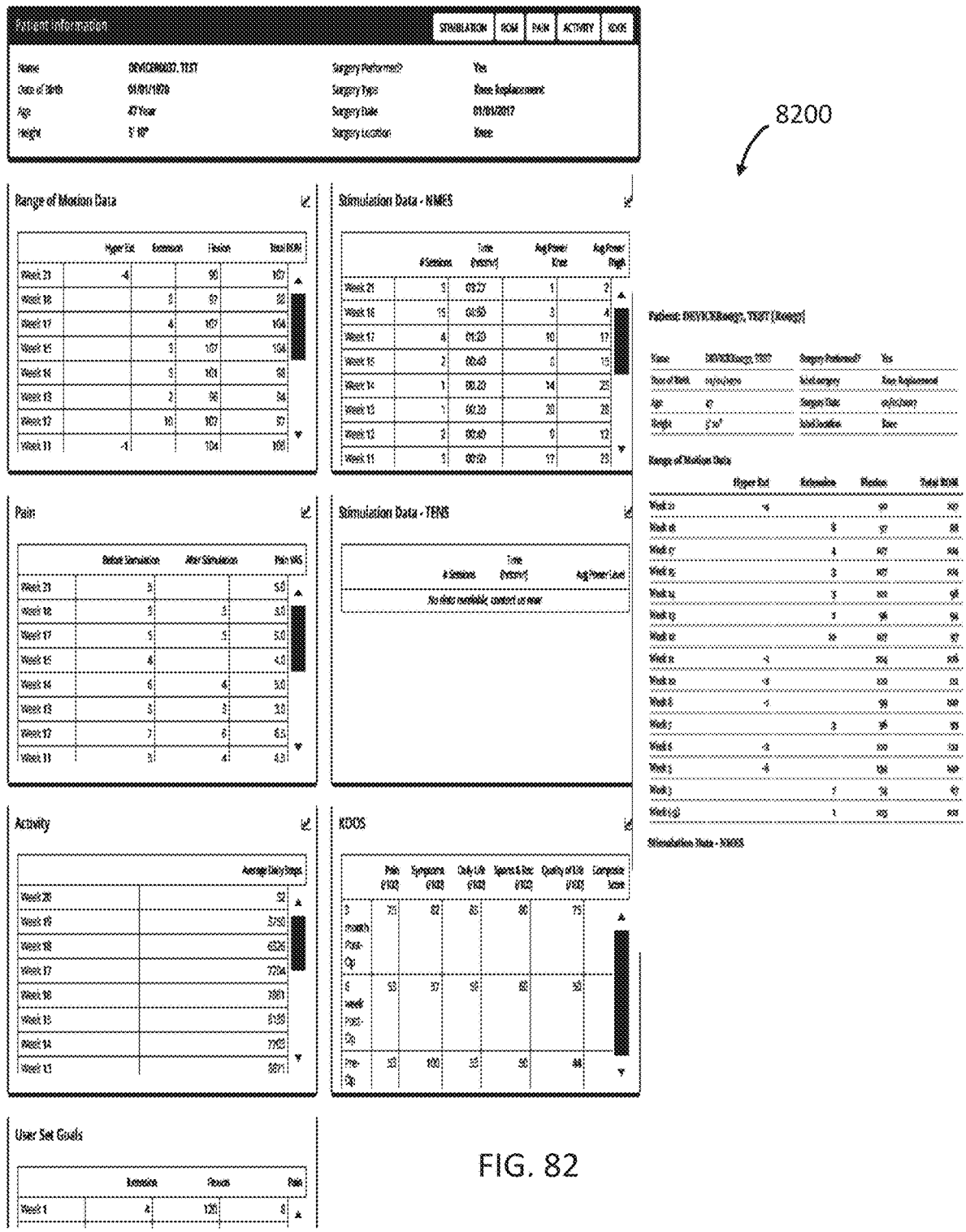
FIG. 82 illustrates a tabular view of a patient overview window in accordance with some embodiments of the invention.
Figures 83A, 83B:
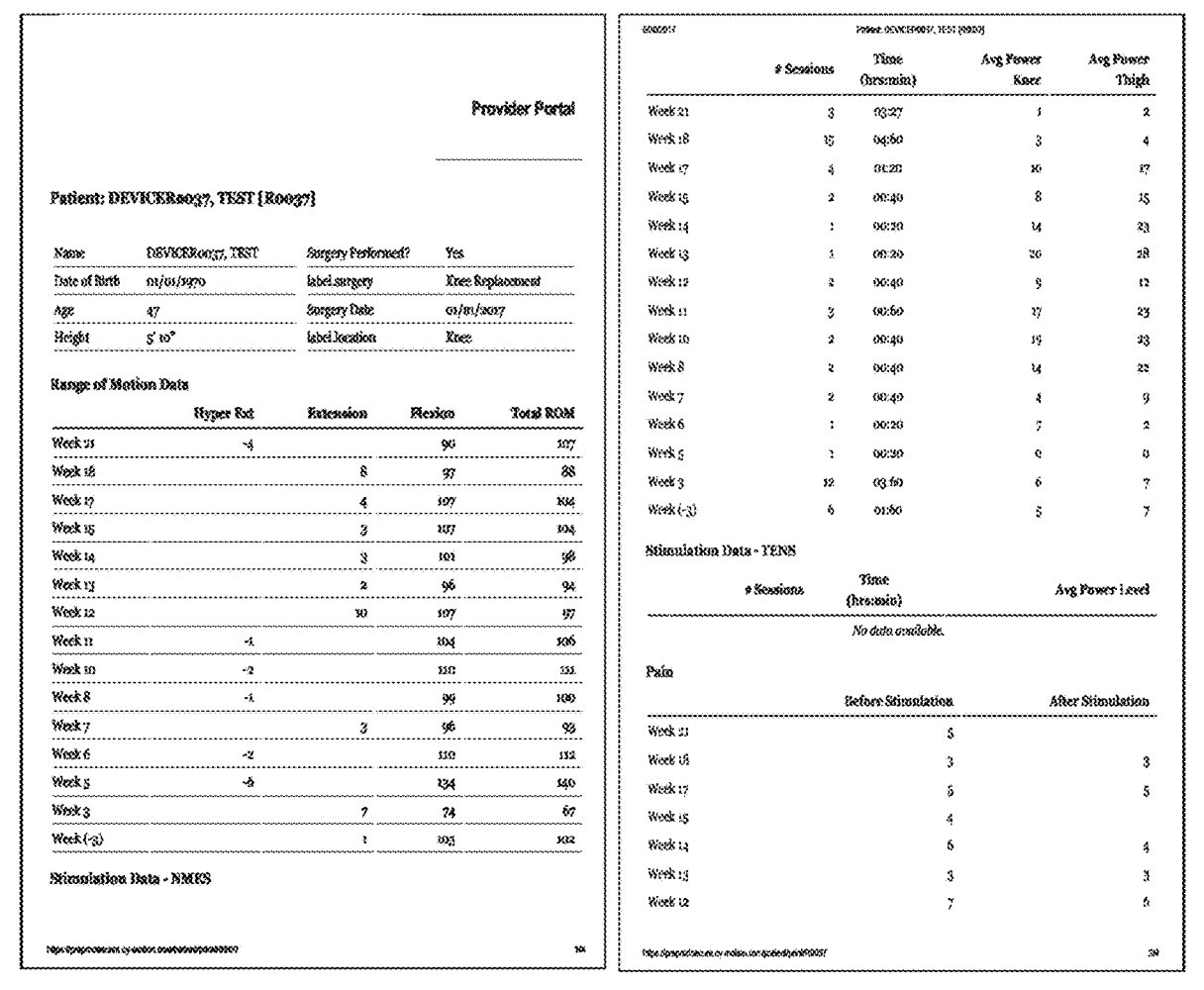
Figures 84A, 84B:
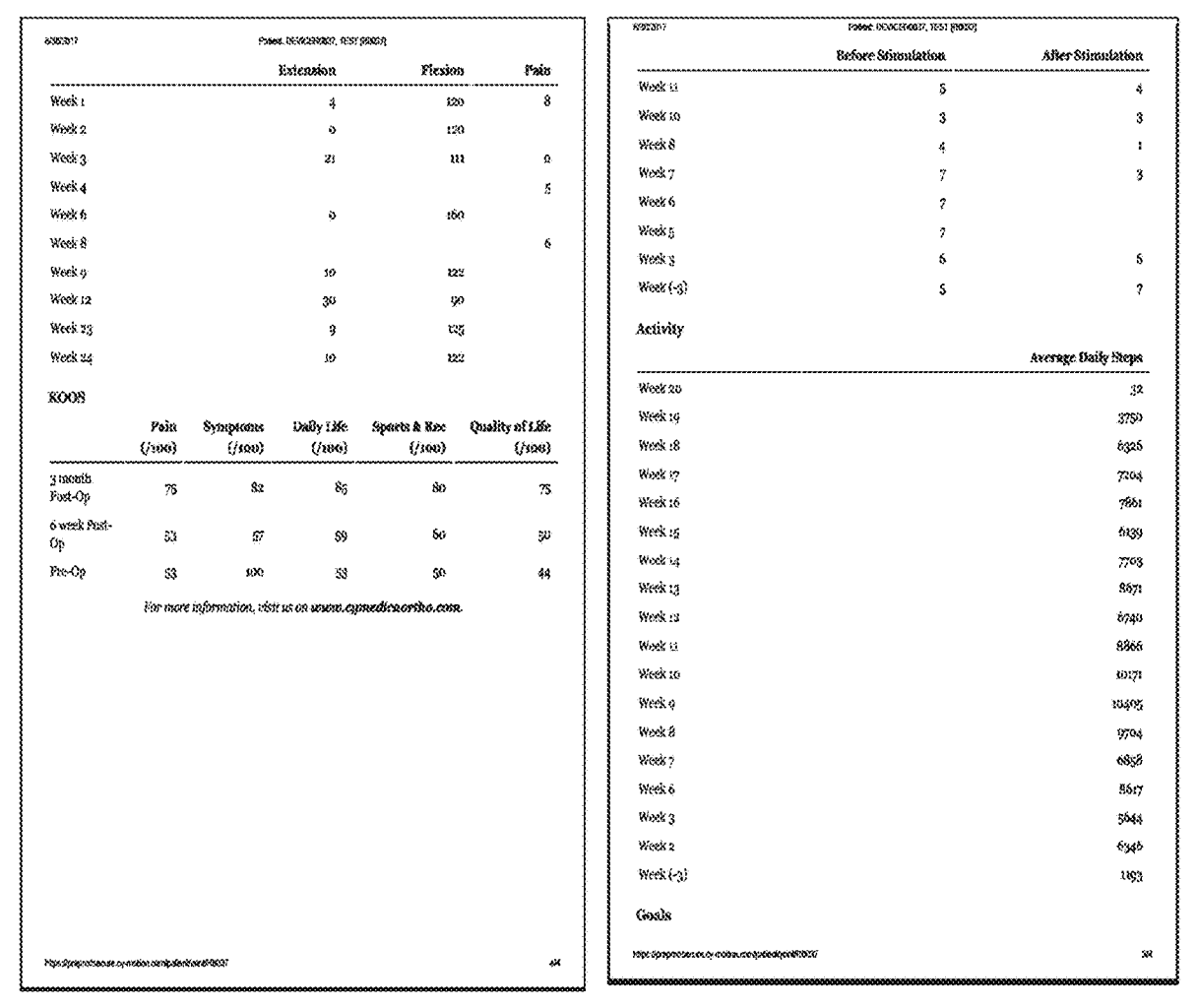

Some embodiments include a graphical view of longitudinal data for a patient with graphical and/or tabular data for ROM. For example, FIG. 81 illustrates a patient overview window 8100 in accordance with some embodiments of the invention. (e.g., including flex/ext/ROM degrees), and/or NMES/TENS stimulation (power levels, # sessions), and/or pain levels (e.g., vas scale), and/or activity levels (e.g. steps), and/or patient reported outcome measures (PROMs), such as KOOS/KOOS JR/HOOS JR, etc., and/or rehabilitation goals. Further, FIG. 82 illustrates a tabular view of a patient overview window 8200 with tabulated longitudinal data for that patient. In some embodiments, the windows 8100, 8200 can include graphical/tabular toggles to enable switching or rotating between graphical and tabular data views. In some embodiments, the system can enable the generation of printable patient overview charts. For example, FIGS. 83A-83B, and 84A-84B illustrate patient overview printable charts in accordance with some embodiments of the invention. Some embodiments include formatted charts for printing or exporting, saving to PDF, saving to electronic health record (EHR/EMR), etc.

In some embodiments, the system can display graphical and tabular data simultaneously. For example, FIG. 85 illustrates a patient stimulation detail window 8500 in accordance with some embodiments of the invention. In some embodiments, the window 8500 can include a detailed graphical and tabular view of longitudinal stimulation data. In some embodiments, the window 8500 can include power levels by zone, and/or the number of completed sessions, and/or the stimulation time, and/or the number of sessions per week, and/or the last session details, and/or any yellow/green flags based on customizable settings. FIG. 86 illustrates a patient range-of-motion (ROM) detail window 8600 in accordance with some embodiments of the invention. Some embodiments include detailed graphical and tabular view of longitudinal ROM data, including, but not limited to flexion (degrees), extension/hyper extension (degrees), and/or ROM (degrees). Other embodiments can include the number of sessions, and/or the last measurement details. Further embodiments can include colored flags (e.g., such as red/yellow/green flags) based on customizable settings.

Figure 87:
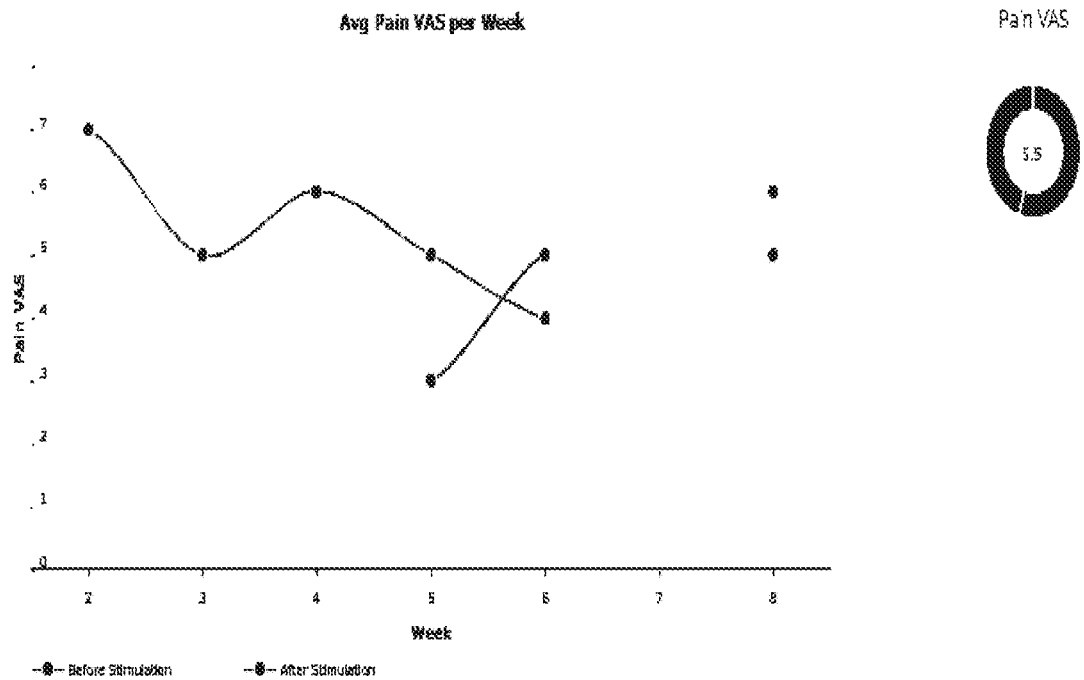
FIGS. 87-88 illustrate patient pain detail windows in accordance with some embodiments of the invention.
Figure 88:
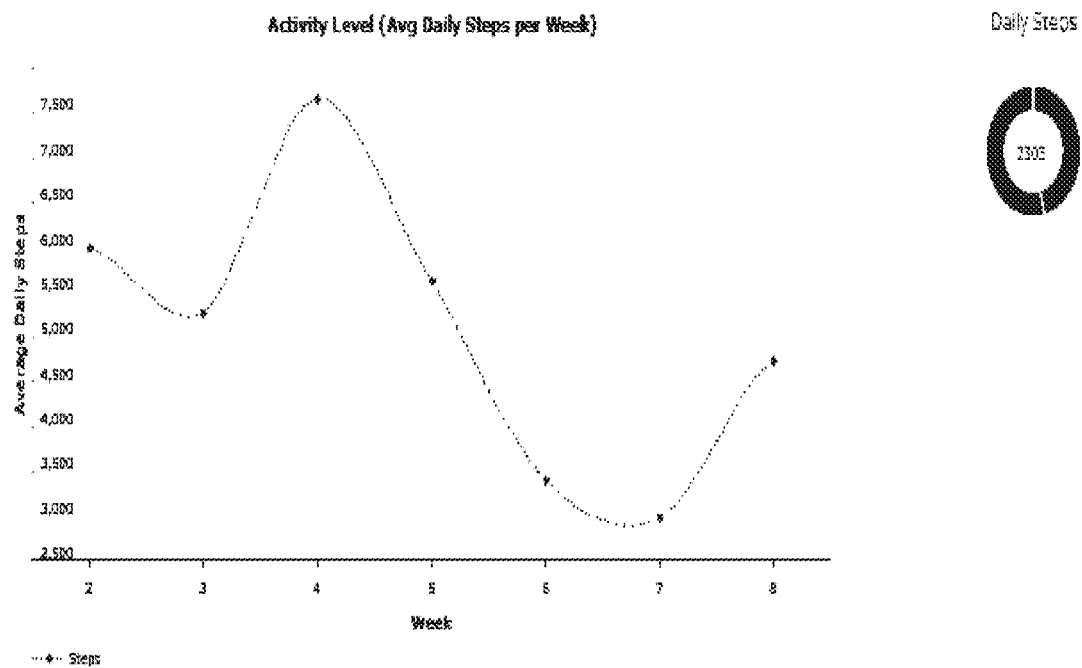

Some embodiments include a detailed graphical and tabular view of longitudinal pain data that includes average pain values (vas—visual analog scale), and/or pre/post stimulation session data, and/or last measurement details, and/or red/yellow/green flags based on customizable settings. For example, FIGS. 87-88 illustrate patient pain detail windows 8700, 8800 in accordance with some embodiments of the invention. Further, some embodiments can include a detailed graphical and tabular view of longitudinal activity data including average daily steps and/or last measurement details.

Figure 89:
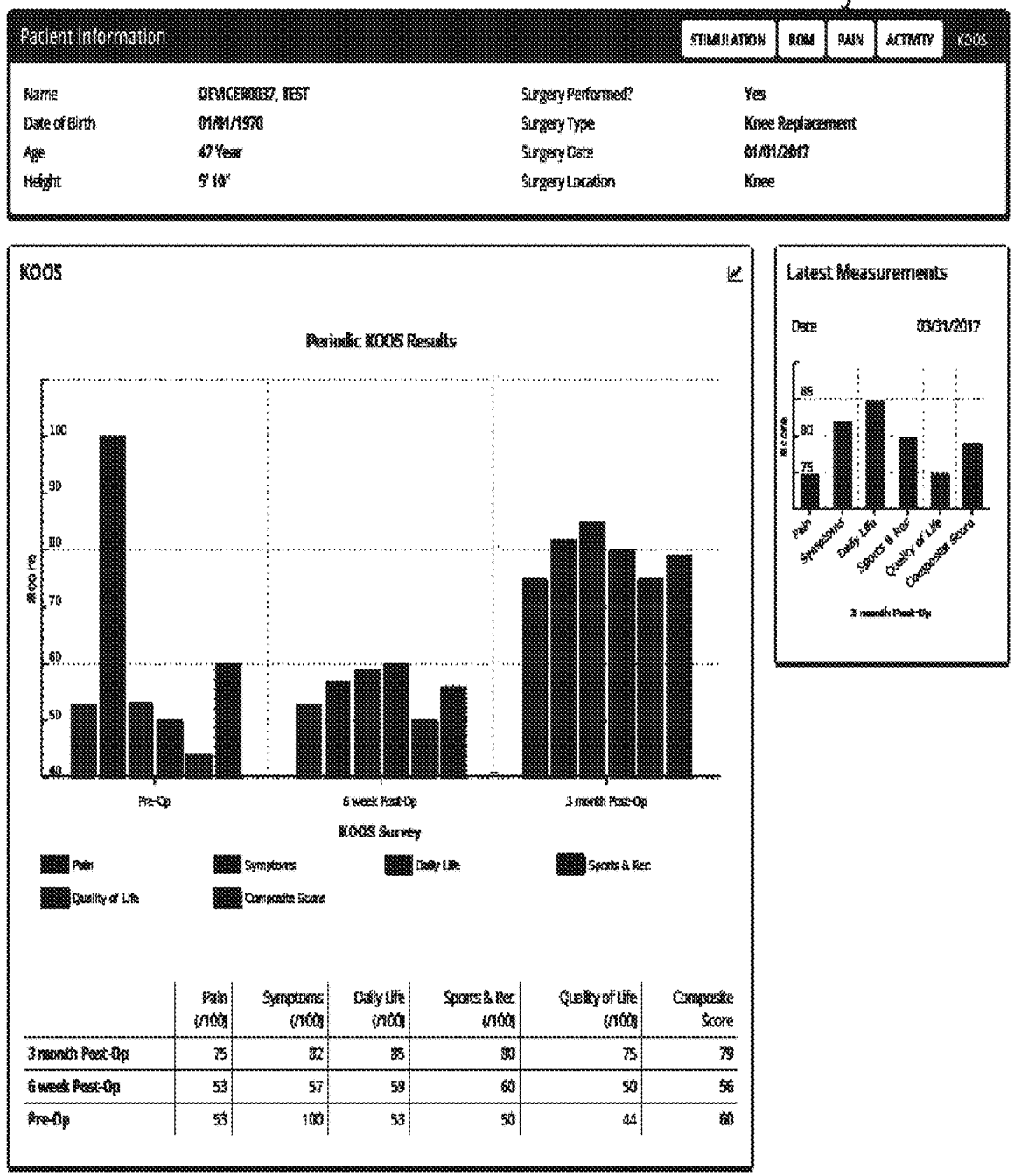
FIG. 89 illustrate patient passive range of motion (PROM) n accordance with some embodiments of the invention.

Some embodiments include passive range of motion data. For example, FIG. 89 illustrates patient passive range of motion (PROM) 8900 in accordance with some embodiments of the invention. Some embodiments include a detailed graphical and tabular view of longitudinal PROMs data, including, but not limited to KOOS/KOOS JR, HOOS/HOOS JR, VR-12, patient satisfaction surveys. Some embodiments include category and composite scores, data viewed by survey time point(s), and/or latest measurement details.

Some embodiments include a real-time rehabilitation and tracking system. For example, in some embodiments, a patient can download a mobile application and pair a rehabilitation system to one or more personal mobile devices. For example, any of the brace systems or assemblies that can capture range of motion (hereinafter "ROM") described earlier can be the rehabilitation system that can be paired to the mobile devices. In some embodiments, the mobile device application can serve as a user interface to operate a device via Bluetooth®. In some embodiments, the rehabilitation system can perform NMES/TENS stimulation, and/or measure ROM, and/or record pain levels, and/or record activity levels, and/or administer patient reported outcome measures (PROMs) per desired time-points. In some embodiments, the mobile device can transmit all data up to system cloud servers via WiFi or cellular data (usage data, measurements, patient profile information, etc.).

Figure 90C:
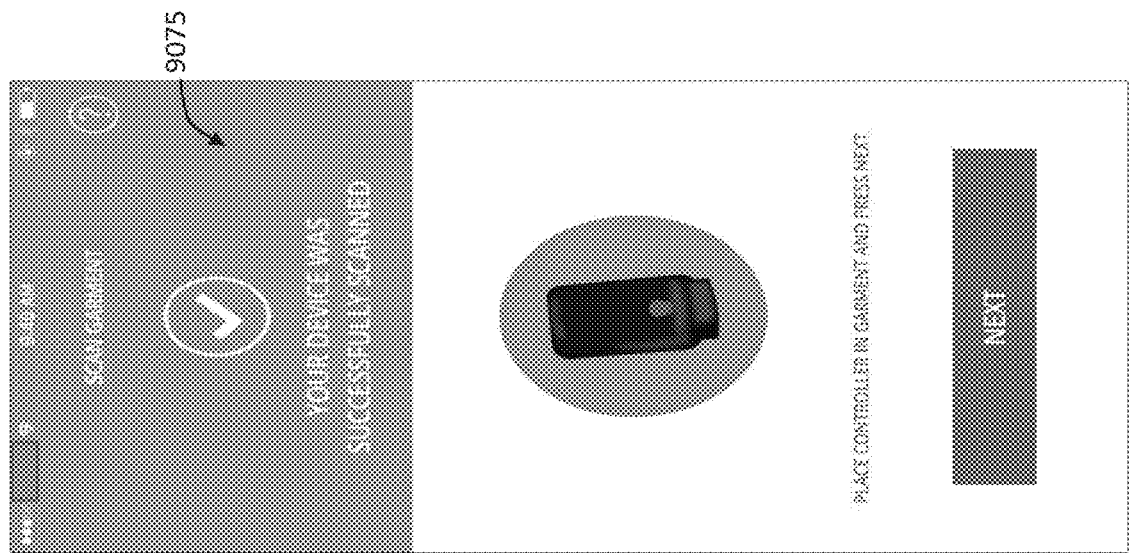
FIG. 90C illustrates an information mobile application screen in accordance with some embodiments of the invention.
Figure 90B:
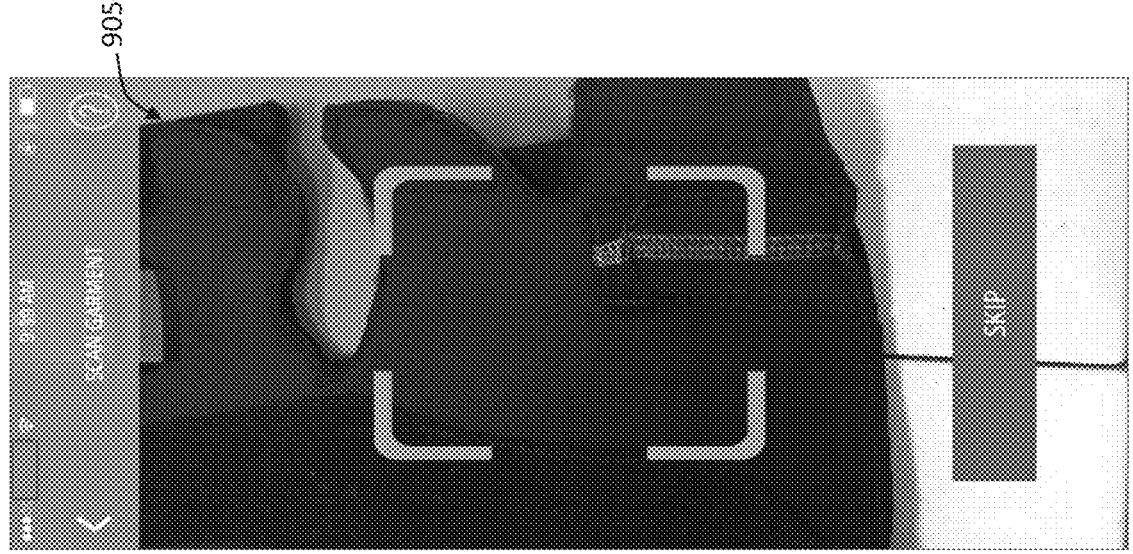
FIG. 90B illustrates scan mobile application screen in accordance with some embodiments of the invention.
Figure 90A:
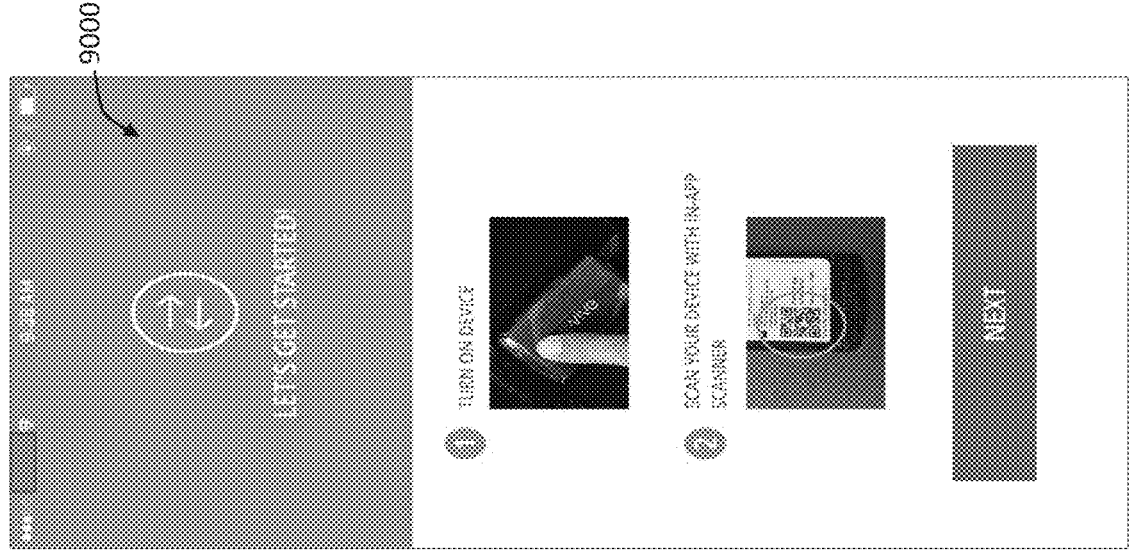
FIG. 90A illustrates start mobile application screen in accordance with some embodiments of the invention.

Various display screen content produced by the real-time rehabilitation and tracking system is shown in FIGS. 90A-98. For example, FIG. 90A illustrates start mobile application screen 9000 in accordance with some embodiments of the invention. In some embodiments, the screen 9000 can include a visual static or animated display of a representation of a user turning on one or more components or assemblies of the real-time rehabilitation and tracking system. For example, in some embodiments, a patient can be shown as accessing and turning on a brace system or assembly and any barcode or specification information.

Further, FIG. 90B illustrates scan mobile application screen 9050 in accordance with some embodiments of the invention. In some embodiments, the screen 9050 can include an illustration of scanning a garment comprising the rehabilitation and tracking system. In some embodiments, following a successful device scan, the device can display an information screen. For example, FIG. 90C illustrates an information mobile application screen 9075 in accordance with some embodiments of the invention. FIG. 91A illustrates a start stimulation mobile application screen 9100 in accordance with some embodiments of the invention. In some embodiments, the screen 9100 can include information related to therapy type and recommendations.

Figure 91B:
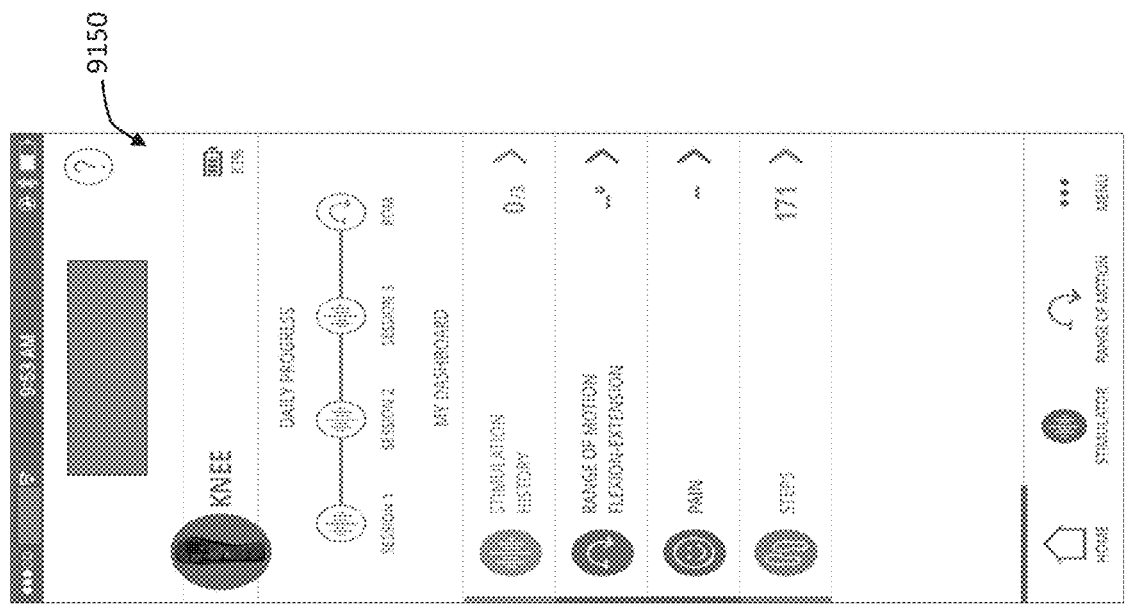
FIG. 91B illustrates a dashboard mobile application screen in accordance with some embodiments of the invention.
Figure 91A:
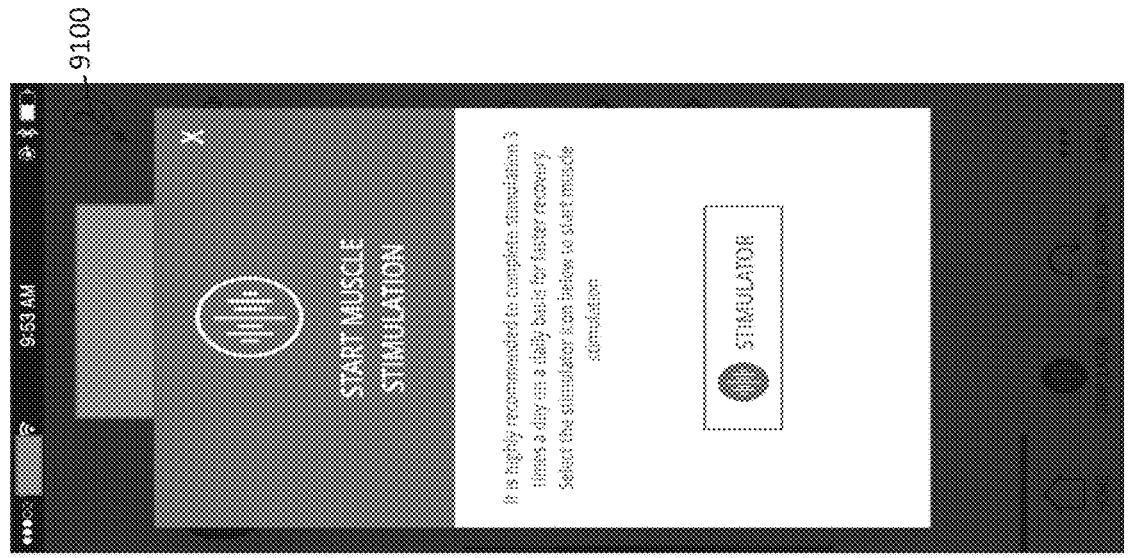
FIG. 91A illustrates a start stimulation mobile application screen in accordance with some embodiments of the invention.

FIG. 91B illustrates a dashboard mobile application screen 9150 in accordance with some embodiments of the invention. In some embodiments, the screen 9150 can include access icons for home, stimulator, ROM, and menu. In some embodiments, the screen 9150 can include a daily progress display showing progressive sessions. In some embodiments, access tabs can be provided that are configured to access stimulation history, and/or ROM/flexion-extension, and/or pain, and/or steps. In some embodiments, the user can use the screen 9150 to reversibly access one or more of the access tabs using the screen 9150 as the main or control screen.

FIG. 92A illustrates a stimulator session start mobile application screen 9200 in accordance with some embodiments of the invention. In some embodiments, the screen 9200 can include an indication of the session number of type, and/or an indication of the body part receiving therapy and/or can provide information on the therapy such as therapy time, and/or the recommended times and/or days or dates of therapy.

FIG. 92B illustrates a pain survey mobile application screen 9225 in accordance with some embodiments of the invention. In some embodiments, the screen 9225 can include a stimulation survey and can display a selectable gauge of pain level. In some embodiments, the screen 9225 can be shown prior to initiation of a stimulation session. In some embodiments, the system can display options for treatment programs prior to initiation of treatment. For example, FIG. 92C illustrates a stimulation treatment mobile application screen 9250 in accordance with some embodiments of the invention. In some embodiments, the screen 9250 can display a selection option of a "post-op" program and/or a "strength" program.

Figures 93A, 93B, 93C:
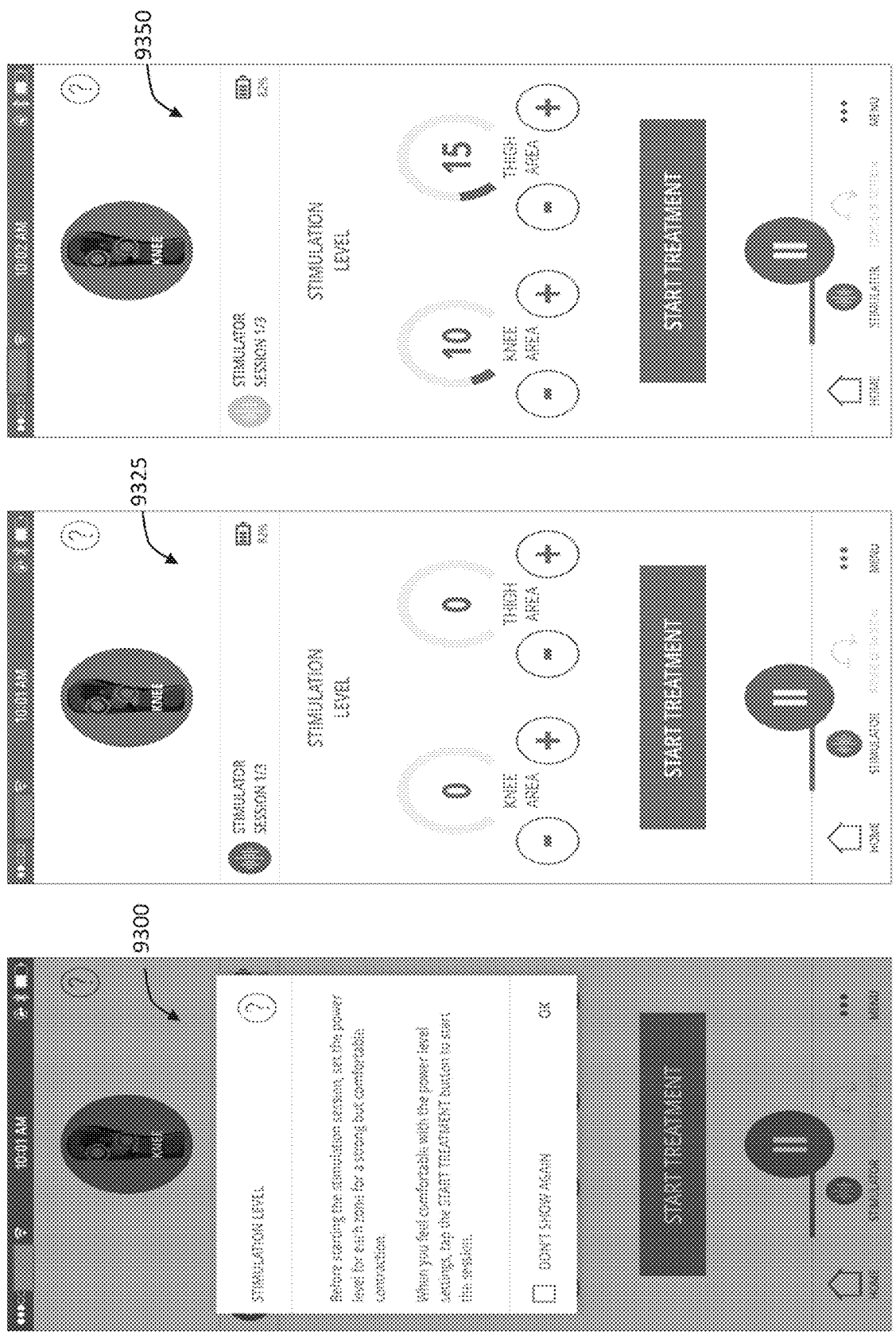
FIG. 93A illustrates a stimulation level information mobile application screen in accordance with some embodiments of the invention.
FIGS. 93B-93C, and 94A illustrate stimulation level mobile application screens in accordance with some embodiments of the invention.
Figure 94B:
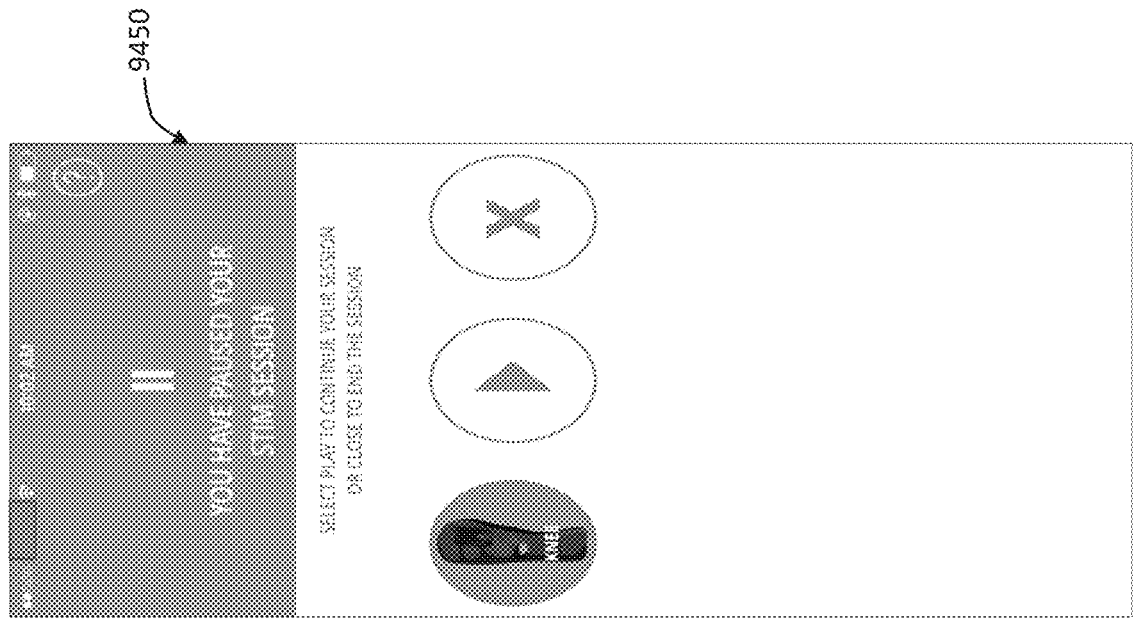
FIG. 94B illustrates a stimulation information mobile application screen in accordance with some embodiments of the invention.
Figure 94A:
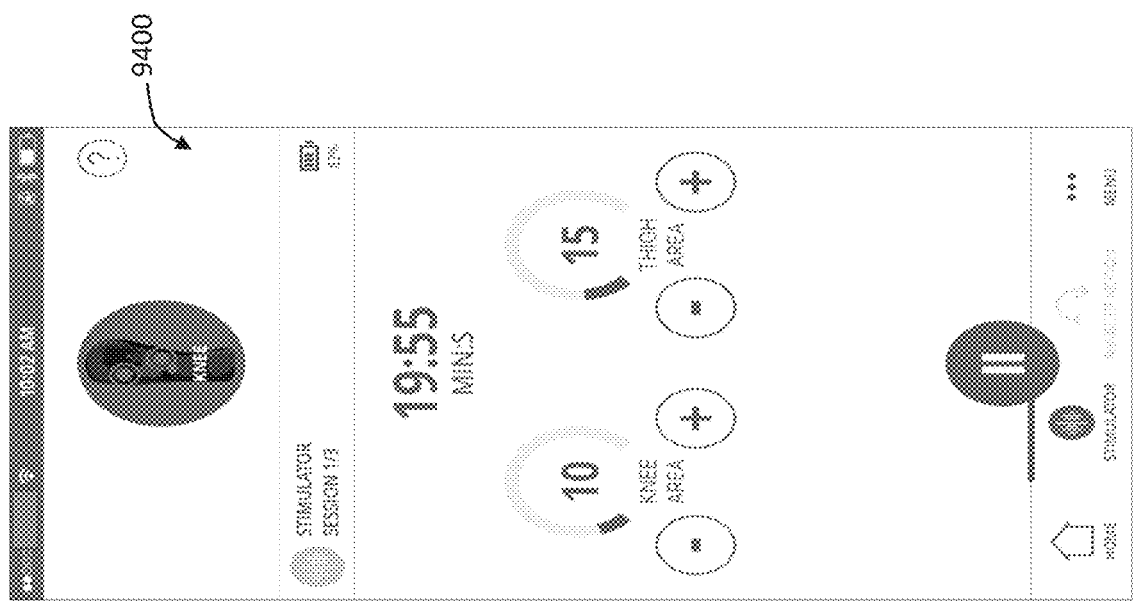

Some embodiments include a stimulation alert window. FIG. 93A illustrates a stimulation level information mobile application screen 9300 in accordance with some embodiments of the invention. In some embodiments, a prompt can be displayed to urge a user to proceed when the user us ready to commence therapy. FIGS. 93B-93C, and 94A illustrate stimulation level mobile application screens 9325, 9350, 9400 in accordance with some embodiments of the invention. In some embodiments, the screens 9325, 9350, 9400 can include an indication or display of a session number or type, and/or at least one stimulation level selector or indicator. In some embodiments, the stimulation level selector or indicator can comprise a toggle to increase or decrease the stimulation level and an indicator showing the stimulation level and/or a numeric indicator of the stimulation level. As shown in FIG. 94A, some embodiments include a timer display for the therapy session. In some embodiments, the stimulation can be stopped or paused. For example, FIG. 94B illustrates a stimulation information mobile application screen 9450 shown after pausing a therapy session.

Figures 95A, 95B, 95C:
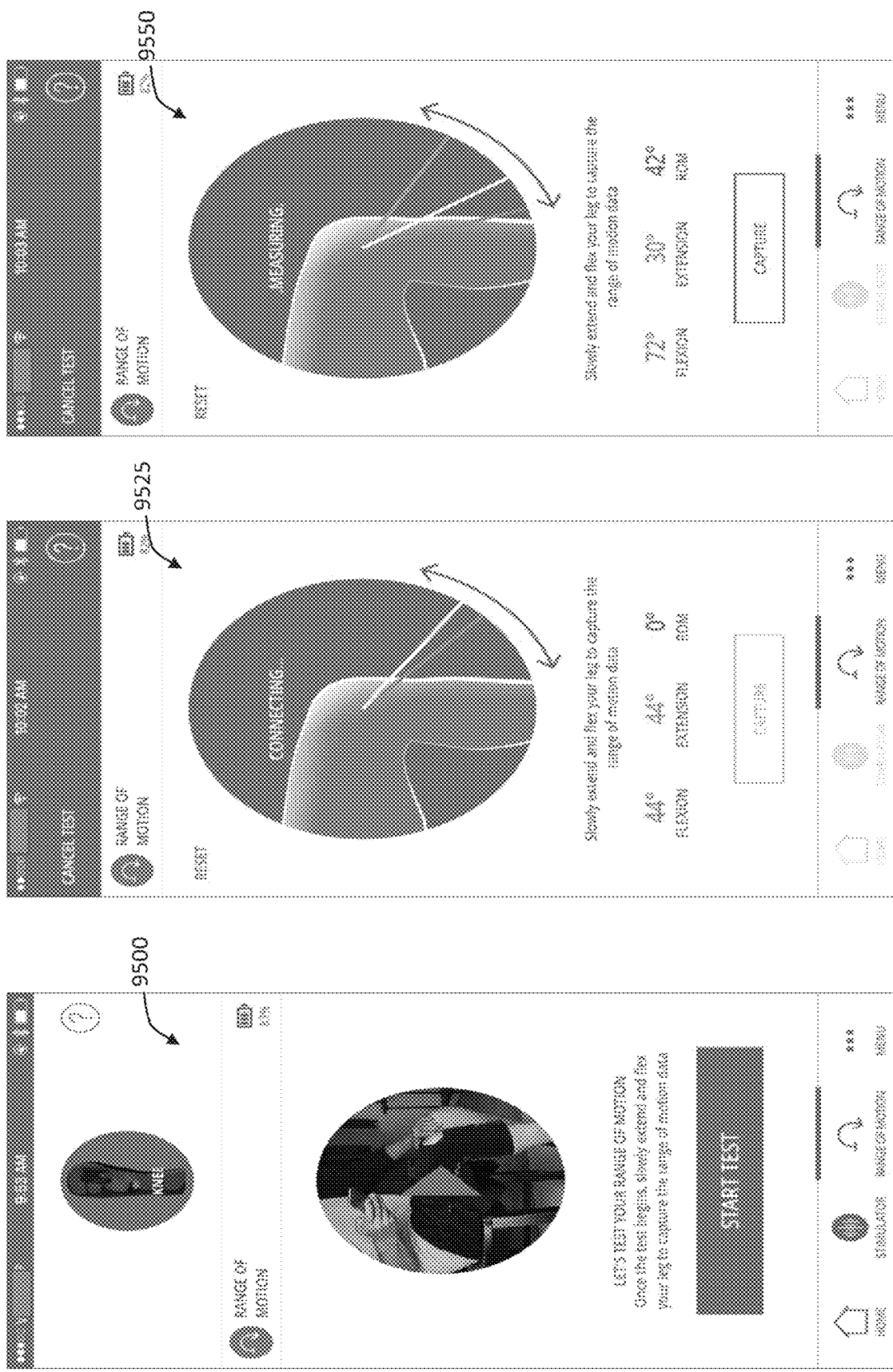
FIG. 95A illustrates a range of motion (ROM) start mobile application screen in accordance with some embodiments of the invention.
FIG. 95B illustrates a range of motion (ROM) connecting mobile application screen in accordance with some embodiments of the invention.
Figures 96A, 96B:
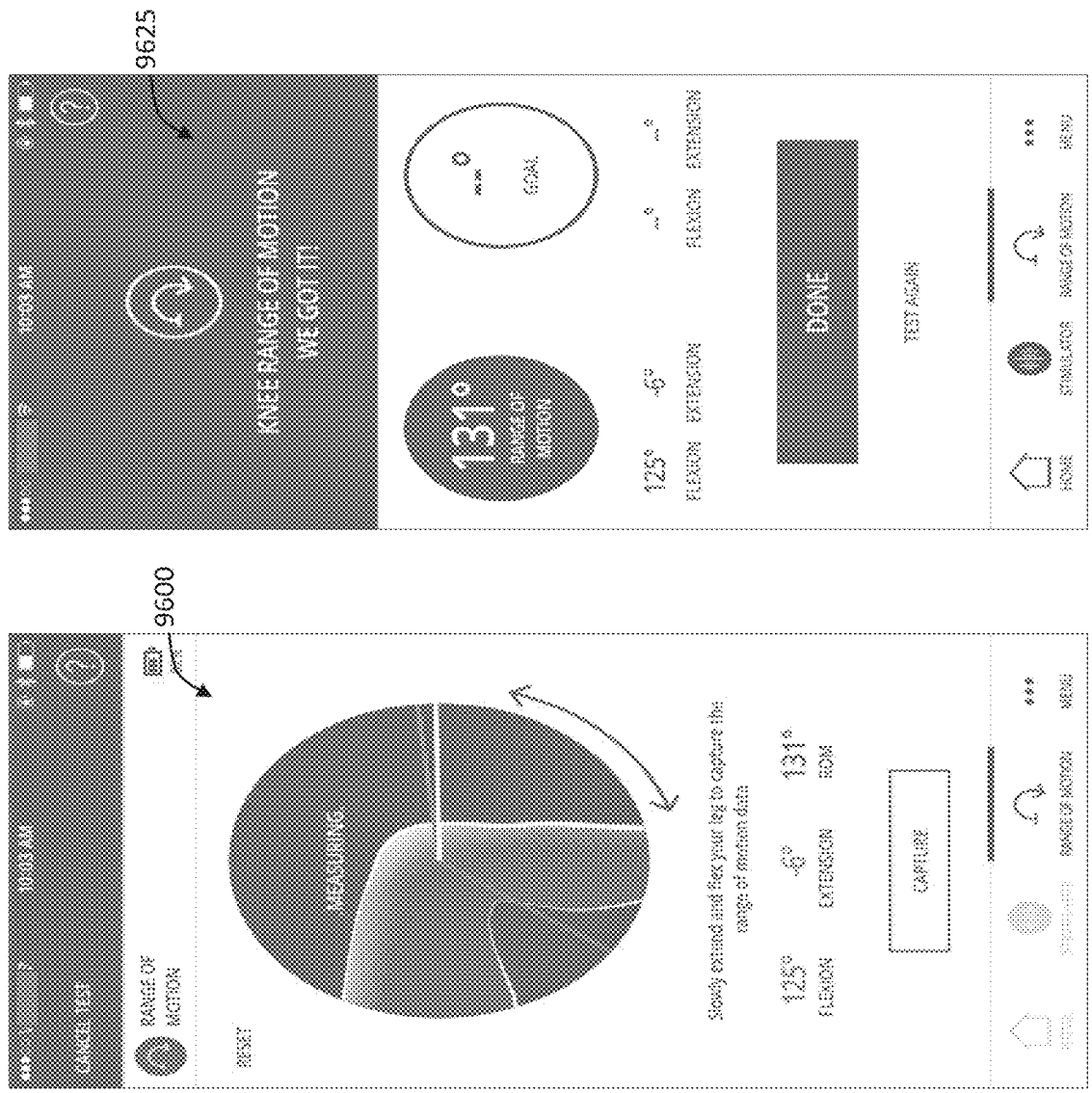

Some embodiments include display screens illustrative of ROM therapy. For example, FIG. 95A illustrates a range of motion (ROM) start mobile application screen 9500 in accordance with some embodiments of the invention. In some embodiments, the screen 9500 can include a static or animated display of a ROM exercise and an access or start icon to enable a user to start a ROM test. FIG. 95B illustrates a range of motion (ROM) connecting mobile application screen 9525 in accordance with some embodiments of the invention. In some embodiments, the screen 9525 can include a display showing a ROM image or animation to enable a user to visualize a ROM. In some embodiments, the screen 9525 can include a display of flexion, and/or extension, and or ROM. FIGS. 95C and 96A illustrate a range of motion (ROM) measuring mobile application screen 9550, 9600 in accordance with some embodiments of the invention. In some embodiments, the screen 9550, 9600 can include a ROM image or animation to enable a user to visualize a ROM measurement. FIG. 96B illustrates a range of motion (ROM) results mobile application screen 9625 in accordance with some embodiments of the invention. In some embodiments, the screen 9625 can include a display of ROM based on one or more ROM therapy sessions. In some embodiments, the screen 9625 can include a ROM display of a goal ROM, and can include a goal flexion and/or extension angle.

FIG. 97A illustrates a settings mobile application screen 9700 in accordance with some embodiments of the invention. In some embodiments, the screen 9700 can include a settings display comprising one or more selectable or adjustable settings. For example, some embodiments include a selectable toggle for "complete stimulation". Some further embodiments include a selectable toggle for "complete range of motion". Some further embodiments include a selectable toggle for "replace electrodes". Some further embodiments include a selectable toggle for "complete my profile". Some other embodiments include a range of motion adjustment. In some embodiments, any of the selectable or adjustable settings can be selected to display one or more selectable icons, and/or data fields. For example, FIG. 97B illustrates a profile mobile application screen 9725 in accordance with some embodiments of the invention. In some embodiments, the screen 9725 can include one or more selectable icons, and/or data fields related to a user's profile.

Figure 98:
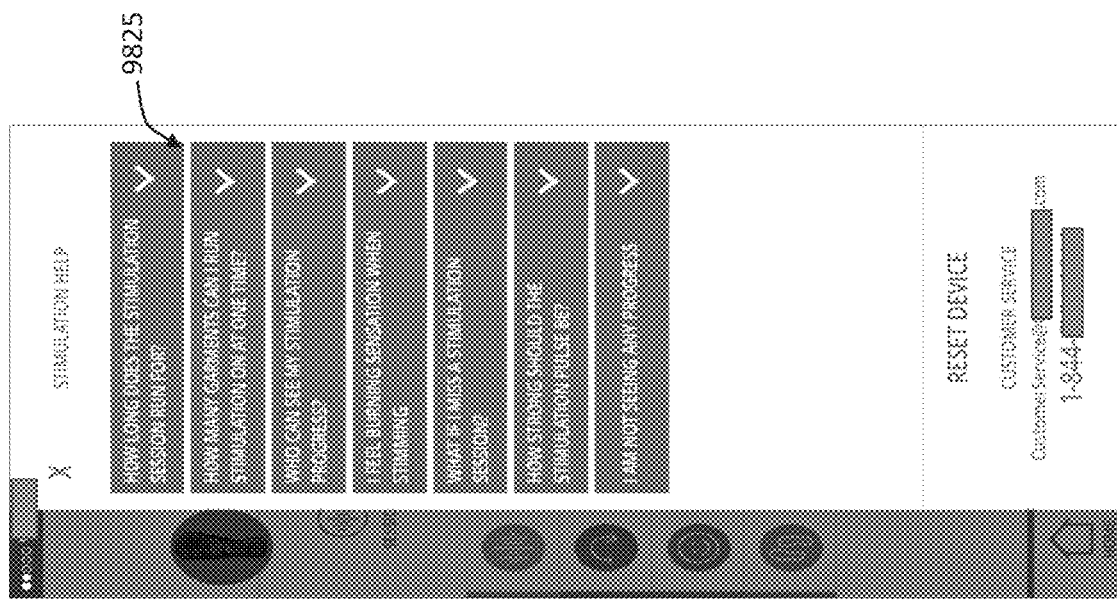

FIG. 97C illustrates a set your goals mobile application screen 9750 in accordance with some embodiments of the invention. In some embodiments, the screen 9750 can include information related to one or more goals, and/or one or more selectable icons, and/or data fields related to a user's goals. FIG. 98 illustrates a stimulation help mobile application screen 9825 in accordance with some embodiments of the invention. In some embodiments, the screen 9825 can include one or more help topics related to stimulation or other therapy related procedures or actions.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein. Various features and advantages of the invention are set forth in the following claims.

The invention claimed is:

1. A system comprising:
   at least one sensor comprising a plurality of electrodes including at least one active electrode and at least one receiving electrode, the at least one sensor configured and arranged to couple with a patient's tissue forming an electrical circuit with control electronics of at least one controller, the electrical circuit configured and arranged to measure an electrical parameter and to form a closed loop electrical muscle stimulation system, wherein a stimulation current or voltage applied by the sensor is based on at least one program and the at least one electrical parameter,
   the at least one controller configured and arranged for (a) applying a sense electrical pulse to the tissue, (b) measuring the at least one electrical parameter, and (c) adjustably applying an oscillating stimulation pulse to alternating, non-overlapping muscle groups associated with the tissue based at least in part on the measured electrical parameter, the stimulation being adjustably controlled by the at least one controller to maintain a constant power output to the tissue based at least in part on the at least one electrical parameter, and (d) repeat steps (a)-(c);
   a good coupled to at least one computer readable medium configured to store usage data relating to the patient's use of the good;
   a computing program, applet or application configured to upload usage data for analysis, wherein at least a portion of the computing program, applet or application is configured and arranged to include at least one user interface configured to display at least some of the usage data and to enable control of a parameter of the good.

2. The system of claim 1, wherein the at least one controller is configured and arranged to electromagnetically couple with a computing device using at least a portion of the computing program, applet or application.

3. The system of claim 1, wherein the at least one controller is configured to update the at least one user interface with at least one of a status of a portion of the good, a position of a portion of the good, and data from the at least one sensor.

4. The system of claim 1, wherein the at least one user interface comprises a display including an option to scan and synchronize the good with the at least one controller.

5. The system of claim 1, wherein the at least one user interface comprises a display including an option to scan and synchronize more than one good.

6. The system of claim 1, wherein the at least one user interface comprises a display including an option to activate a wired or wireless link to connect the good with the at least one controller.

7. The system of claim 6, wherein the display is configured and arranged to enable the user to set or reconfigure the at least one stimulation pulse.

8. The system of claim 6, wherein the display is configurable by the at least a portion of the computing program, applet or application to display one or more parameters related to at least one of stimulation provided by at least a portion of the good, and a range of motion measured by at least a portion of the good.

9. The system of claim 6, wherein the display is configurable by the at least a portion of the computing program, applet or application to provide a visual representation of an action of a user wearing at least a portion of the good that is related to at least one of stimulation provided by at least a portion of the good, and a range of motion measured by at least a portion of the good.

10. The system of claim 2, wherein the computing device comprises at least one of a desktop computer, a laptop computer, a digital tablet, a digital assistant, a cellular or smart phone, a smart watch, a wearable activity monitor, a pair of glasses, a camera, a pager, and an internet appliance.

11. The system of claim 1, wherein the good comprises a brace assembly.

12. The system of claim 11, wherein the brace assembly comprises at least one of a brace, a stay, a sleeve, a band, a sling, a garment, a wrap, and a strap.

13. The system of claim 1, wherein the at least one sensor comprises at least one of an accelerometer, a motion sensor, a proximity sensor, an optical sensor, a motion sensor, a gyrometer, a magnetometer, a proximity sensor, a hydration sensor, a force or pressure sensor, a position sensor, a global positioning sensor (GPS), an optical sensor, a magnetic sensor, a magnetometer, an inductive sensor, a capacitive sensor, an eddy current sensor, a resistive sensors, a magnetoresistive sensor, an inductive sensor, an infrared sensor, an inclinometer sensor, a piezoelectric materials or piezoelectric-based sensor, a blood-oxygen sensor, a heart-rate sensor, a laser or ultrasound based sensor, and an electromyography type sensor.

14. The system of claim 1, further comprising a remote server including a computing program, applet or application configured to initiate or maintain an exchange of the usage data between the good and the server and/or a coupled mobile computing device and the server.

15. The system of claim 14, wherein the server is configured as a host to a web portal or coupled to a host server providing the web portal, the web portal configured to access or display the usage data or at least one parameter related to use of at least a portion of the good.

16. The system of claim 15, wherein the web portal is configurable to create one or more alerts based on at least one user customization criteria related to the usage data, wherein the criteria can include at least one of a level of use of at least a portion of the good by a user, a limit of use of at least a portion of the good by the user, a time of use of at least a portion of the good by the user, a type of use of at least a portion of the good by the user, and a behavior of at least a portion of the good while in use by the user.

17. The system of claim 16, wherein the alert comprises at least one of an email, a text or SMS message, a displayed icon, rendered text, a rendered graphic, a categorized or customized alert.

18. The system of claim 16, wherein the at least one user customization criteria includes at least one of a monitoring window, usage rate and/or activity level, one or more specified compliance or rehabilitation goals, compliance rate, range of motion (ROM), and pain values.

* * * * *